US009388193B2

(12) United States Patent
Chen et al.

(10) Patent No.: US 9,388,193 B2
(45) Date of Patent: Jul. 12, 2016

(54) DIPICOLYLAMINE DERIVATIVES AND THEIR PHARMACEUTICAL USES

(71) Applicants: National Health Research Institutes, Zhunan (TW); Molecular Targeting Technologies, Inc., West Chester, PA (US)

(72) Inventors: Chiung-Tong Chen, Zhunan (TW); Kak-Shan Shia, Taipei (TW); Chien-Huang Wu, Zhonghe (TW); Lun-Kelvin Tsou, Zhunan (TW); Yu-Sheng Chao, New York, NY (US)

(73) Assignees: National Health Research Institutes, Zhunan Town (TW); Molecular Targeting Technologies, Inc., West Chester, PA (US)

(*) Notice: Subject to any disclaimer, the term of this patent is extended or adjusted under 35 U.S.C. 154(b) by 0 days.

(21) Appl. No.: 14/711,946

(22) Filed: May 14, 2015

(65) Prior Publication Data

US 2015/0336976 A1    Nov. 26, 2015

Related U.S. Application Data

(60) Provisional application No. 62/001,725, filed on May 22, 2014.

(51) Int. Cl.
| | | |
|---|---|---|
| *A61K 31/4745* | (2006.01) | |
| *C07D 491/22* | (2006.01) | |
| *C07D 405/14* | (2006.01) | |
| *C07D 491/147* | (2006.01) | |
| *C07D 305/14* | (2006.01) | |

(52) U.S. Cl.
CPC ............ *C07D 491/22* (2013.01); *C07D 305/14* (2013.01); *C07D 405/14* (2013.01); *C07D 491/147* (2013.01)

(58) Field of Classification Search
USPC .............................. 514/283, 332; 546/48, 256
See application file for complete search history.

(56) References Cited

U.S. PATENT DOCUMENTS

| 8,436,170 B2* | 5/2013 | Mao ...................... C07D 311/88 544/405 |
| 2008/0171351 A1 | 7/2008 | Smith |
| 2009/0214430 A1 | 8/2009 | Lee et al. |
| 2013/0323172 A1 | 12/2013 | Gray et al. |
| 2013/0338368 A1* | 12/2013 | Suzuki ................. C07D 405/14 546/256 |
| 2014/0212335 A1* | 7/2014 | Lee .......................... A61L 9/00 422/30 |

FOREIGN PATENT DOCUMENTS

| WO | WO-2007/002204 A2 | 1/2007 |
| WO | WO-2010/006755 A2 | 1/2010 |

OTHER PUBLICATIONS

Lee, J-J. et al.: Synthetic ligand-coated megnetic nanoparticles for microfluidic bacterial separation from blood. Nano Lett., vol. 14, pp. 1-5, 2014.*
Leevy, W.M. et al.: Selective recognition of bacterial membranes by Zinc(II)-coordination complexes. Chem. Commun., vol. 15, pp. 1595-1597, 2006.*
Wyffels et al "Synthesis and Preliminary Evaluation of Radiolabeled Bis(zinc(II)-dipicolylamine) Coordination Complexes as Cell Death Imaging Agents" Bioorganic & Medicinal Chemistry vol. 19, pp. 3425-3432. 2011.
Plaunt et al "Library Synthesis, Screening, and Discovery of Modified Zing(II)-Bis(dipicolylamine) Probe for Enhanced Molecular Imaging of Cell Death" Bioconjugate Chemistry vol. 25, pp. 724-737. 2014.
Xue et al "Modulating Affinities of Di-2-Picolylamine (DPA)-Substituted Quinoline Sensors for Zing Ions by Varying Pendant Ligands" Inorganic Chemistry vol. 47, pp. 4310-4318. 2008.
Milaeva et al "Metal Complexes with Functionalised 2,2'-Dipicolylamino Ligand Containing an Antioxidant 2,6-Di-*Tert*-Butylphenol Moiety: Synthesis and Biological Studies" Dalton Transactions vol. 42, p. 6817-6828. 2013.
Leevy et al "Selective Recognition of Bacterial Membranes by Zinc(II)-Coordination Complexes" Chem. Commun. pp. 1595-1597, 2006.
Molecular Targeting Technologies, Inc. "Novel Molecular and Cellular Imaging Reagents for Life Sciences and Drug Discovery", 2012.
Department of Industrial Technology, Moea, Taiwan, White Paper of Industrial Technology, Chapter 4: "Biotechnology Drugs" pp. 281-290, 2013.
Chu et al "In Vivo Imaging of Brain Infarct with the Novel Fluorescent Probe PSVue 794 in a Rat Middle Cerebral Artery Occlusion-Reperfusion Model" Molecular Imaging vol. 12, pp. 8-16, 2013.
Xiao et al "Convenient Synthesis of Multivalent Zing(II)-Dipicolylamine Complexes for Molecular Recognition" Tetrahedron Letters vol. 54, pp. 861-864, 2013.

* cited by examiner

*Primary Examiner* — Charanjit Aulakh
(74) *Attorney, Agent, or Firm* — Cesari and McKenna LLP

(57) ABSTRACT

Dipicolylamine compounds of Formula (I) set forth herein. Also disclosed are pharmaceutical compositions containing metal ions and these compounds. Further disclosed is a method for treating a condition associated with cells containing inside-out phosphatidylserine, with these compounds.

23 Claims, No Drawings

DIPICOLYLAMINE DERIVATIVES AND THEIR PHARMACEUTICAL USES

CROSS REFERENCE TO RELATED APPLICATIONS

This application claims the benefit of U.S. Provisional Application No. 62/001,725, filed on May 22, 2014, the content of which is hereby incorporated by reference in its entirety

BACKGROUND

Phosphatidylserine (PS), a membrane phospholipid, is typically localized to the internal surface of the membrane of a healthy cell. Under certain circumstances, PS is also found on the external surface. See Leventis et al., *Annu. Rev. Biophys.* 2010, 39, 407-27.

More specifically, PS is exposed on the external surface of cancer cells. See Thorpe et al., *Breast Cancer Res Treat* 1995, 36(2), 237-51; Ran et al., *Int. J. Radiat. Oncol. Biol. Phys.* 2002, 54(5), 1479-84; and Thorpe, *Thromb. Res.* 2010, 125 Suppl 2, S134-137. Further, recent studies found that PS exists in tumor vasculatures and tumor-derived microvessels. See Stafford et al., *Neoplasia.* 2011, 13, 299-308; and Yin et al., *Cancer Immunology Research* 2013, 1, 1-13. Moreover, in many pathogenic particles such as bacteria and viruses, PS is exposed at high levels on the external surface. See Huang et al., *Cancer Res.* 2005, 65(10), 4408-16; and White et al., *Bioconjug. Chem.* 2010, 21(7), 1297-1304. Finally, PS has been found on the outer surface of cells in which cell death pathways have been dysregulated. For example, in addition to cancer, conditions such as neurodegenerative disorders, cardiovascular disease, autoimmune diseases, and metabolic disorders demonstrate surface localization of PS. See Smith et al., *Mol. Pharm.* 2011, 8(2), 583-90. Thus, PS provides a valuable target for delivery of therapeutic agents for treating the conditions mentioned above.

Protein Annexin V is currently used to deliver therapeutic agents via binding to PS. However, this binding requires high levels of $Ca^{2+}$, which might activate "scramblases" that could externalize PS in nearby normal cells, resulting in undesired targeting of the normal cells.

There is a need to develop a delivery agent that selectively associates with disease-relevant PS to achieve site-specific delivery of a therapeutic agent.

SUMMARY

This invention is based on an unexpected discovery that certain dipicolylamine derivatives are effective in delivery a therapeutic agent to a target disease site that has phosphatidylserine on the external surfaces of cell membranes.

In one aspect, this invention relates to compounds of formula (I) shown below:

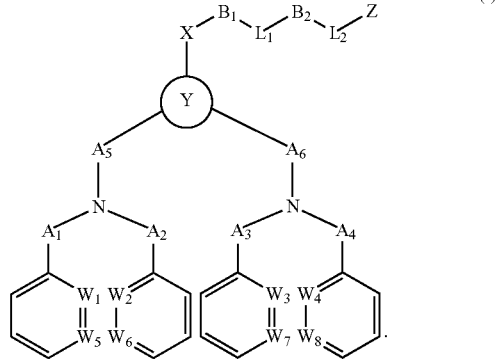

(I)

In this formula, each of $A_1$, $A_2$, $A_3$, $A_4$, $A_5$, $A_6$, and $B_1$, independently, is a $C_1$-$C_6$ bivalent aliphatic radical, a $C_1$-$C_6$ bivalent heteroaliphatic radical, a bivalent aryl radical, or a bivalent heteroaryl radical; $B_2$ is a bond, a $C_1$-$C_6$ bivalent aliphatic radical, a $C_1$-$C_6$ bivalent heteroaliphatic radical, a bivalent aryl radical, a bivalent heteroaryl radical, $D_1$-$NR_1$—C(O)-$D_2$, $D_1$-C(O)$NR_1$-$D_2$-$NR_1{'}$—C(O)-$D_3$, $D_1$-$D_2$-C(O)—$NR_1$—C(O)-$D_3$, or $D_1$-$D_2$-$D_3$, each of $D_1$, $D_2$, $D_3$, independently, being a $C_1$-$C_6$ bivalent aliphatic radical, a $C_1$-$C_6$ bivalent heteroaliphatic radical, a bivalent aryl radical, a bivalent heteroaryl radical, a $C_1$-$C_{10}$ bivalent aralkyl radical, or a $C_1$-$C_{10}$ bivalent heteroaralkyl radical, and each of $R_1$ and $R_1{'}$, independently, being H, a $C_1$-$C_6$ bivalent heteroaliphatic radical, a bivalent aryl radical, a bivalent heteroaryl radical, or a $C_1$-$C_{10}$ bivalent aralkyl radical; each of $L_1$ and $L_2$, independently, is a bond, $NR_2$, $NR_2C(O)$, $NR_2C(S)$, $NR_2CR_3R_4$, $NR_2SO_2$, $NR_2C(O)NR_3$ or $NR_2C(S)NR_3$, each of $R_2$, $R_3$, and $R_4$, independently, being H, a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, a $C_1$-$C_{14}$ monovalent heteroaralkyl radical, C(s)R' or C(O)R', in which R' is a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical, provided that at least one of $L_1$ and $L_2$ is not a bond; each of $W_1$, $W_2$, $W_3$, $W_4$, $W_5$, $W_6$, $W_7$, and $W_8$, independently, is N or $CR_5$, $R_5$ being H, halo, cyano, amino, hydroxyl, nitro, sulfhydryl, a $C_1$-$C_6$ aliphatic radical, a $C_1$-$C_6$ heteroaliphatic radical, or a haloaliphatic radical; X is a bond, O, S, or $NR_6$, $R_6$ being H, a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical; Y is a aryl ring or a heteroaryl ring; and Z is a therapeutic moiety.

Each of the aliphatic radical, the heteroaliphatic radical, the aralkyl radical, and the heteroaralkyl radical is unsubstituted or substituted with halo, cyano, amino, hydroxyl, nitro, sulfhydryl, $C_1$-$C_6$ alkoxy, $C_1$-$C_6$ alkylamino, $C_1$-$C_{12}$ dialkylamino, and $C_1$-$C_6$ haloalkyl; and each of the aryl radical and the heteroaryl radical is unsubstituted or substituted with halo, cyano, amino, hydroxyl, nitro, sulfhydryl, a $C_1$-$C_6$ aliphatic radical, a $C_1$-$C_6$ heteroaliphatic radical, or a haloaliphatic radical.

A subset of the compounds described above are those of formula (I), in which Y is

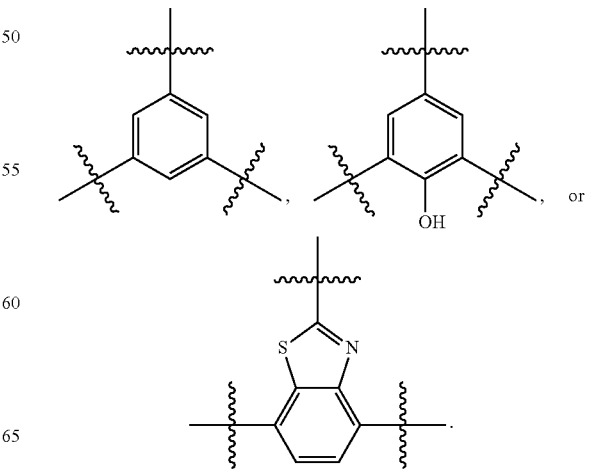

Referring to formula (I) again, another subset are those, in which each of $W_1$, $W_2$, $W_3$, and $W_4$ is N, and each of $W_5$, $W_6$, $W_7$, and $W_8$ is CH; or in which each of $W_1$, $W_2$, $W_3$, and $W_8$ is N, and each of $W_4$, $W_5$, $W_6$, and $W_7$ is CH.

Still another subset are those of formula (I), in which each of $A_1$, $A_2$, $A_3$, $A_5$, $A_5$, and $A_6$ is methylene.

Further, in the compounds of formula (I), $B_1$ can be ethylene, propylene, butylene, or hexylene; X can be O or NH; $L_2$ can be C(O).

Also, in the above-described compounds, $L_1$ can be a bond, NH, $NHCH_2$, NHC(O), $NHSO_2$, NHC(O)NH,

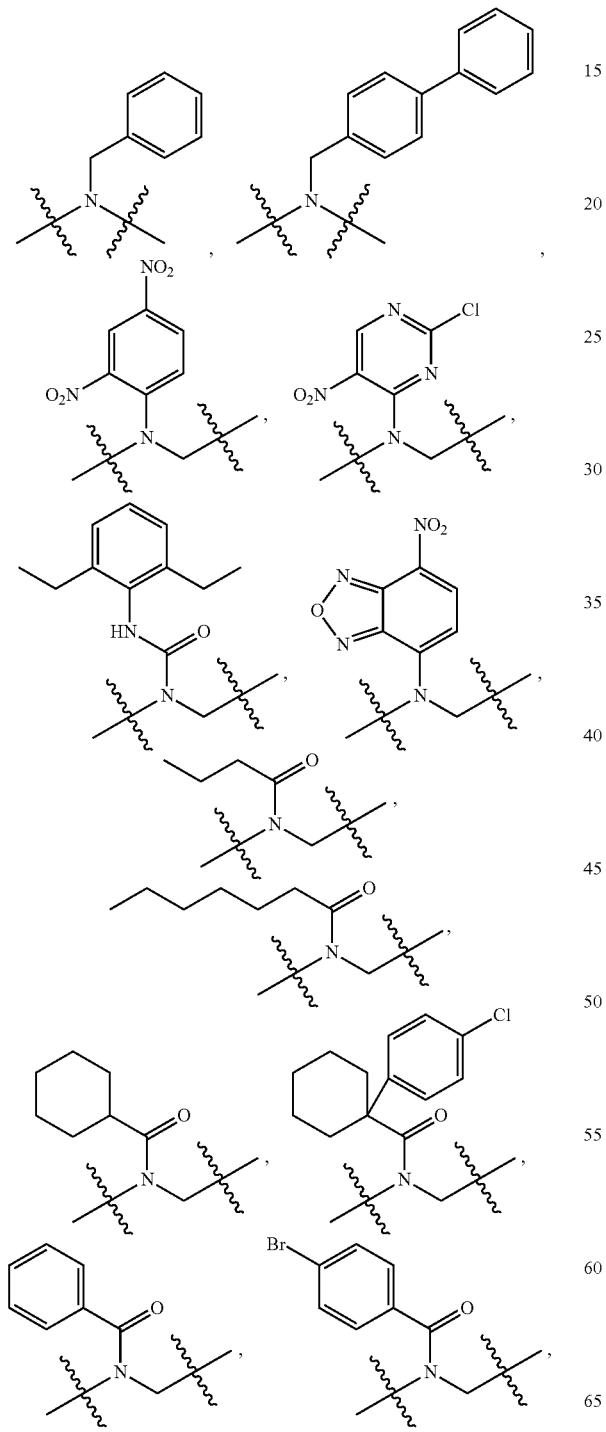

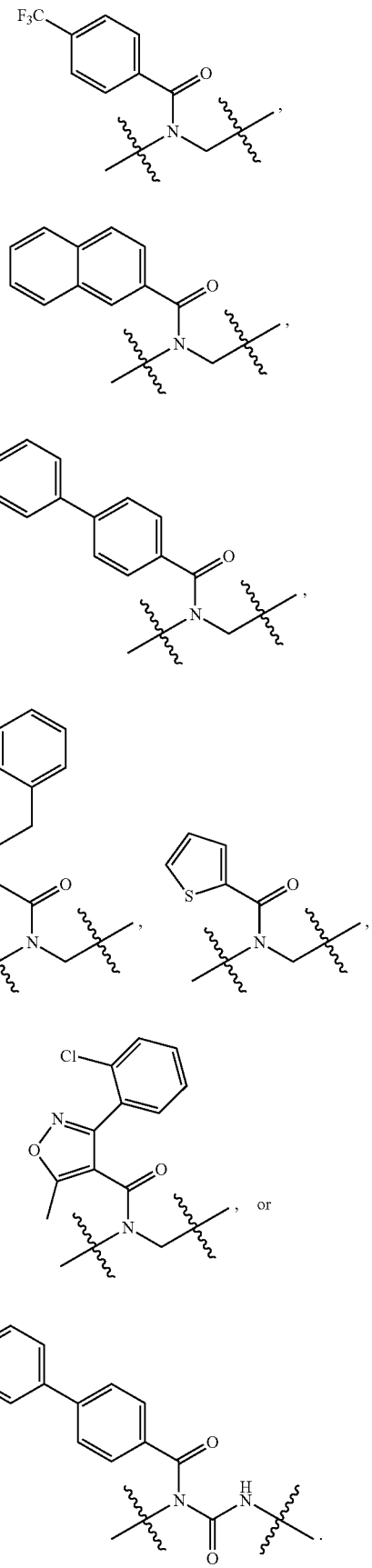

Moreover, in the compounds of formula (I), $B_2$ can be a bond, ethylene, phenylene,

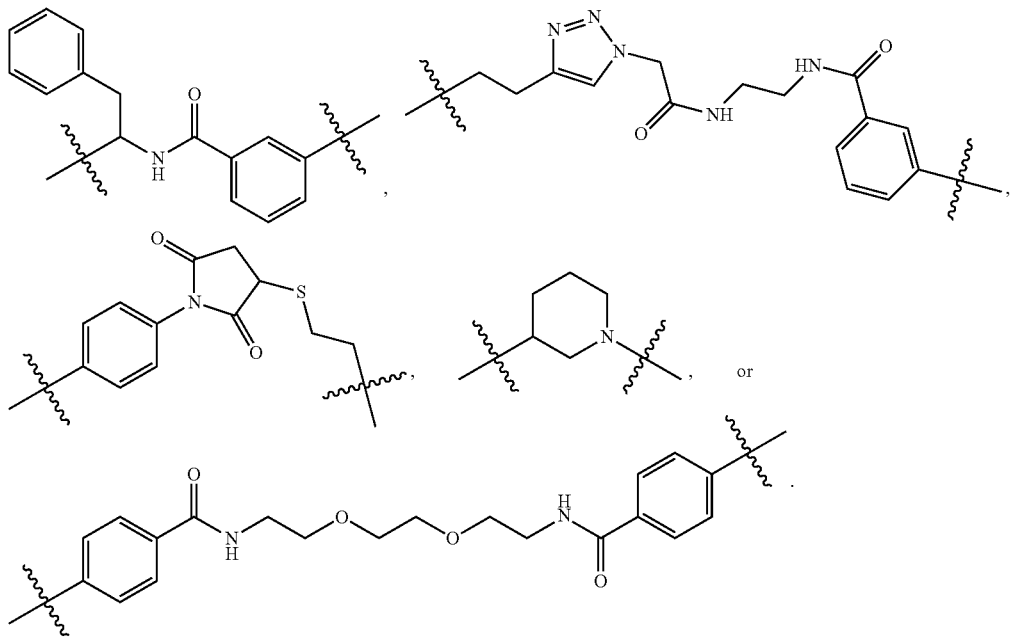

In compounds of formula (I), Z, a therapeutic moiety, is formed from a therapeutic drug. It is connected to $L_2$ via a bond, e.g., an amide bond or an ester or thioester bond. Upon release from formula (I) via enzymatic hydrolysis, Z is converted to a therapeutic drug that exerts a cytotoxic effect, e.g., anti-proliferation.

Preferably, Z is an anticancer therapeutic moiety, an anti-virus therapeutic moiety, an antibiotic therapeutic moiety, an immuno-stimulatory therapeutic moiety, an immuno-suppressive therapeutic moiety, a therapeutic moiety for treating a cardiovascular disease, or a cytotoxic moiety. Examples of Z include, but are not limited to,

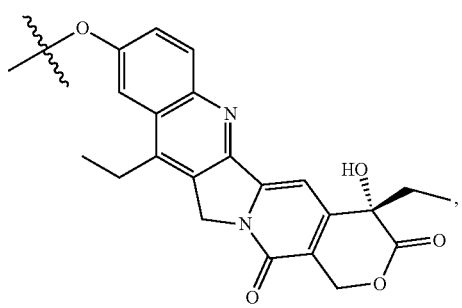

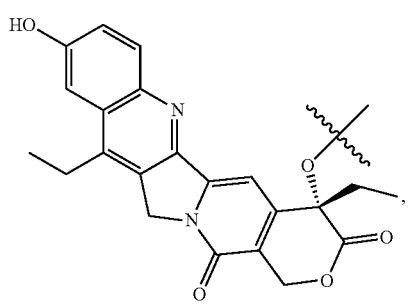

-continued

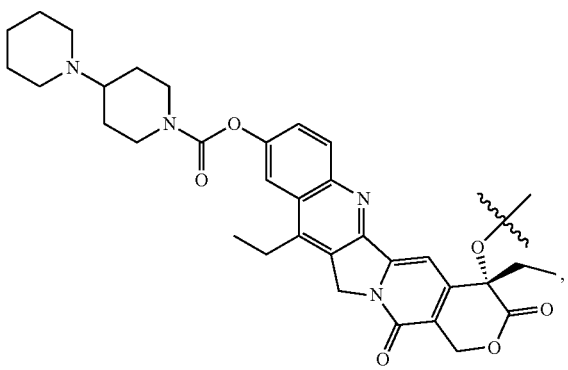

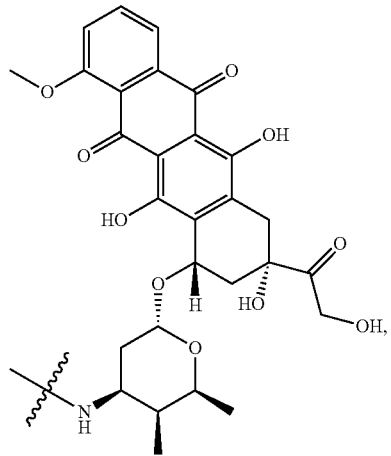

-continued

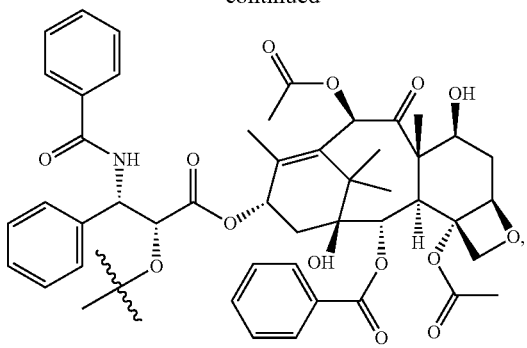

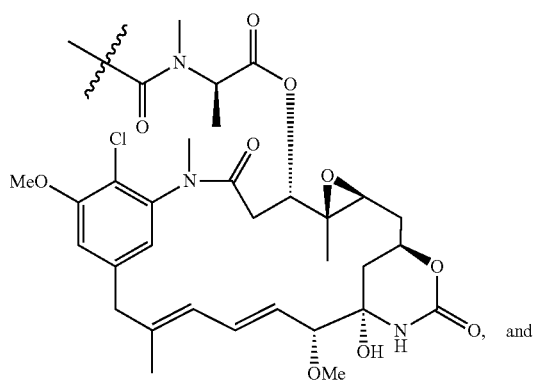

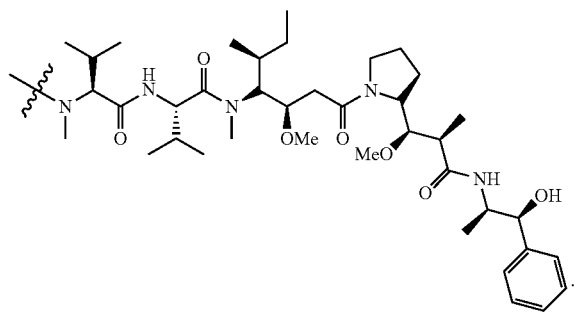

The term "aliphatic" herein refers to a saturated or unsaturated, linear or branched, acyclic, cyclic, or polycyclic hydrocarbon moiety. Examples include, but are not limited to, alkyl, alkylene, alkenyl, alkenylene, alkynyl, alkynylene, cycloalkyl, cycloalkylene, cycloalkenyl, cycloalkenylene, cycloalkynyl, and cycloalkynylene moieties. The term "heteroaliphatic" herein refers to an aliphatic moiety containing at least one heteroatom selected from N, O, P, B, S, Si, Sb, Al, Sn, As, Se, and Ge. The term "haloaliphatic" herein refers to an aliphatic moiety substituted with one or more halogen atoms. The term "alkyl" herein refers to a straight or branched hydrocarbon group, containing 1-20 (e.g., 1-10 and 1-6) carbon atoms. Examples include methyl, ethyl, n-propyl, i-propyl, n-butyl, i-butyl, and t-butyl. The term "alkylene" refers to bivalent alkyl. Examples include —CH$_2$—, —CH$_2$CH$_2$—, —CH$_2$CH$_2$CH$_2$—, —CH$_2$(CH$_3$)CH$_2$—, and —CH$_2$CH$_2$CH$_2$CH$_2$—. The term "haloalkyl" refers to alkyl substituted with one or more halogen (chloro, fluoro, bromo, or idodo) atoms. Examples include trifluoromethyl, bromomethyl, and 4,4,4-trifluorobutyl. The term "haloalkylene" refers to bivalent haloalkyl. The term "heteroalkylene" refers to a bivalent alkyl group, in which one or more carbon atoms are replaced by a heteroatom (e.g., O, N, P, and S). The term "alkoxy" refers to an —O-alkyl group. Examples include methoxy, ethoxy, propoxy, and isopropoxy. The term "haloalkoxy" refers to alkoxy substituted with one or more halogen atoms.

The term "alkenyl" refers to a straight or branched hydrocarbon group, containing 2-20 (e.g., 2-10 and 2-6) carbon atoms and one or more double bonds.

The term "cycloalkyl" refers to a saturated and partially unsaturated monocyclic, bicyclic, tricyclic, or tetracyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl. The term "cycloalkylene" refers to bivalent cycloalkyl.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples of heterocycloalkyl groups include, but are not limited to, piperazinyl, imidazolidinyl, azepanyl, pyrrolidinyl, dihydrothiadiazolyl, dioxanyl, morpholinyl, tetrahydropuranyl, and tetrahydrofuranyl. The term "heterocycloalkylene" refers to bivalent heterocycloalkyl.

The term "aryl" refers to a 6-carbon monocyclic, 10-carbon bicyclic, 14-carbon tricyclic aromatic ring system wherein each ring may have 1 to 5 substituents. Examples of aryl groups include phenyl, naphthyl, and anthracenyl. The term "arylene" refers to bivalent aryl. The term "aralkyl" refers to alkyl substituted with an aryl group. The term "aralkenyl" refers to alkenyl substituted with an aryl group.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl. The term "heteroaralkyl" refers to an alkyl group substituted with a heteroaryl group. The term "heteroaralkenyl" refers to an alkenyl group substituted with a heteroaryl group. The term "heteroarylene" refers to bivalent heteroaryl.

The term "halo" refers to a fluoro, chloro, bromo, or iodo radical. The term "amino" refers to a radical derived from amine, which is unsubstituted or mono-/di-substituted with alkyl, aryl, cycloalkyl, heterocycloalkyl, or heteroaryl. The term "alkylamino" refers to alkyl-NH—. The term "dialkylamino" refers to alkyl-N(alkyl)-.

The term "acyl" refers to —C(O)-alkyl, —C(O)-aryl, —C(O)-cycloalkyl, —C(O)-heterocycloalkyl, or —C(O)-heteroaryl.

Alkyl, cycloalkyl, heterocycloalkyl, aryl, heteroaryl, aralkyl, heteroaralkyl, alkoxy, and aryloxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl cycloalkyl, and heterocycloalkyl may further substituted.

Herein, the term "compound" refers to the compounds described above, as well as their salts, solvates, and metal complexes. A salt can be formed between an anion and a positively charged group (e.g., amino) on a compound; examples of a suitable anion include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group; examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine. A metal complex can be formed of a compound and a metal ion. The metal ion is a cation having two or more charges. The metal complex is typically formed via chelation of a metal ion and a compound of formula (I). Examples of the metal ion include $Zn^{2+}$, $Cu^{2+}$, $Ca^{2+}$, $Mg^{2+}$, $Mn^{2+}$, $Ni^{2+}$, $Co^{2+}$, $Fe^{2+}$, $Cd^{2+}$, and a combination thereof.

This invention also features use of one of the above-described compounds for the manufacture of a medicament for treating PS-related conditions. Thus, this invention also relates to use of such a compound for treating a PS-related condition by administering to a subject in need of the treatment an effective amount of a compound of this invention and an effective amount of one or more other active agents.

Also within the scope of the present invention is a pharmaceutical composition containing a pharmaceutically acceptable carrier and a complex of a metal ion and one of the compounds of formula (I) described above.

The pharmaceutical composition can further contain another therapeutic agent for treating PS-related conditions. Active agents include, but are not limited to, immunomodulatory agents, such as interferons α, β, and γ; antiviral agents such as ribavirin and amantadine; therapeutic agents target in any PS-related conditions. Such an active agent and a compound of this invention may be applied to a subject at two separate times or simultaneously but in two dosage forms. Alternatively, they can be combined in a composition as described above for use as a single dosage form.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active compound can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

Still within the scope of this invention is a method of treating a condition associated with cells containing inside-out phosphatidylserine. In this condition, normally intracellular phosphatidylserine is exposed on the outer surface of the cells. The method includes administering an effective amount of one of the compounds described above to a subject in need thereof. The compound of formula (I) can be administered as a complex formed of the compound and a metal ion having two or more positive charges (e.g., $Zn^{2+}$). The condition exists in viral infection, bacterial infection, inflammatory disease, cancer, misregulation of cell death in organ transplant, misregulation of cell death in neurodegenerative disease, and misregulation of cell death in cardiovascular disease.

The term "treating" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

The details of one or more embodiments of the invention are set forth in the description below. Other features, objects, and advantages of the invention will be apparent from the description and from the claims.

DETAILED DESCRIPTION

Shown below are 51 exemplary compounds synthesized following the procedures described in Examples 1-51 and tested following the procedures described thereafter.

All compounds listed below include their racemates (i.e., equal amounts of left- and right-handed enantiomers of a chiral molecule) unless otherwise specified.

| Compound structures | Compound numbers |
|---|---|
| 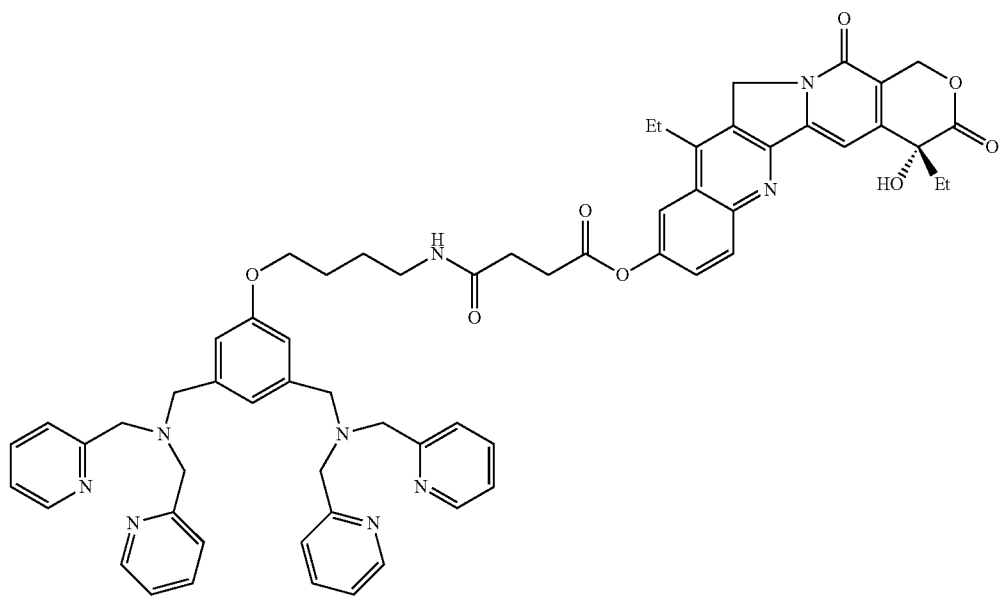 [SMILES: CCc1c2c(nc3ccc(OC(=O)CCC(=O)NCCCCOc4cc(CN(Cc5ccccn5)Cc5ccccn5)cc(CN(Cc5ccccn5)Cc5ccccn5)c4)cc13)-c1cc3c(c(=O)n1C2)COC(=O)[C@@]3(O)CC] | 1 |
| 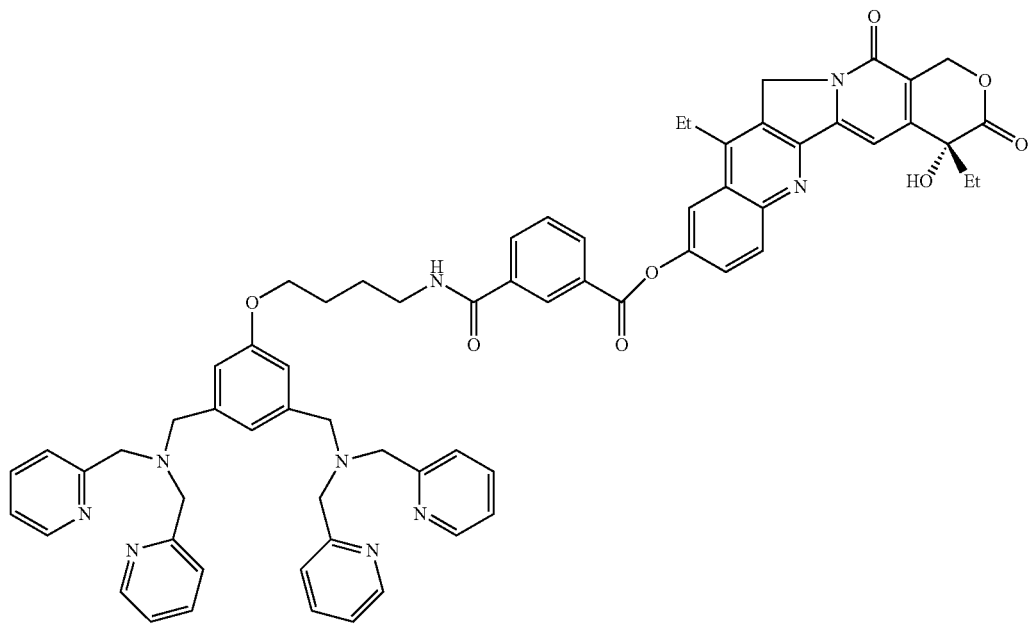 [SMILES: CCc1c2c(nc3ccc(OC(=O)c4cccc(C(=O)NCCCCOc5cc(CN(Cc6ccccn6)Cc6ccccn6)cc(CN(Cc6ccccn6)Cc6ccccn6)c5)c4)cc13)-c1cc3c(c(=O)n1C2)COC(=O)[C@@]3(O)CC] | 2 |

-continued
| Compound structures | Compound numbers |
|---|---|
| 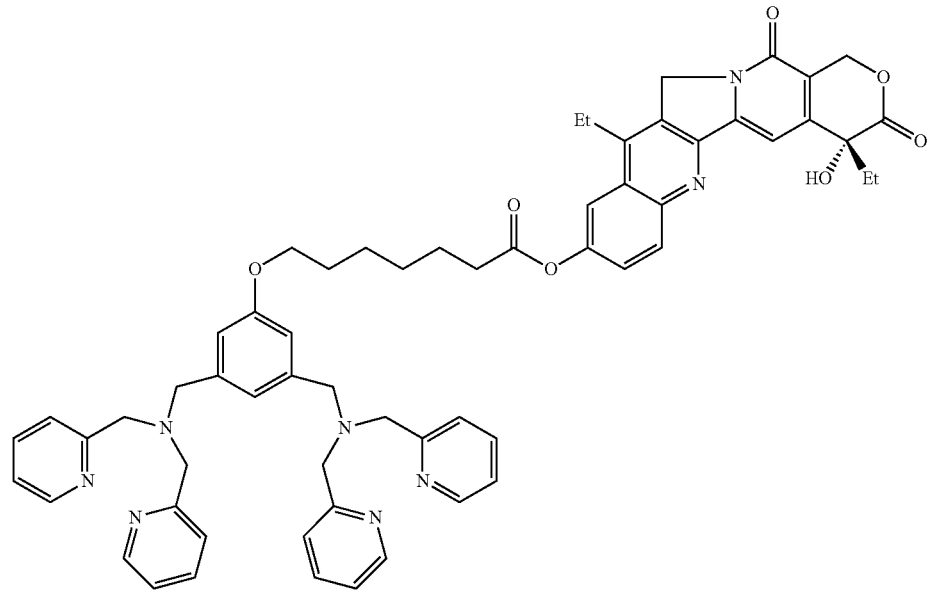 [SMILES: CCc1c2c(nc3ccc(OC(=O)CCCCCCOc4cc(CN(Cc5ccccn5)Cc5ccccn5)cc(CN(Cc5ccccn5)Cc5ccccn5)c4)cc13)-c1cc3c(c(=O)n1C2)COC(=O)[C@@]3(O)CC] | 3 |
| 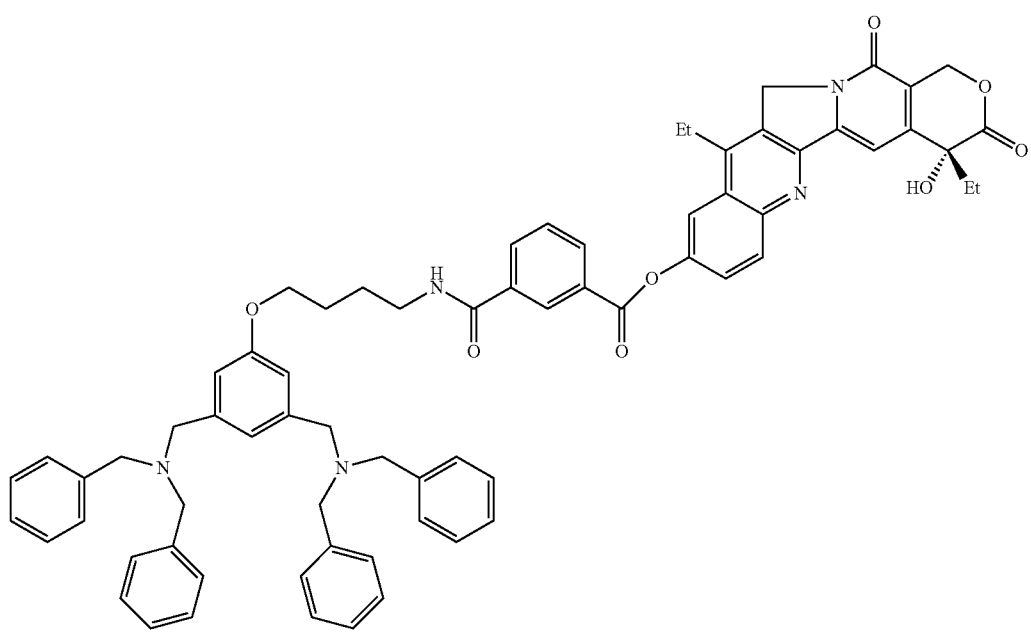 [SMILES: CCc1c2c(nc3ccc(OC(=O)c4cccc(C(=O)NCCCCOc5cc(CN(Cc6ccccc6)Cc6ccccc6)cc(CN(Cc6ccccc6)Cc6ccccc6)c5)c4)cc13)-c1cc3c(c(=O)n1C2)COC(=O)[C@@]3(O)CC] | 4 |

-continued
| Compound structures | Compound numbers |
|---|---|
| 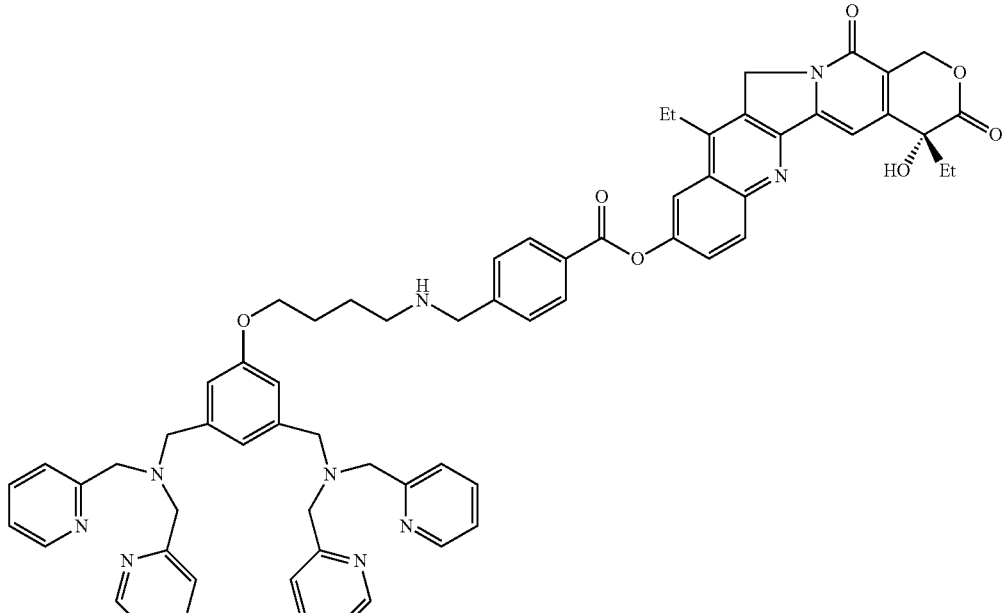 | 5 |
| 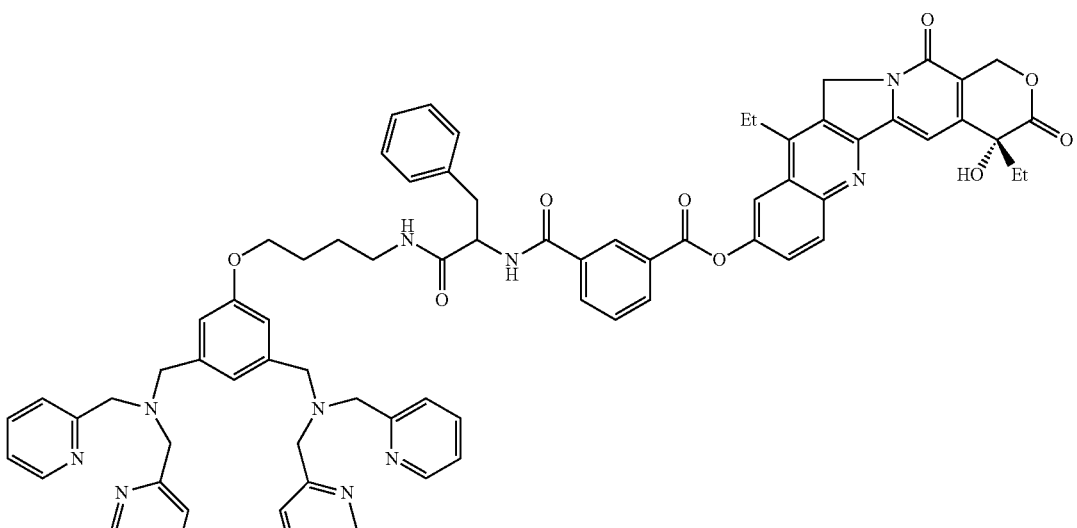 | 6 |

| Compound structures | Compound numbers |
|---|---|
| 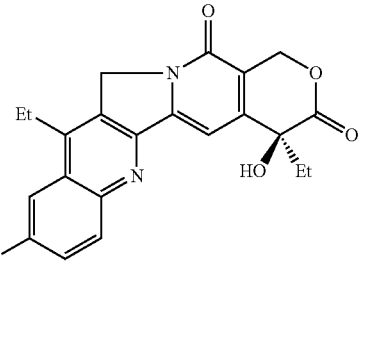 | 7 |
| 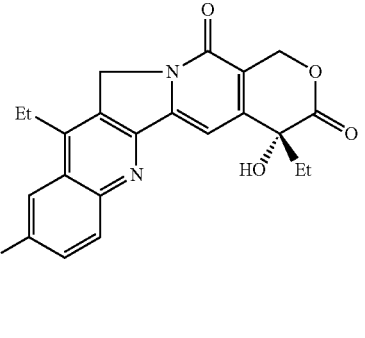 | 8 |

-continued
| Compound structures | Compound numbers |
|---|---|
| 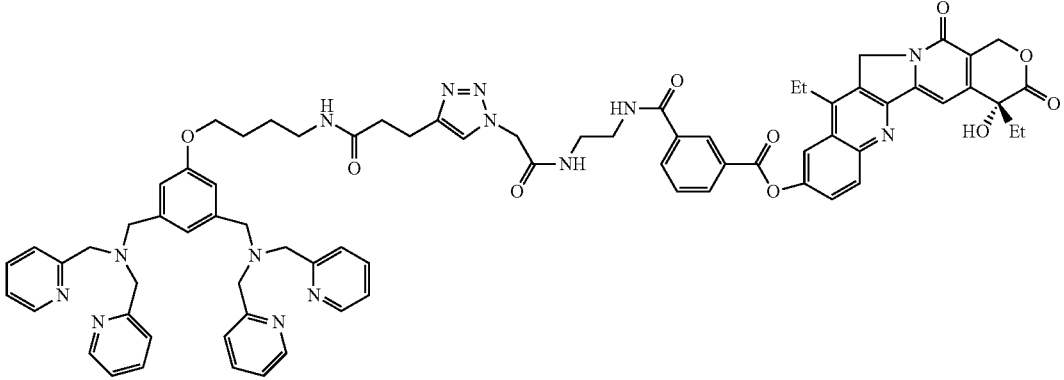 [SMILES: CCc1c2c(nc3ccc(OC(=O)c4cccc(C(=O)NCCNC(=O)Cn5cc(CCC(=O)NCCCCOc6cc(CN(Cc7ccccn7)Cc7ccccn7)cc(CN(Cc7ccccn7)Cc7ccccn7)c6)nn5)c4)cc13)-c1cc3c(c(=O)n1C2)COC(=O)[C@@]3(O)CC] | 9 |
| 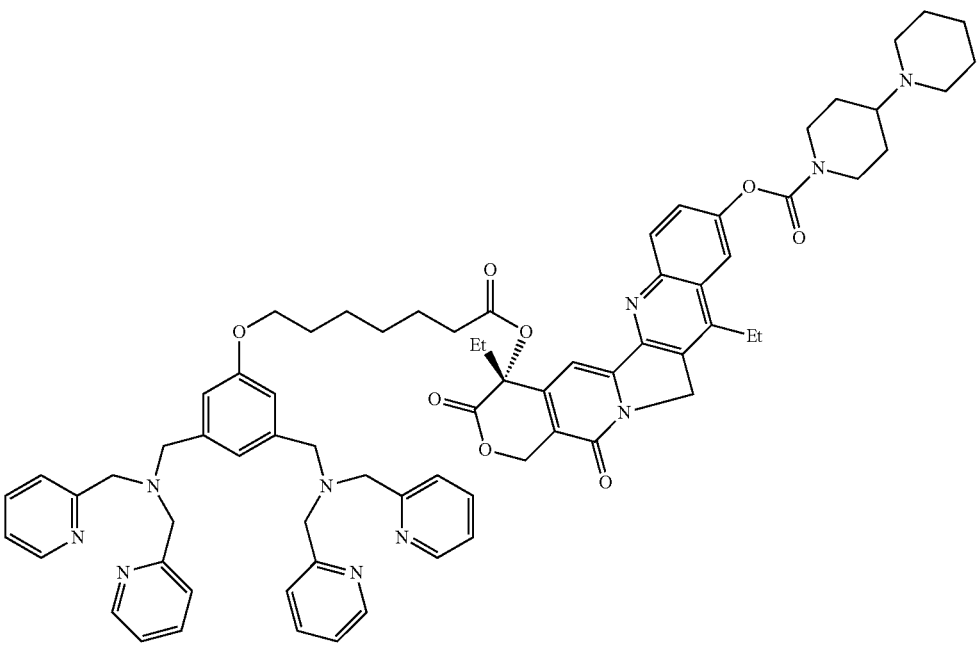 [SMILES: CCc1c2c(nc3ccc(OC(=O)N4CCC(N5CCCCC5)CC4)cc13)-c1cc3c(c(=O)n1C2)COC(=O)[C@]3(CC)OC(=O)CCCCCCOc1cc(CN(Cc2ccccn2)Cc2ccccn2)cc(CN(Cc2ccccn2)Cc2ccccn2)c1] | 10 |

-continued

| Compound structures | Compound numbers |
|---|---|
| 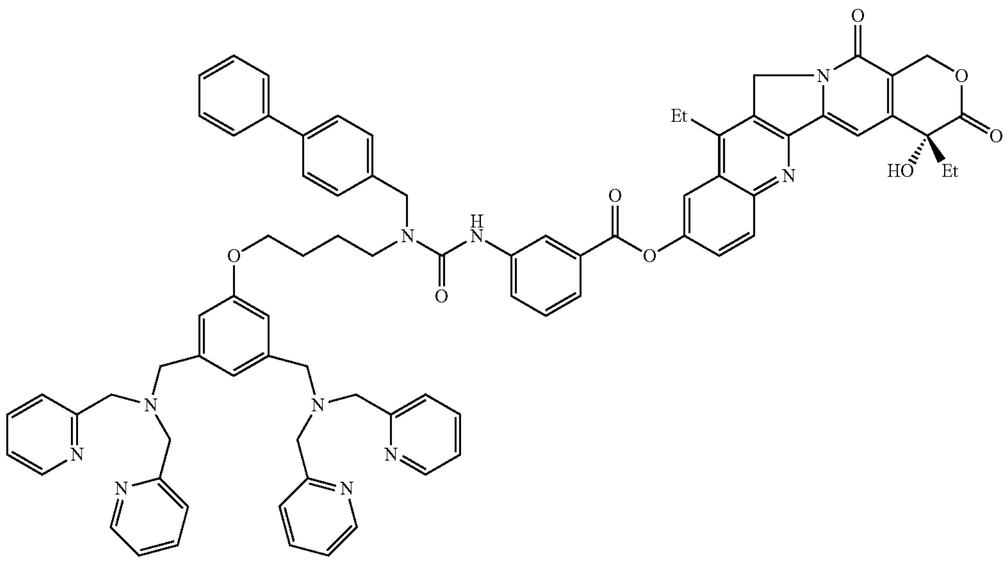 [SMILES: CCc1c2c(nc3ccc(OC(=O)c4cccc(NC(=O)N(CCCCOc5cc(CN(Cc6ccccn6)Cc6ccccn6)cc(CN(Cc6ccccn6)Cc6ccccn6)c5)Cc5ccc(-c6ccccc6)cc5)c4)cc13)-c1cc3c(c(=O)n1C2)COC(=O)[C@@]3(O)CC] | 11 |
| 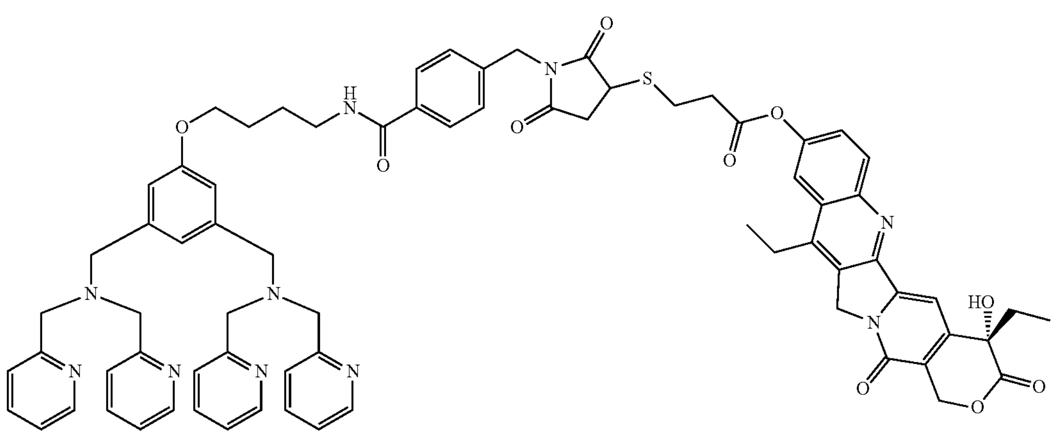 [SMILES: CCc1c2c(nc3ccc(OC(=O)CCSC4CC(=O)N(Cc5ccc(C(=O)NCCCCOc6cc(CN(Cc7ccccn7)Cc7ccccn7)cc(CN(Cc7ccccn7)Cc7ccccn7)c6)cc5)C4=O)cc13)-c1cc3c(c(=O)n1C2)COC(=O)[C@]3(O)CC] | 12 |

| Compound structures | Compound numbers |
|---|---|
| 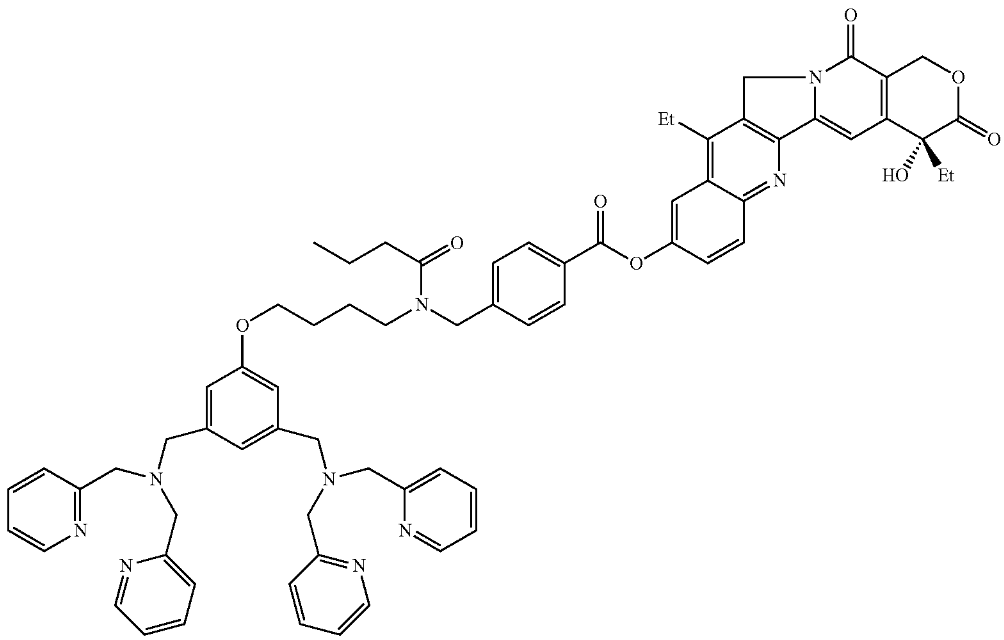 [SMILES: CCCC(=O)N(CCCCOc1cc(CN(Cc2ccccn2)Cc2ccccn2)cc(CN(Cc2ccccn2)Cc2ccccn2)c1)Cc1ccc(C(=O)Oc2ccc3nc4c(c(CC)c3c2)Cn2c-4cc3c(c2=O)COC(=O)[C@@]3(O)CC)cc1] | 13 |
| 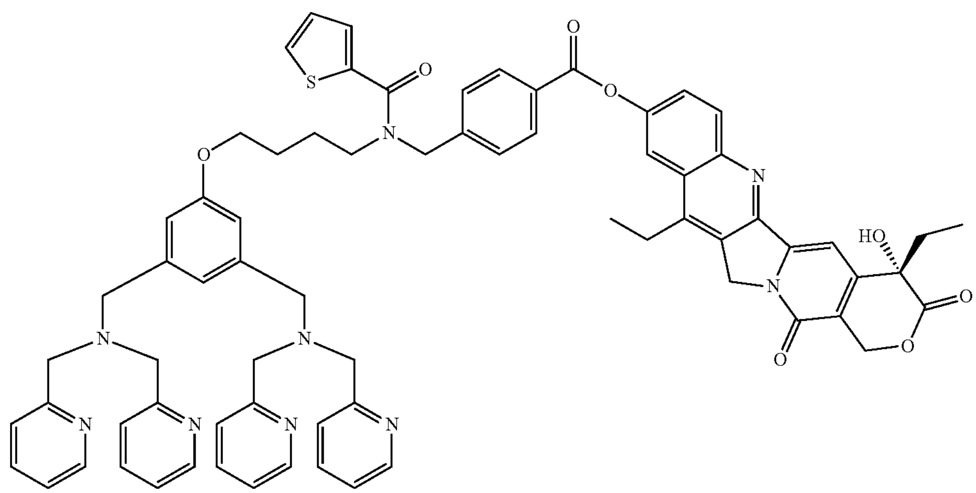 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)C(=O)c5cccs5)cc4)cc13)-c1cc3c(c(=O)n1C2)COC(=O)[C@]3(O)CC] | 14 |

-continued
| Compound structures | Compound numbers |
|---|---|
| 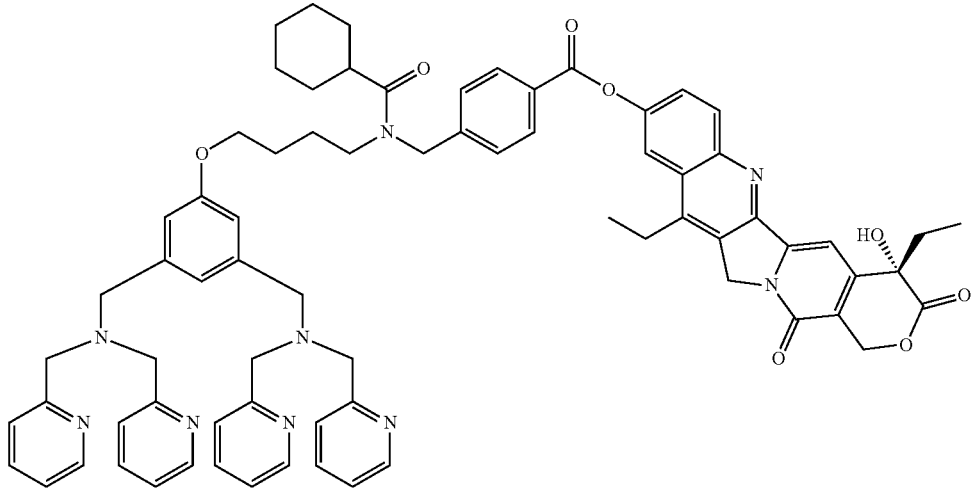 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)C(=O)C5CCCCC5)cc4)cc13)-c1cc3c(c(=O)n1C2)COC(=O)[C@]3(O)CC] | 15 |
| 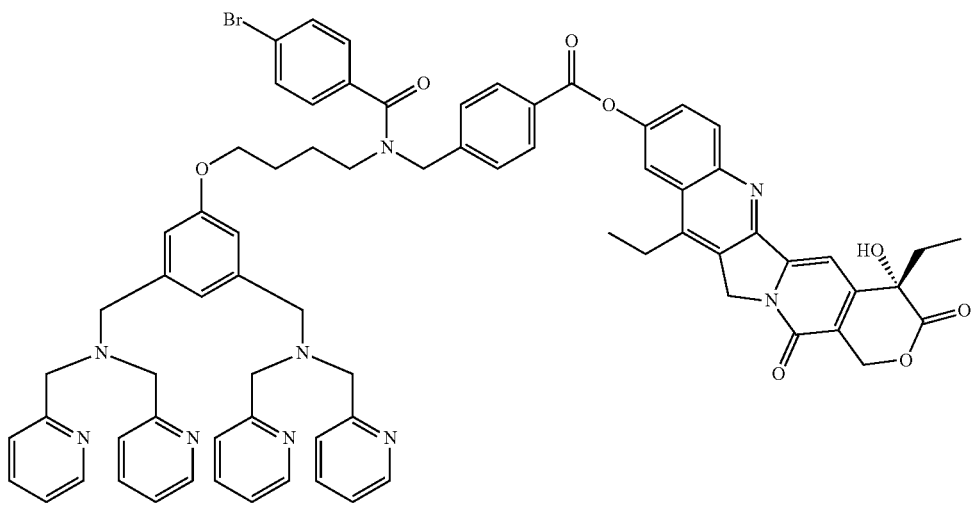 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)C(=O)c5ccc(Br)cc5)cc4)cc13)-c1cc3c(c(=O)n1C2)COC(=O)[C@]3(O)CC] | 16 |
| 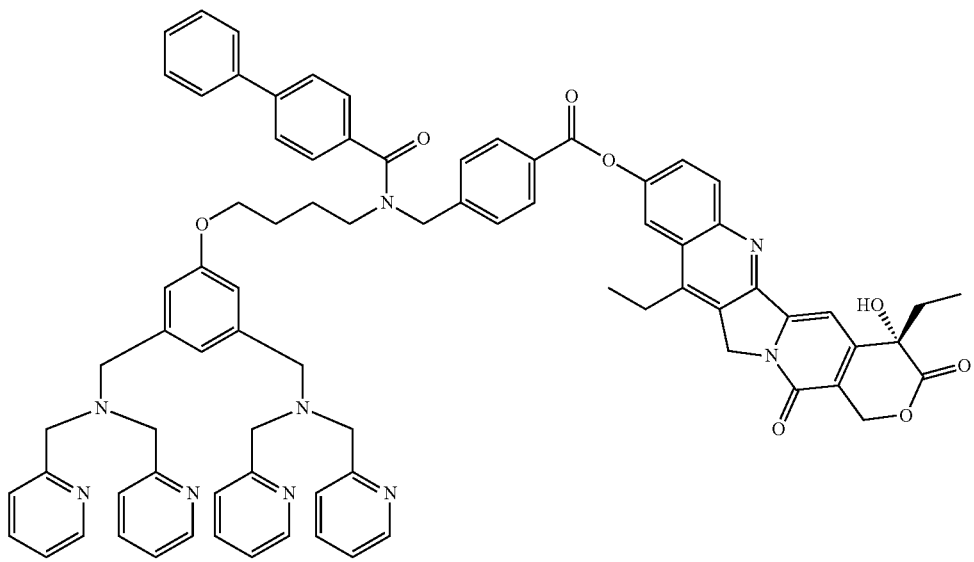 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)C(=O)c5ccc(-c6ccccc6)cc5)cc4)cc13)-c1cc3c(c(=O)n1C2)COC(=O)[C@]3(O)CC] | 17 |

| Compound structures | Compound numbers |
|---|---|
| 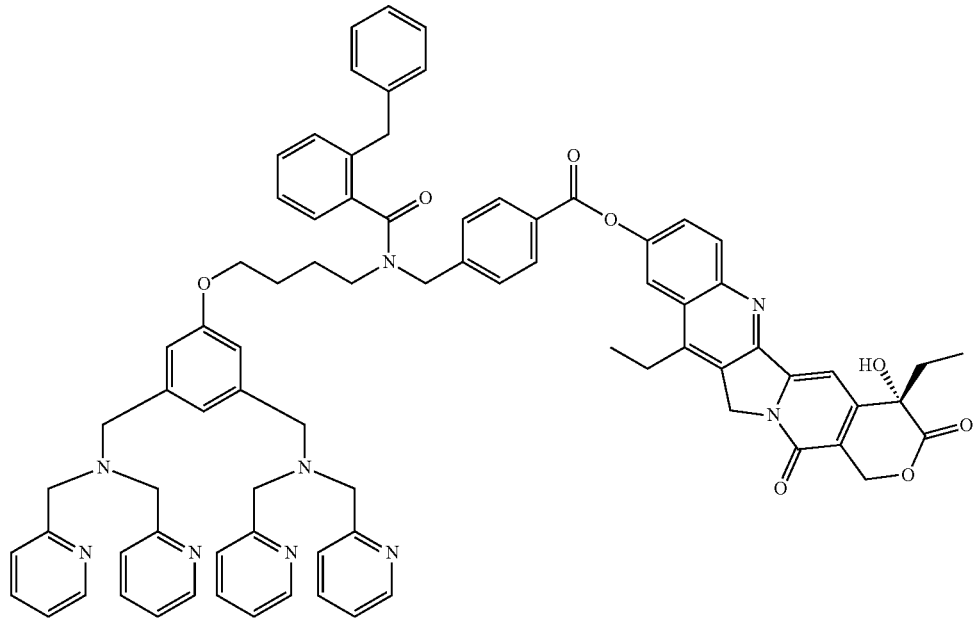 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)C(=O)c5ccccc5Cc5ccccc5)cc4)cc13)-c1cc3c(c(=O)n1C2)COC(=O)[C@]3(O)CC] | 18 |
| 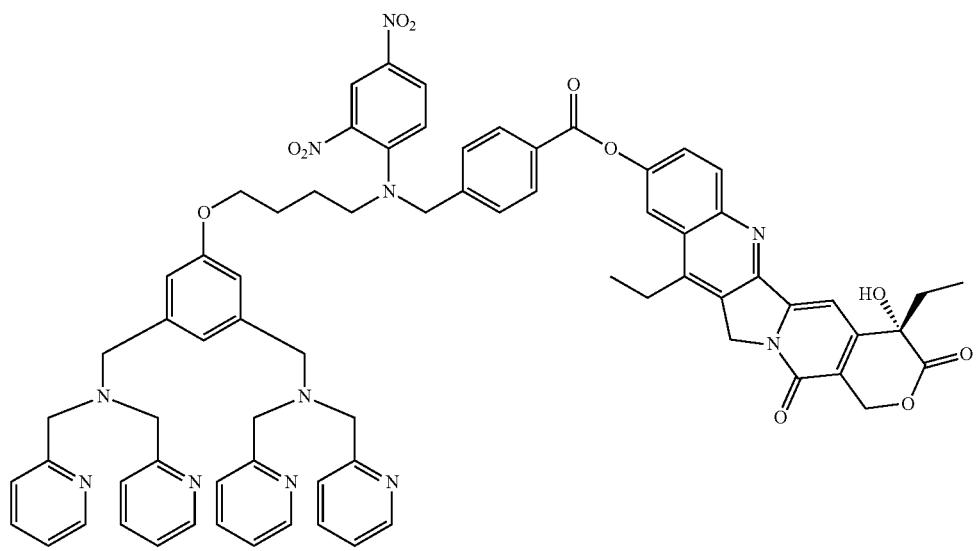 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)c5ccc([N+](=O)[O-])cc5[N+](=O)[O-])cc4)cc13)-c1cc3c(c(=O)n1C2)COC(=O)[C@]3(O)CC] | 19 |

| Compound structures | Compound numbers |
| --- | --- |
| 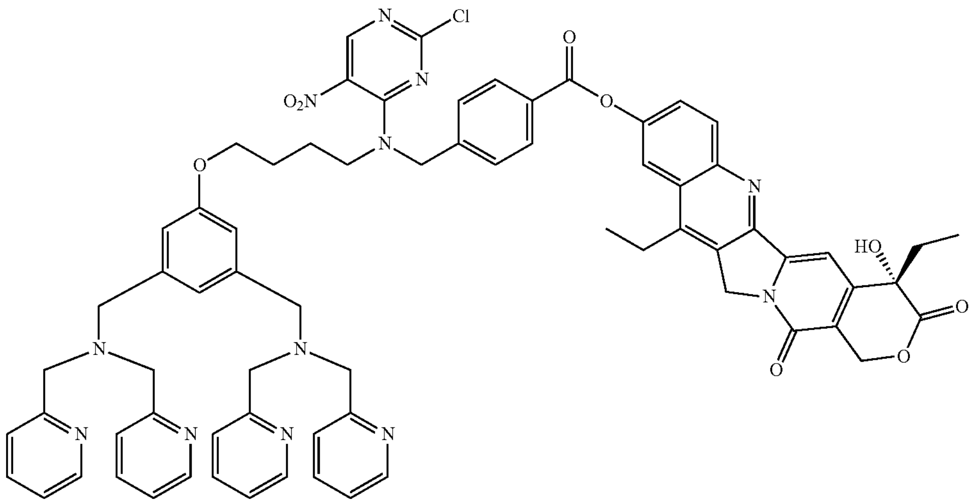 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)c5nc(Cl)ncc5[N+](=O)[O-])cc4)cc13)-c1cc3c(c(=O)n1C2)COC(=O)[C@]3(O)CC] | 20 |
| 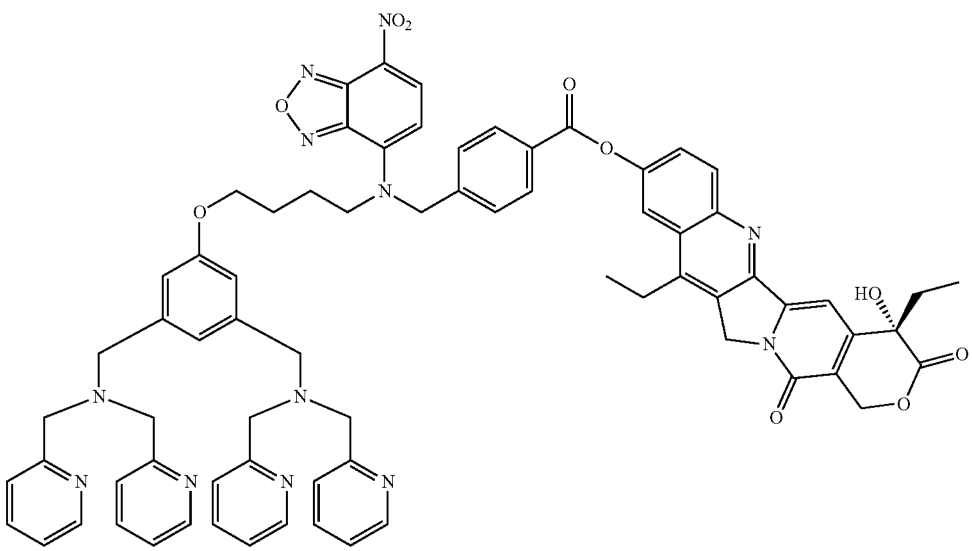 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)c5ccc([N+](=O)[O-])c6nonc56)cc4)cc13)-c1cc3c(c(=O)n1C2)COC(=O)[C@]3(O)CC] | 21 |
| 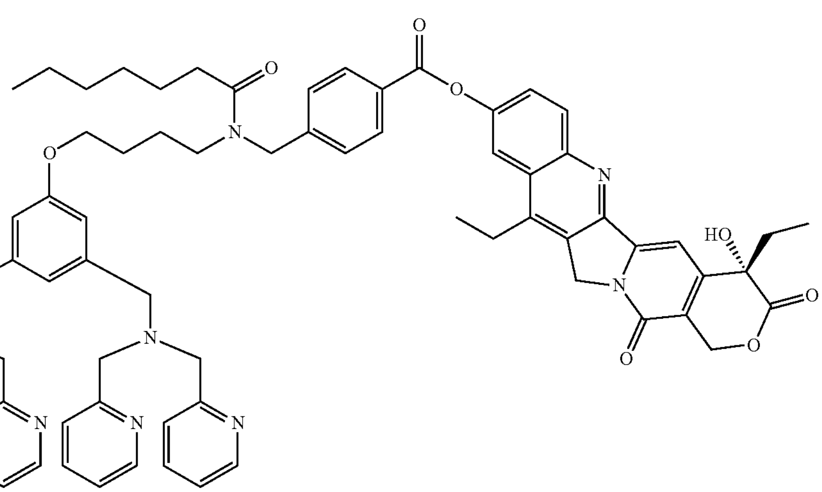 | 22 |

| Compound structures | Compound numbers |
|---|---|
| 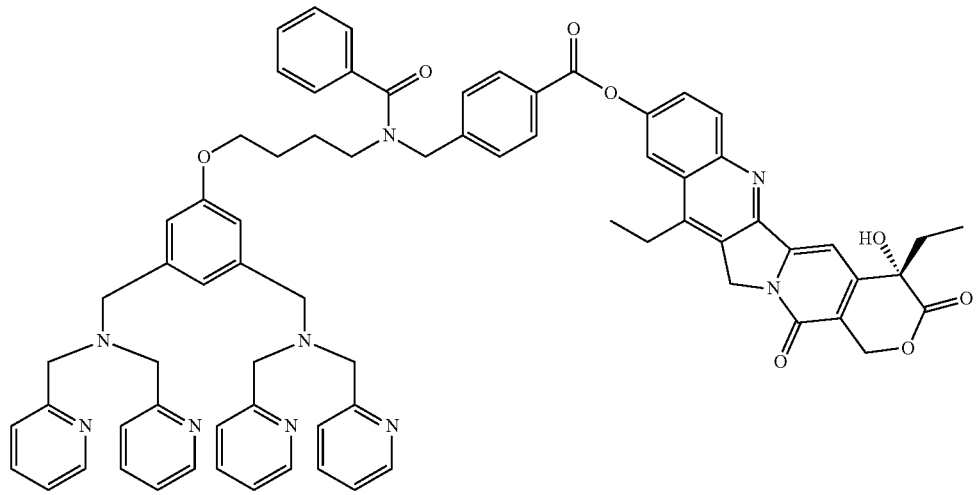 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)C(=O)c5ccccc5)cc4)cc13)-c1cc3c(c(=O)n1C2)COC(=O)[C@]3(O)CC] | 23 |
| 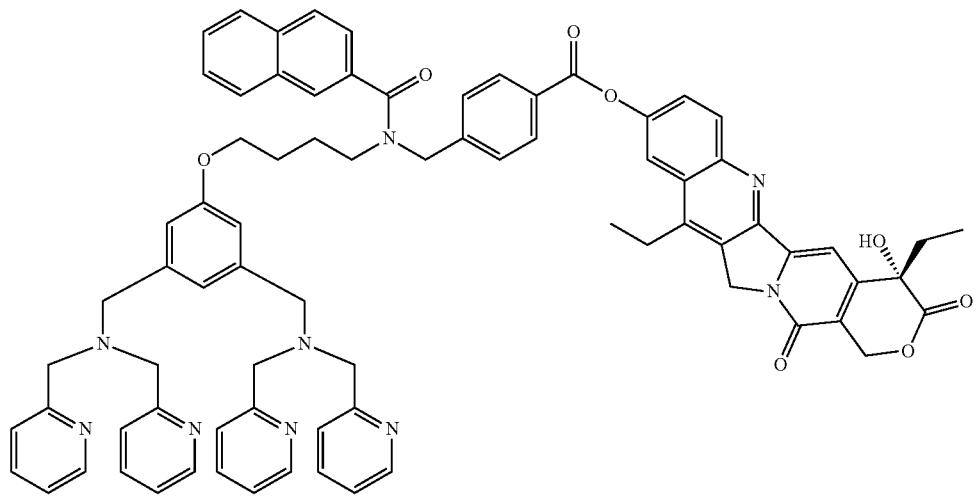 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)C(=O)c5ccc6ccccc6c5)cc4)cc13)-c1cc3c(c(=O)n1C2)COC(=O)[C@]3(O)CC] | 24 |

| Compound structures | Compound numbers |
|---|---|
| 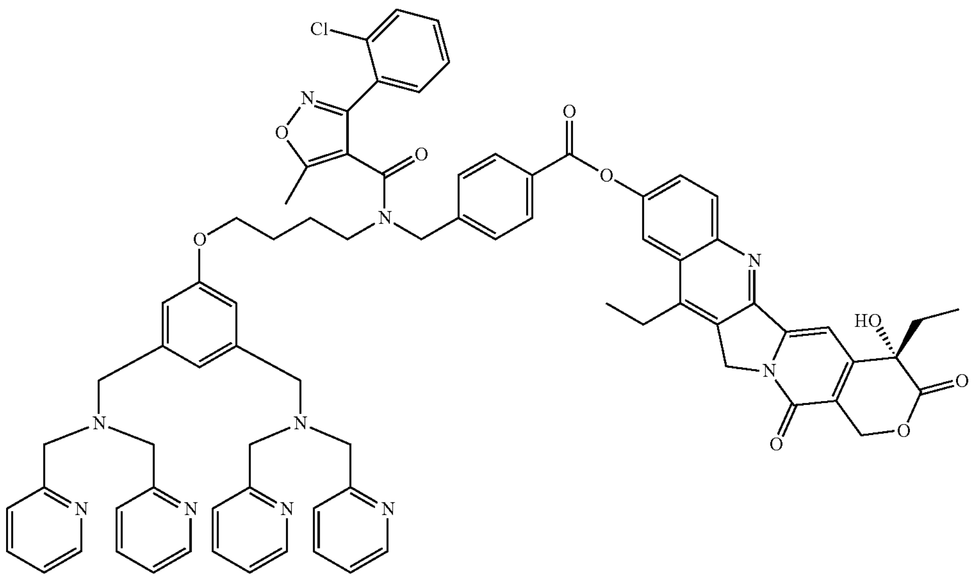 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)C(=O)c5c(-c6ccccc6Cl)noc5C)cc4)cc13)-c1cc3c(c(=O)n1C2)COC(=O)[C@]3(O)CC] | 25 |
| 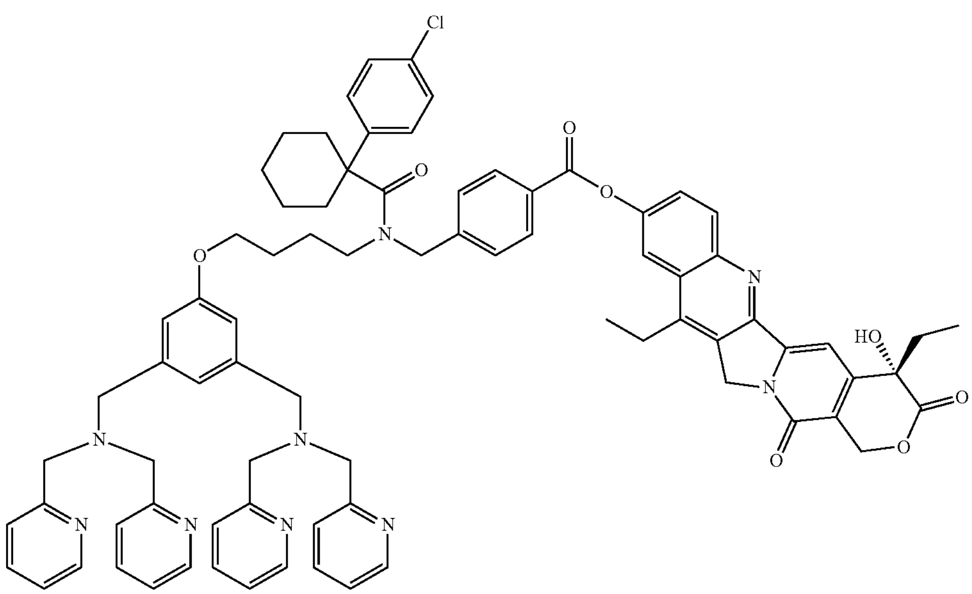 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)C(=O)C5(c6ccc(Cl)cc6)CCCCC5)cc4)cc13)-c1cc3c(c(=O)n1C2)COC(=O)[C@]3(O)CC] | 26 |

-continued
| Compound structures | Compound numbers |
|---|---|
| 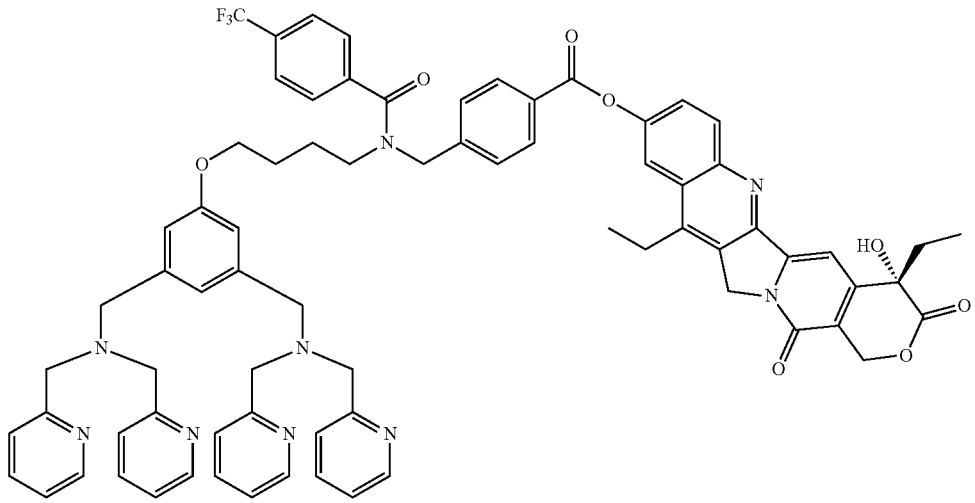 [SMILES: CCc1c2c(nc3ccc(OC(=O)c4ccc(CN(CCCCOc5cc(CN(Cc6ccccn6)Cc6ccccn6)cc(CN(Cc6ccccn6)Cc6ccccn6)c5)C(=O)c5ccc(C(F)(F)F)cc5)cc4)cc13)-c1cc3c(c(=O)n1C2)COC(=O)[C@]3(O)CC] | 27 |
| 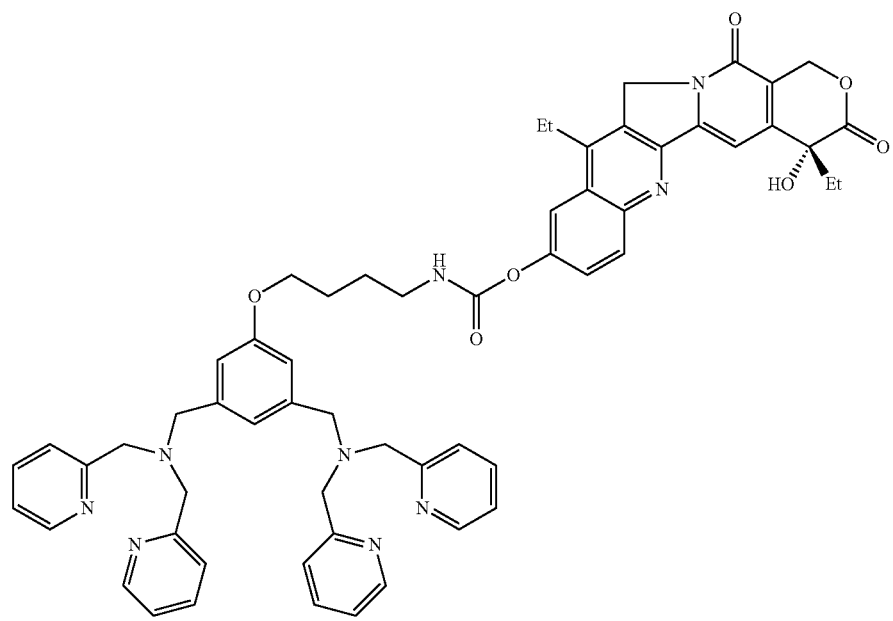 [SMILES: CCc1c2c(nc3ccc(OC(=O)NCCCCOc4cc(CN(Cc5ccccn5)Cc5ccccn5)cc(CN(Cc5ccccn5)Cc5ccccn5)c4)cc13)-c1cc3c(c(=O)n1C2)COC(=O)[C@@]3(O)CC] | 28 |
| 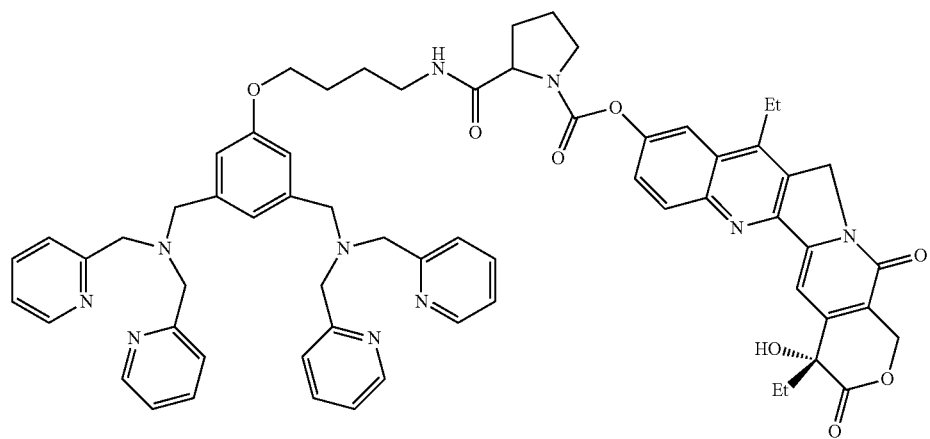 [SMILES: CCc1c2c(nc3ccc(OC(=O)N4CCCC4C(=O)NCCCCOc4cc(CN(Cc5ccccn5)Cc5ccccn5)cc(CN(Cc5ccccn5)Cc5ccccn5)c4)cc13)-c1cc3c(c(=O)n1C2)COC(=O)[C@@]3(O)CC] | 29 |

-continued
| Compound structures | Compound numbers |
|---|---|
| 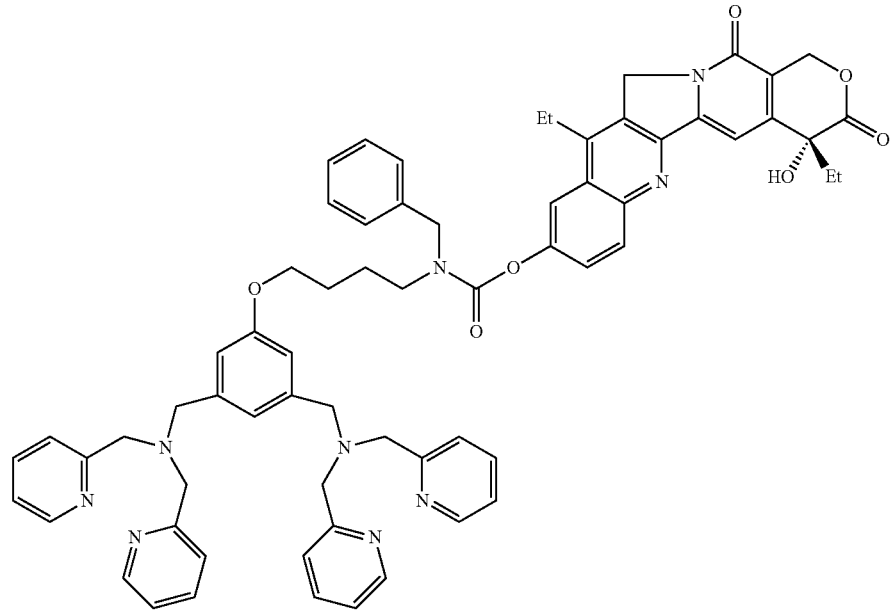 [SMILES: CCc1c2c(nc3ccc(OC(=O)N(CCCCOc4cc(CN(Cc5ccccn5)Cc5ccccn5)cc(CN(Cc5ccccn5)Cc5ccccn5)c4)Cc4ccccc4)cc13)-c1cc3c(c(=O)n1C2)COC(=O)[C@@]3(O)CC] | 30 |
| 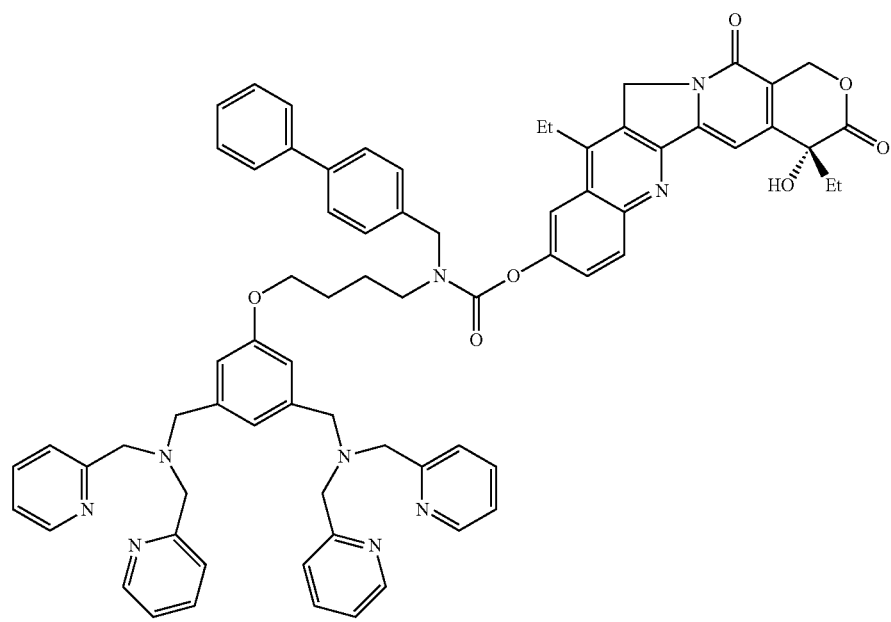 [SMILES: CCc1c2c(nc3ccc(OC(=O)N(CCCCOc4cc(CN(Cc5ccccn5)Cc5ccccn5)cc(CN(Cc5ccccn5)Cc5ccccn5)c4)Cc4ccc(-c5ccccc5)cc4)cc13)-c1cc3c(c(=O)n1C2)COC(=O)[C@@]3(O)CC] | 31 |

-continued
| Compound structures | Compound numbers |
|---|---|
| 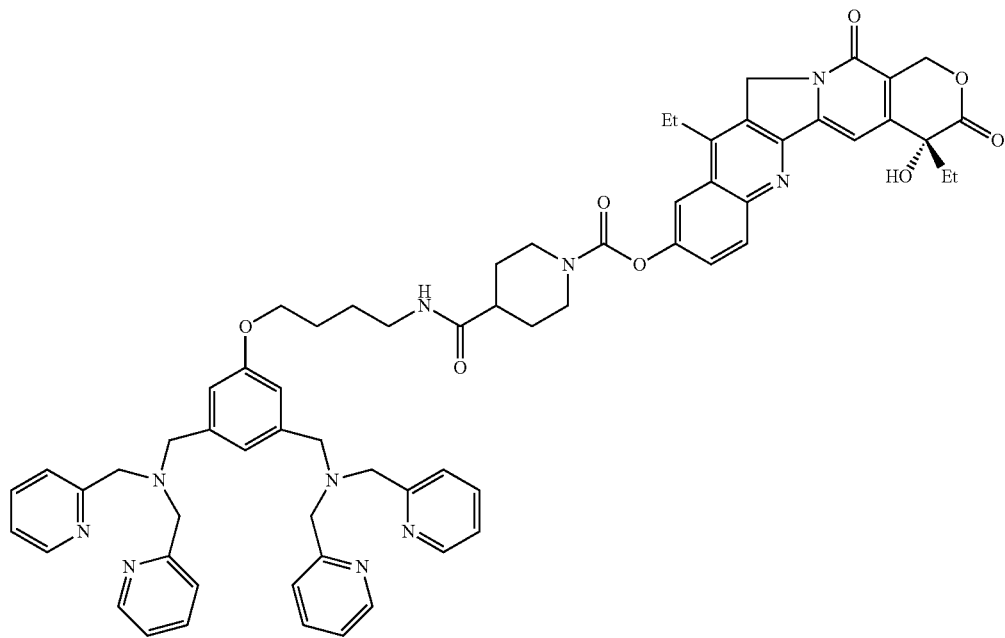 [SMILES: CCc1c2c(nc3ccc(OC(=O)N4CCC(C(=O)NCCCCOc5cc(CN(Cc6ccccn6)Cc6ccccn6)cc(CN(Cc6ccccn6)Cc6ccccn6)c5)CC4)cc13)-c1cc3c(c(=O)n1C2)COC(=O)[C@@]3(O)CC] | 32 |
| 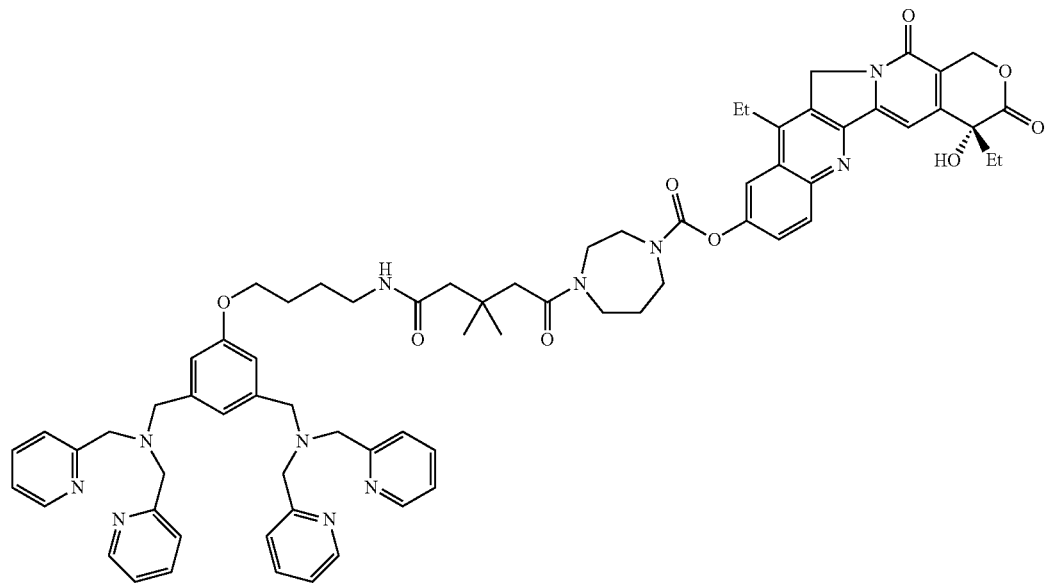 [SMILES: CCc1c2c(nc3ccc(OC(=O)N4CCCN(C(=O)CC(C)(C)CC(=O)NCCCCOc5cc(CN(Cc6ccccn6)Cc6ccccn6)cc(CN(Cc6ccccn6)Cc6ccccn6)c5)CC4)cc13)-c1cc3c(c(=O)n1C2)COC(=O)[C@@]3(O)CC] | 33 |

-continued
| Compound structures | Compound numbers |
|---|---|
| 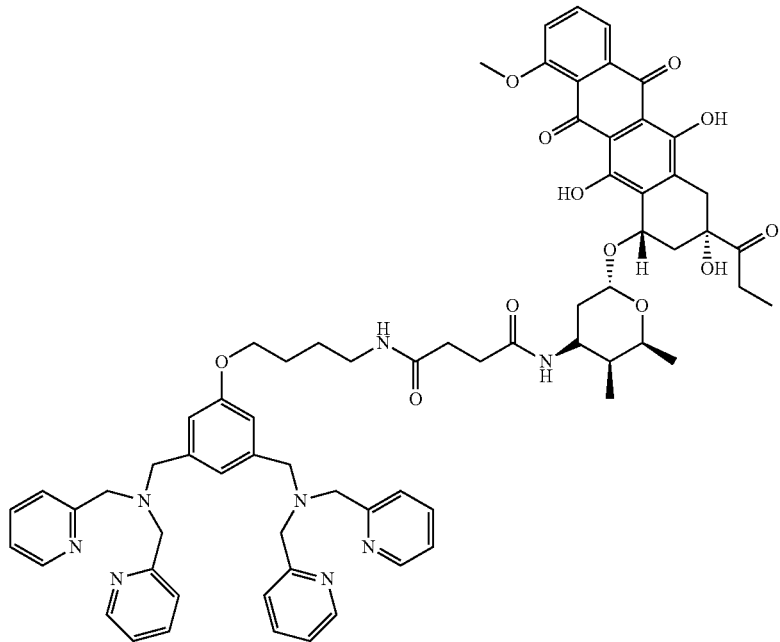 | 34 |
| 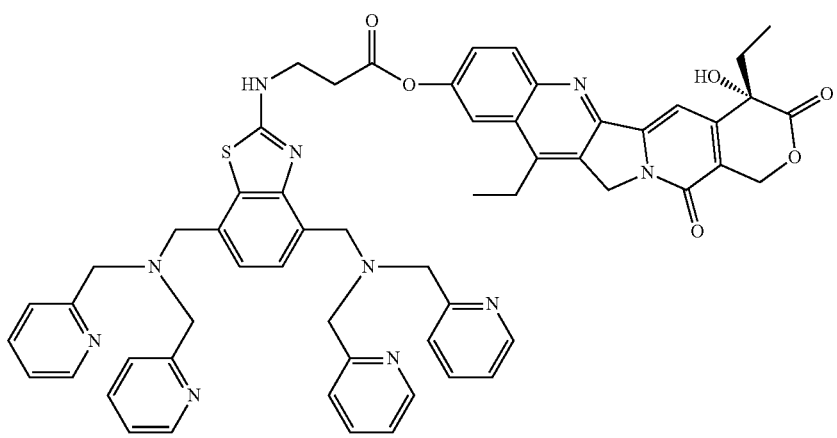 [SMILES: CCc1c2c(nc3ccc(OC(=O)CCNc4nc5c(CN(Cc6ccccn6)Cc6ccccn6)ccc(CN(Cc6ccccn6)Cc6ccccn6)c5s4)cc13)-c1cc3c(c(=O)n1C2)COC(=O)[C@]3(O)CC] | 35 |
| 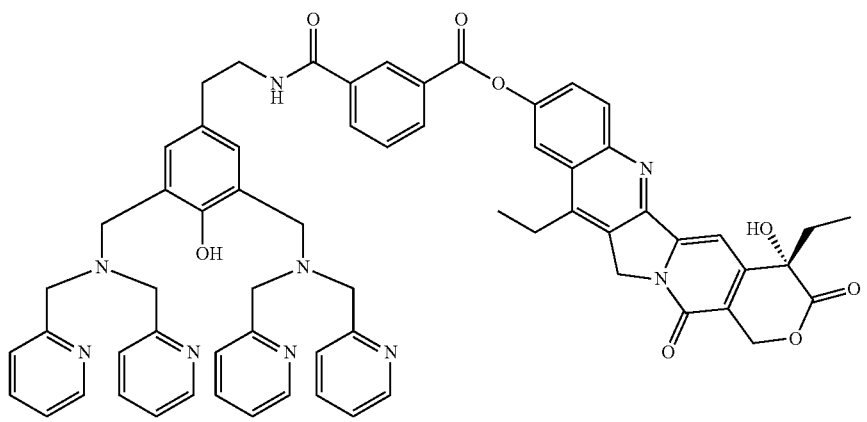 [SMILES: CCc1c2c(nc3ccc(OC(=O)c4cccc(C(=O)NCCc5cc(CN(Cc6ccccn6)Cc6ccccn6)c(O)c(CN(Cc6ccccn6)Cc6ccccn6)c5)c4)cc13)-c1cc3c(c(=O)n1C2)COC(=O)[C@]3(O)CC] | 36 |

| Compound structures | Compound numbers |
|---|---|
| 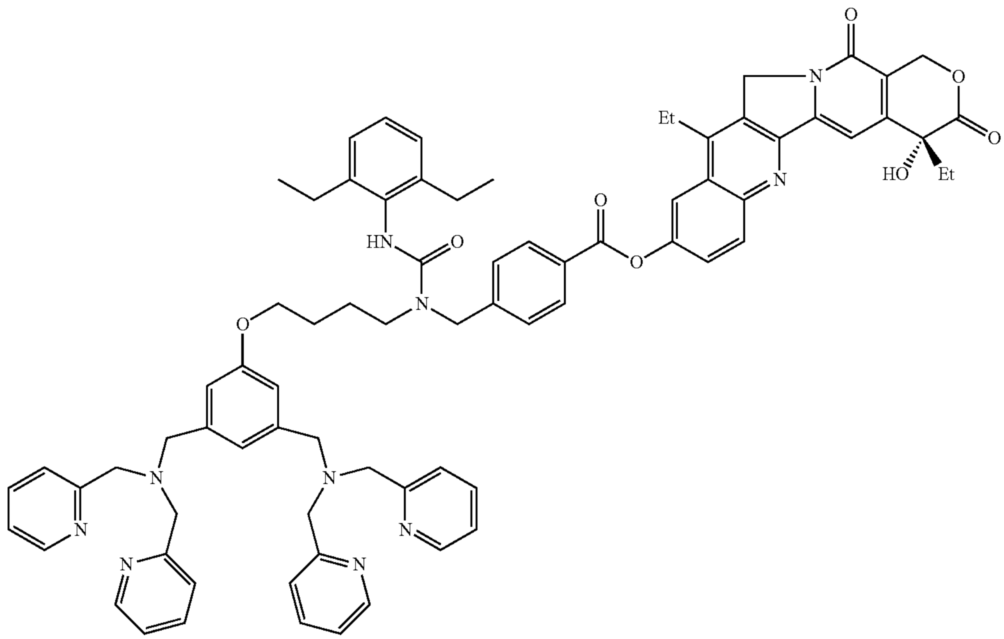 [SMILES: CCc1cccc(CC)c1NC(=O)N(CCCCOc1cc(CN(Cc2ccccn2)Cc2ccccn2)cc(CN(Cc2ccccn2)Cc2ccccn2)c1)Cc1ccc(C(=O)Oc2ccc3nc4c(c(CC)c3c2)Cn2c-4cc3c(c2=O)COC(=O)[C@@]3(O)CC)cc1] | 37 |
| 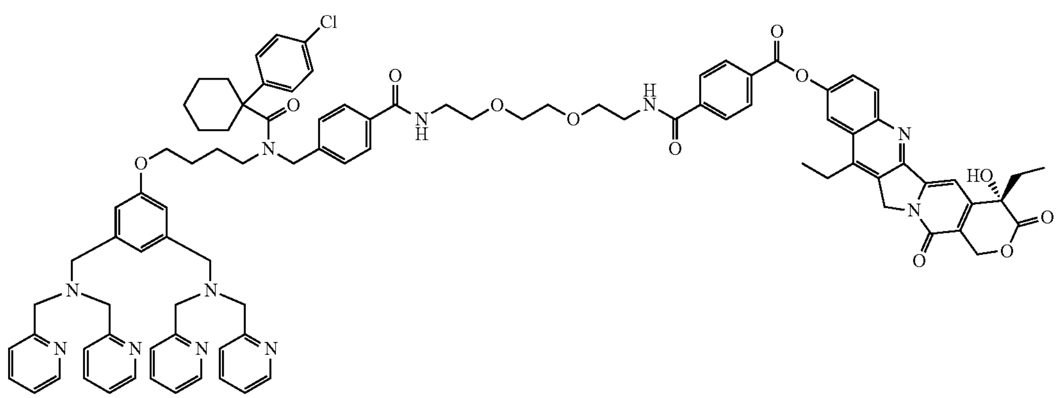 [SMILES: CCc1c2c(nc3ccc(OC(=O)c4ccc(C(=O)NCCOCCOCCNC(=O)c5ccc(CN(CCCCOc6cc(CN(Cc7ccccn7)Cc7ccccn7)cc(CN(Cc7ccccn7)Cc7ccccn7)c6)C(=O)C6(c7ccc(Cl)cc7)CCCCC6)cc5)cc4)cc13)-c1cc3c(c(=O)n1C2)COC(=O)[C@]3(O)CC] | 38 |
| 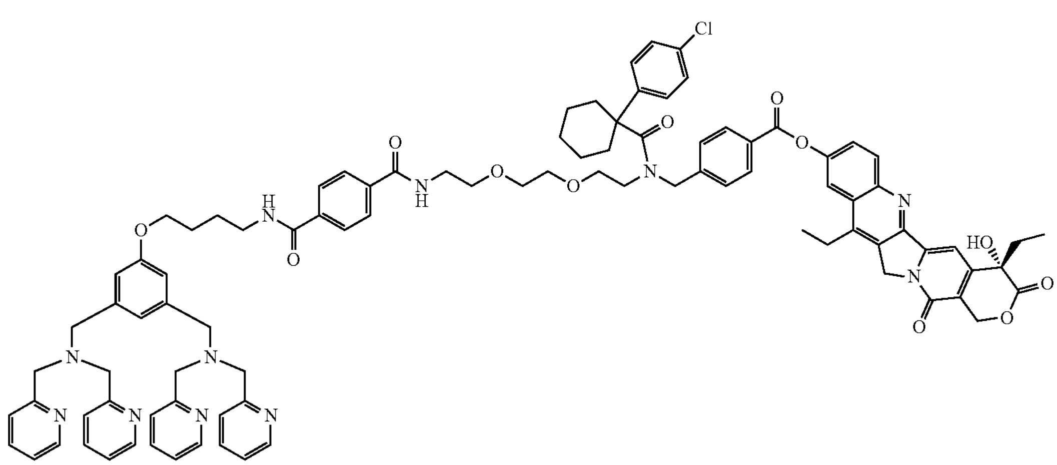 [SMILES: CCc1c2c(nc3ccc(OC(=O)c4ccc(CN(CCOCCOCCNC(=O)c5ccc(C(=O)NCCCCOc6cc(CN(Cc7ccccn7)Cc7ccccn7)cc(CN(Cc7ccccn7)Cc7ccccn7)c6)cc5)C(=O)C5(c6ccc(Cl)cc6)CCCCC5)cc4)cc13)-c1cc3c(c(=O)n1C2)COC(=O)[C@]3(O)CC] | 39 |

| Compound structures | Compound numbers |
|---|---|
| 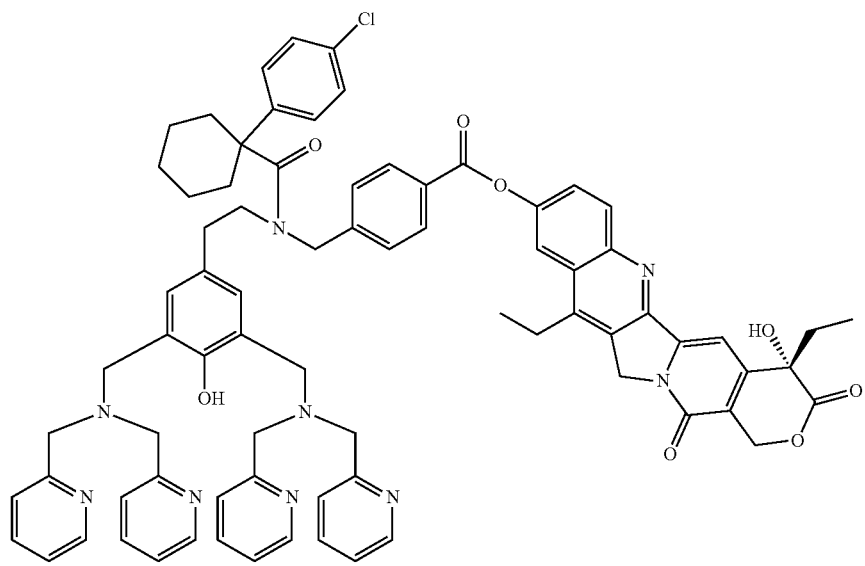 [SMILES: CCc1c2c(nc3ccc(OC(=O)c4ccc(CN(CCc5cc(CN(Cc6ccccn6)Cc6ccccn6)c(O)c(CN(Cc6ccccn6)Cc6ccccn6)c5)C(=O)C5(c6ccc(Cl)cc6)CCCCC5)cc4)cc13)-c1cc3c(c(=O)n1C2)COC(=O)[C@]3(O)CC] | 40 |
| 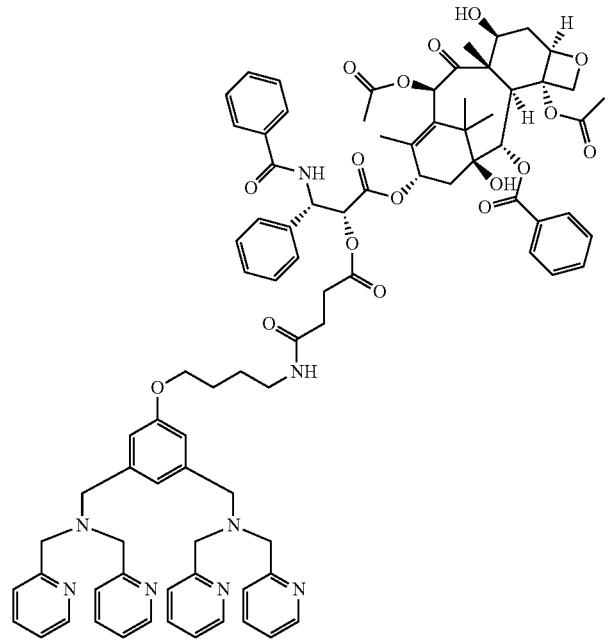 [SMILES: CC(=O)O[C@H]1C(=O)[C@@]2(C)[C@H]([C@H](OC(=O)c3ccccc3)[C@]3(O)C[C@H](OC(=O)[C@H](OC(=O)CCC(=O)NCCCCOc4cc(CN(Cc5ccccn5)Cc5ccccn5)cc(CN(Cc5ccccn5)Cc5ccccn5)c4)[C@@H](NC(=O)c4ccccc4)c4ccccc4)C(C)=C1C3(C)C)[C@]1(OC(C)=O)CO[C@@H]1C[C@@H]2O] | 41 |

-continued

| Compound structures | Compound numbers |
|---|---|
| 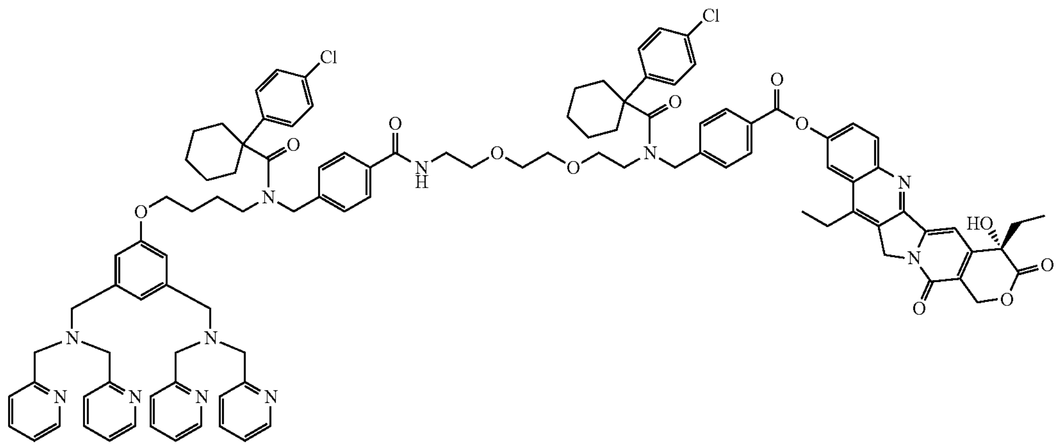 [SMILES: CCc1c2c(nc3ccc(OC(=O)c4ccc(CN(CCOCCOCCNC(=O)c5ccc(CN(CCCCOc6cc(CN(Cc7ccccn7)Cc7ccccn7)cc(CN(Cc7ccccn7)Cc7ccccn7)c6)C(=O)C6(c7ccc(Cl)cc7)CCCCC6)cc5)C(=O)C5(c6ccc(Cl)cc6)CCCCC5)cc4)cc13)-c1cc3c(c(=O)n1C2)COC(=O)[C@]3(O)CC] | 42 |
| 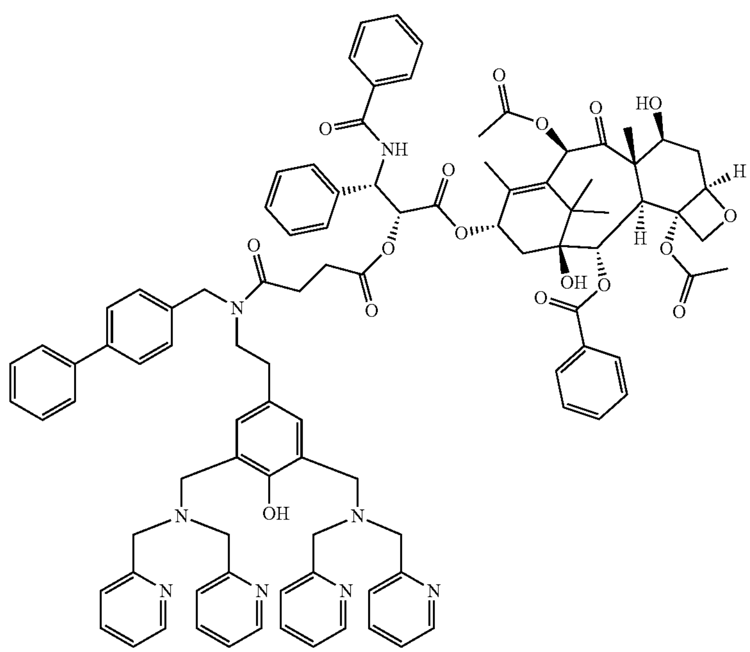 [SMILES: CC(=O)O[C@H]1C(=O)[C@@]2(C)[C@H]([C@H](OC(=O)c3ccccc3)[C@]3(O)C[C@H](OC(=O)[C@H](OC(=O)CCC(=O)N(CCc4cc(CN(Cc5ccccn5)Cc5ccccn5)c(O)c(CN(Cc5ccccn5)Cc5ccccn5)c4)Cc4ccc(-c5ccccc5)cc4)[C@@H](NC(=O)c4ccccc4)c4ccccc4)C(C)=C1C3(C)C)[C@]1(OC(C)=O)CO[C@@H]1C[C@@H]2O] | 43 |

| Compound structures | Compound numbers |
|---|---|
| 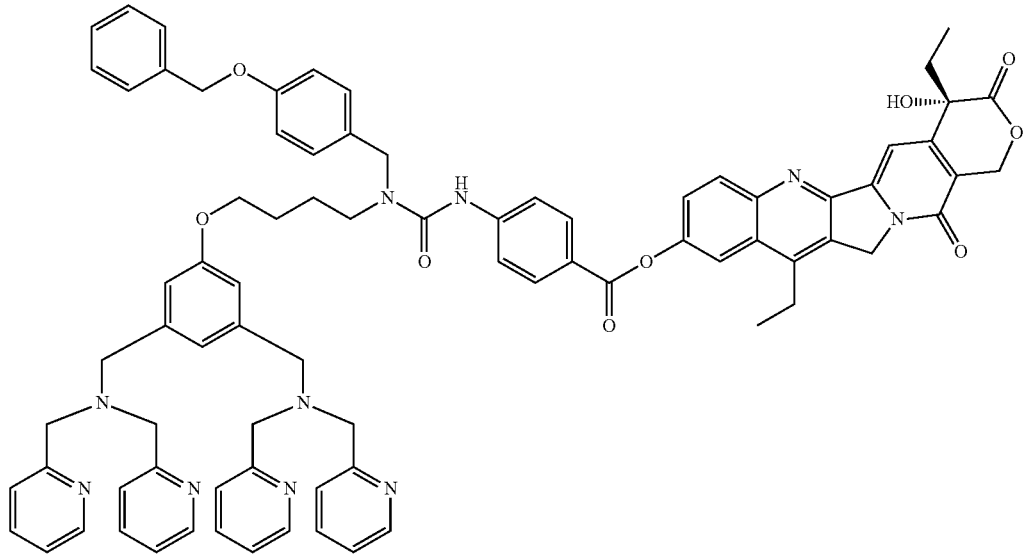 [SMILES: CCc1c2c(nc3ccc(OC(=O)c4ccc(NC(=O)N(CCCCOc5cc(CN(Cc6ccccn6)Cc6ccccn6)cc(CN(Cc6ccccn6)Cc6ccccn6)c5)Cc5ccc(OCc6ccccc6)cc5)cc4)cc13)-c1cc3c(c(=O)n1C2)COC(=O)[C@]3(O)CC] | 44 |
| 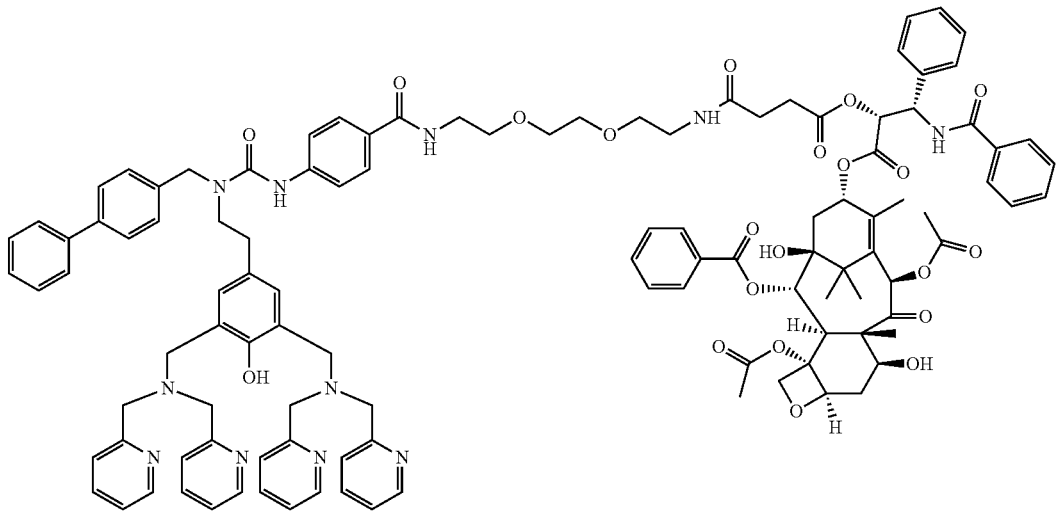 [SMILES: CC(=O)O[C@H]1C(=O)[C@@]2(C)[C@H]([C@H](OC(=O)c3ccccc3)[C@]3(O)C[C@H](OC(=O)[C@H](OC(=O)CCC(=O)NCCOCCOCCNC(=O)c4ccc(NC(=O)N(CCc5cc(CN(Cc6ccccn6)Cc6ccccn6)c(O)c(CN(Cc6ccccn6)Cc6ccccn6)c5)Cc5ccc(-c6ccccc6)cc5)cc4)[C@@H](NC(=O)c4ccccc4)c4ccccc4)C(C)=C1C3(C)C)[C@]1(OC(C)=O)CO[C@@H]1C[C@@H]2O] | 45 |

-continued
| Compound structures | Compound numbers |
|---|---|
| 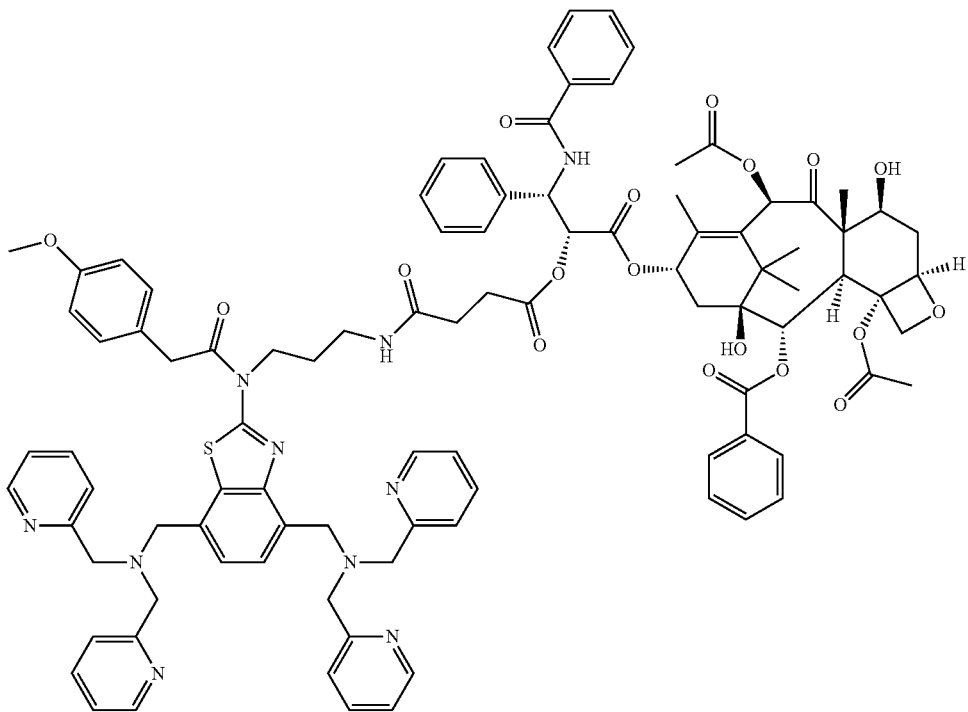 [SMILES: COc1ccc(CC(=O)N(CCCNC(=O)CCC(=O)O[C@@H](C(=O)O[C@H]2C[C@@]3(O)[C@@H](OC(=O)c4ccccc4)[C@@H]4[C@]5(OC(C)=O)CO[C@@H]5C[C@H](O)[C@@]4(C)C(=O)[C@H](OC(C)=O)C(=C2C)C3(C)C)[C@@H](NC(=O)c2ccccc2)c2ccccc2)c2nc3c(CN(Cc4ccccn4)Cc4ccccn4)ccc(CN(Cc4ccccn4)Cc4ccccn4)c3s2)cc1] | 46 |
| 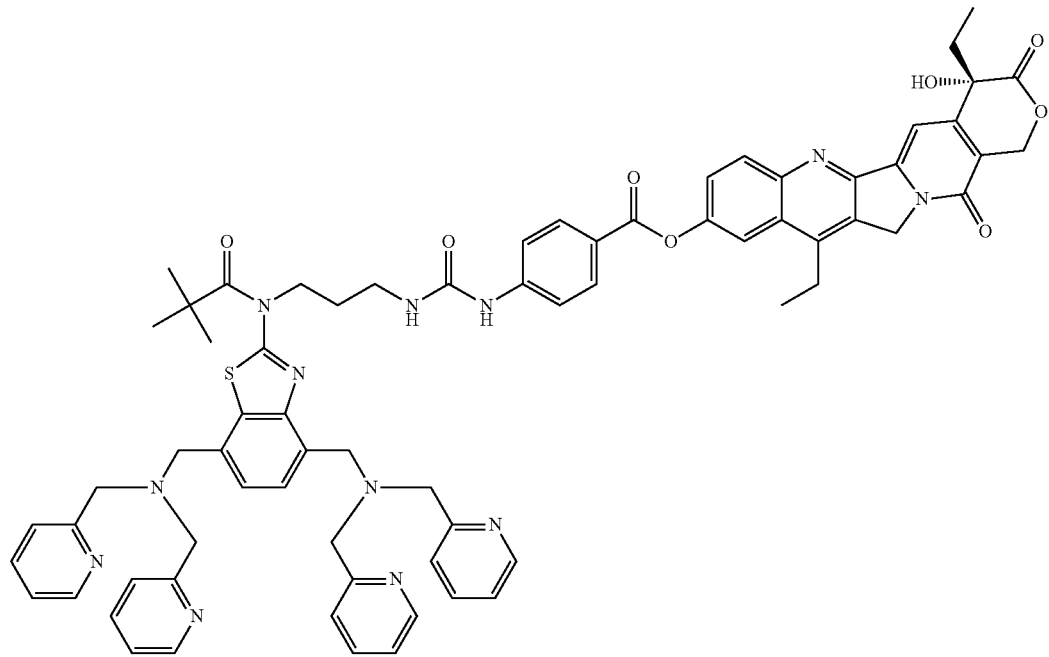 [SMILES: CCc1c2c(nc3ccc(OC(=O)c4ccc(NC(=O)NCCCN(C(=O)C(C)(C)C)c5nc6c(CN(Cc7ccccn7)Cc7ccccn7)ccc(CN(Cc7ccccn7)Cc7ccccn7)c6s5)cc4)cc13)-c1cc3c(c(=O)n1C2)COC(=O)[C@]3(O)CC] | 47 |

-continued
| Compound structures | Compound numbers |
|---|---|
| 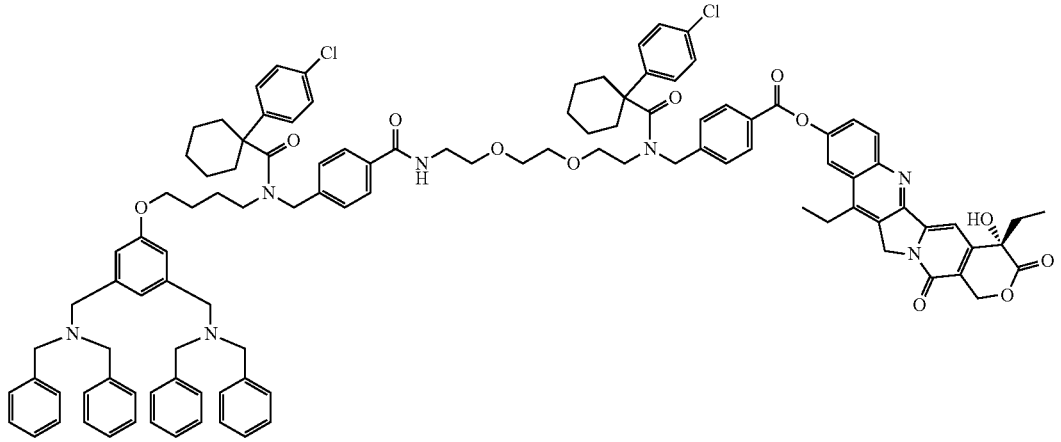 | 48 |
| 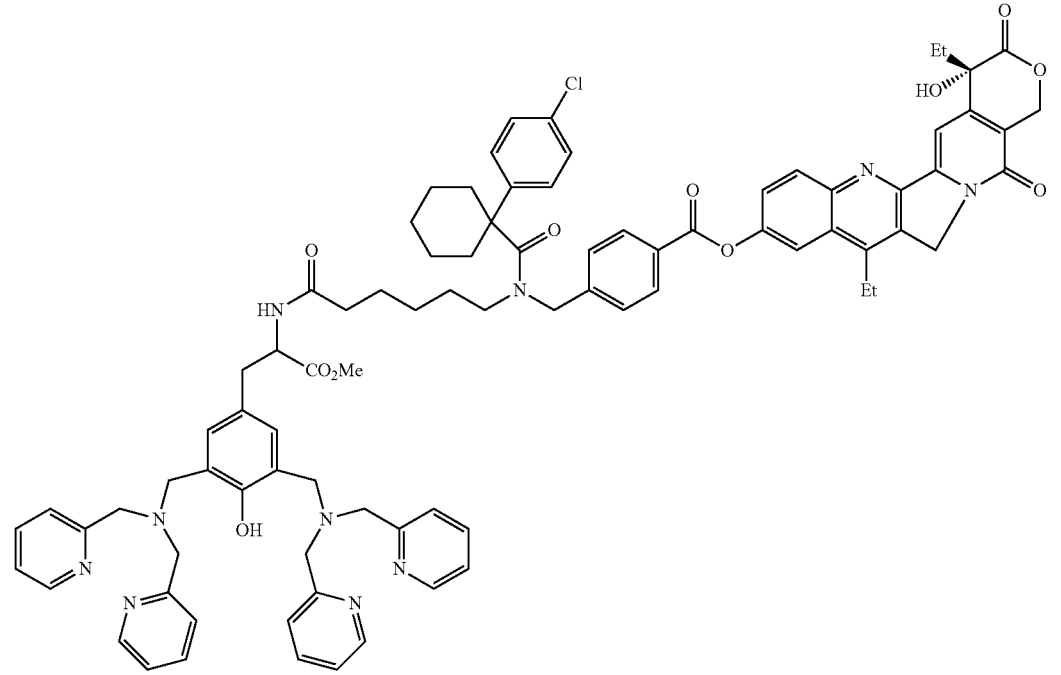 [SMILES: CCc1c2c(nc3ccc(OC(=O)c4ccc(CN(CCCCCC(=O)NC(Cc5cc(CN(Cc6ccccn6)Cc6ccccn6)c(O)c(CN(Cc6ccccn6)Cc6ccccn6)c5)C(=O)OC)C(=O)C5(c6ccc(Cl)cc6)CCCCC5)cc4)cc13)-c1cc3c(c(=O)n1C2)COC(=O)[C@]3(O)CC] | 49 |
| 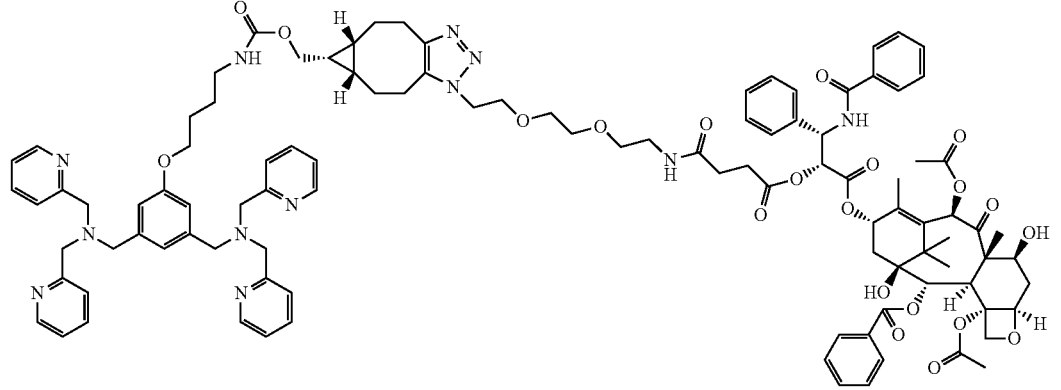 [SMILES: CC(=O)O[C@H]1C(=O)[C@@]2(C)[C@H]([C@H](OC(=O)c3ccccc3)[C@]3(O)C[C@H](OC(=O)[C@H](OC(=O)CCC(=O)NCCOCCOCCn4nnc5c4CC[C@H]4[C@@H](CC5)[C@H]4COC(=O)NCCCCOc4cc(CN(Cc5ccccn5)Cc5ccccn5)cc(CN(Cc5ccccn5)Cc5ccccn5)c4)[C@@H](NC(=O)c4ccccc4)c4ccccc4)C(C)=C1C3(C)C)[C@]1(OC(C)=O)CO[C@@H]1C[C@@H]2O] | 50 |

-continued

| Compound structures | Compound numbers |
|---|---|
| 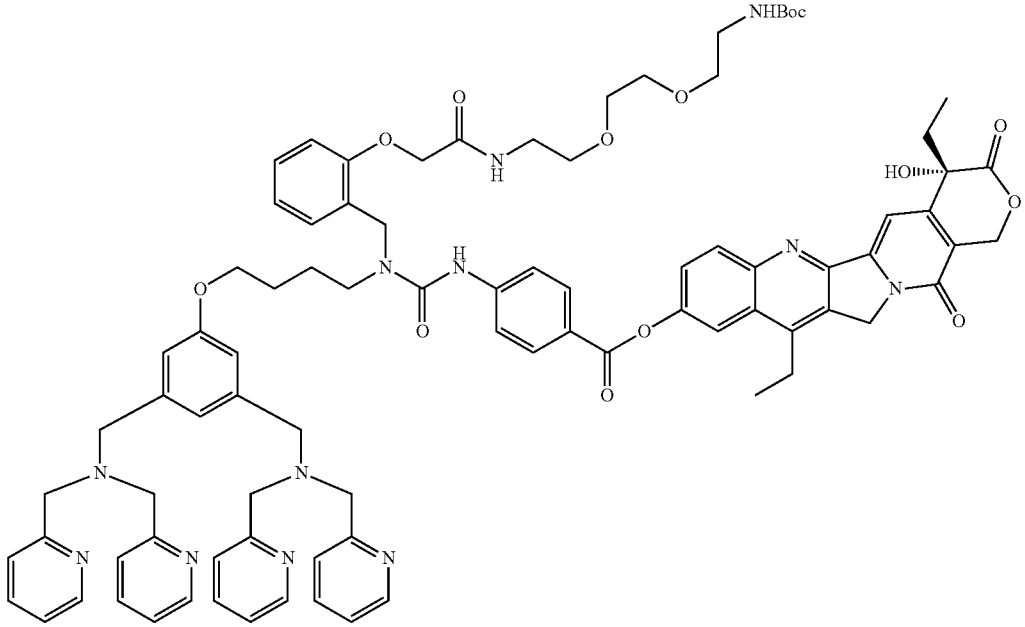 [SMILES: CCc1c2c(nc3ccc(OC(=O)c4ccc(NC(=O)N(CCCCOc5cc(CN(Cc6ccccn6)Cc6ccccn6)cc(CN(Cc6ccccn6)Cc6ccccn6)c5)Cc5ccccc5OCC(=O)NCCOCCOCCNC(=O)OC(C)(C)C)cc4)cc13)-c1cc3c(c(=O)n1C2)COC(=O)[C@]3(O)CC] | 51 |

The compounds of this invention can be prepared by synthetic methods well known in the art. See R. Larock, Comprehensive Organic Transformations ($2^{nd}$ Ed., VCH Publishers 1999); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis ($2^{nd}$ ed., John Wiley and Sons 2009) and subsequent editions thereof.

The syntheses of Compounds 1-51 and their analytical data are shown below.

Synthesis of Dipicolylamine Intermediate (DPA, Structure Shown Below)

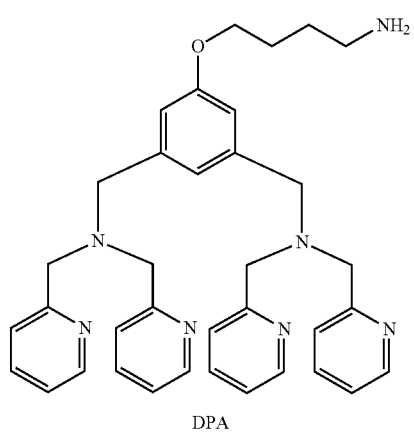 [SMILES: NCCCCOc1cc(CN(Cc2ccccn2)Cc2ccccn2)cc(CN(Cc2ccccn2)Cc2ccccn2)c1]

DPA

A dipicolylamine intermediate DPA was prepared according to the following steps:

Step 1

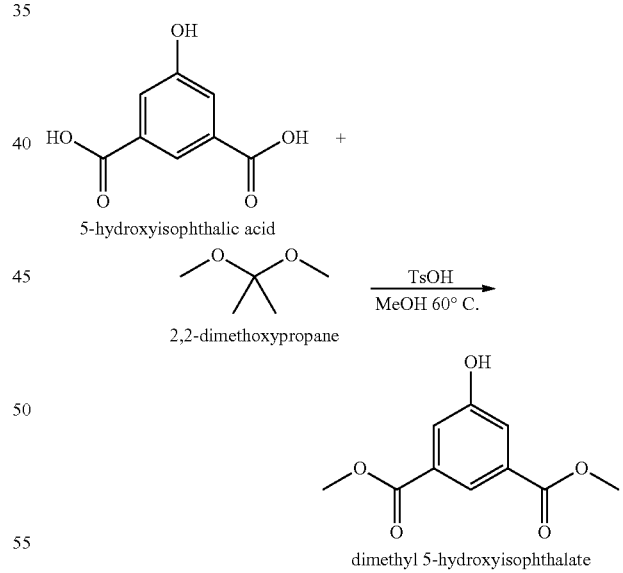

To a stirred solution of 5-hydroxyisophthalic acid (25 g, 137 mmol, 1 eq.) in 200 mL of methanol at room temperature, 2,2-dimethoxypropane (1.2 eq.) and p-toluenesulfonic acid (TsOH, 0.2 eq.) were added. After stirring at 60° C., methanol was removed by evaporation. The resultant crude mixture was partitioned in ethyl acetate (EtOAc)/water. The organic layer was dried with magnesium sulfate ($MgSO_4$) and concentrated to give a crude product, which was purified by silica-column chromatography to yield 2,2-dimethoxypropane (23 g, 79%).

$^{1}$H NMR (300 MHz, CDCl$_3$) δ 3.96 (s, 6H), 7.77 (s, 2H), 8.26 (s, 1H).

Step 2

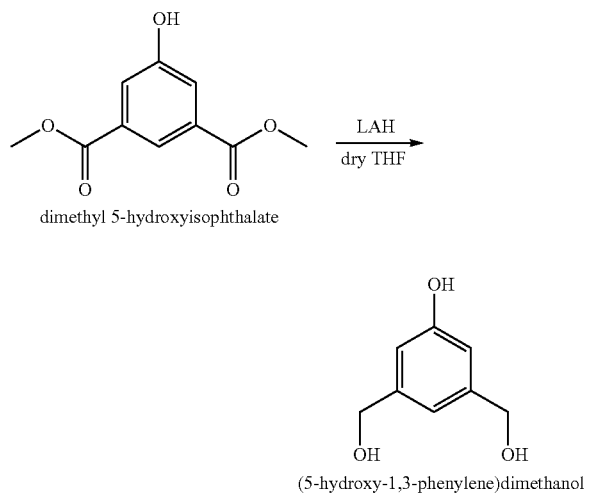

To a solution of dimethyl 5-hydroxyisophthalate (28 g, 133 mmol, 1 eq.) in 1400 mL of dry tetrahydrofuran (THF) at ice-bath temperature, lithium aluminum hydride (LiAlH$_4$ or LAH, 4 eq.) was slowly added with stirring. The resultant mixture was allowed warm to 40° C., stirred at this temperature for 16 hours, and then was added an ammonium chloride (NH$_4$Cl) aqueous solution to quench the reaction. After stirring for 1.5 hours, the mixture was filtered with celite, washed with THF. Organic volatiles were evaporated and the residue was partitioned between water and EtOAc. The aqueous phase was extracted with EtOAc three times. The combined EtOAc layers were dried over MgSO$_4$ to give product (5-hydroxy-1,3-phenylene)dimethanol (17 g, 82%).

$^{1}$H NMR (400 MHz, CDCl$_3$) δ 4.57 (s, 6H), 6.71 (s, 2H), 6.80 (s, 1H).

Step 3

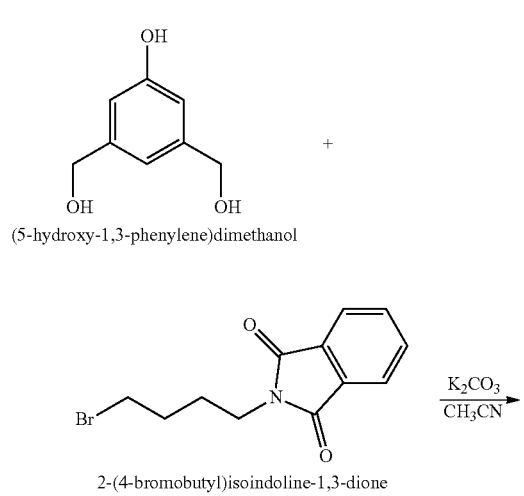

-continued

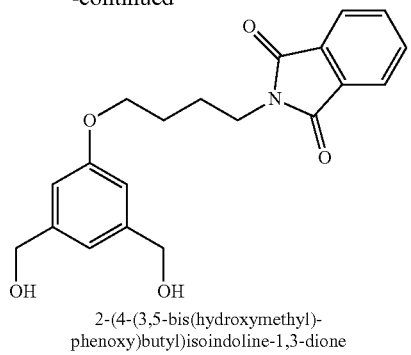
2-(4-(3,5-bis(hydroxymethyl)-phenoxy)butyl)isoindoline-1,3-dione

To a stirred solution of (5-hydroxy-1,3-phenylene)dimethanol (7.27 g, 47 mmol, 1 eq.) in 200 mL of acetonitrile at room temperature, 2-(4-bromobutyl)isoindoline-1,3-dione (1.2 eq.) and potassium carbonate (K$_2$CO$_3$, 2 eq.) were slowly added. The resultant mixture was then heated at reflux for 8 hours, after which the volatiles were removed, and the residue was partitioned between EtOAc and water. The EtOAc layer was washed with brine and dried over MgSO$_4$. Evaporation of EtOAc gave 2-(4-(3,5-bis(hydroxymethyl)phenoxy)butyl) isoindoline-1,3-dione (13 g, 78% yield).

$^{1}$H NMR (400 MHz, CDCl$_3$) δ 1.67-1.65 (m, 2H), 1.86-1.81 (m, 2H), 3.75 (t, J=5.6 Hz, 2H), 4.00 (t, J=6.0 Hz, 2H), 4.63 (s, 2H), 4.64 (s, 2H), 6.81 (s, 2H), 6.91 (s, 1H), 7.71-7.69 (m, 2H), 7.84-7.82 (m, 2H).

Step 4

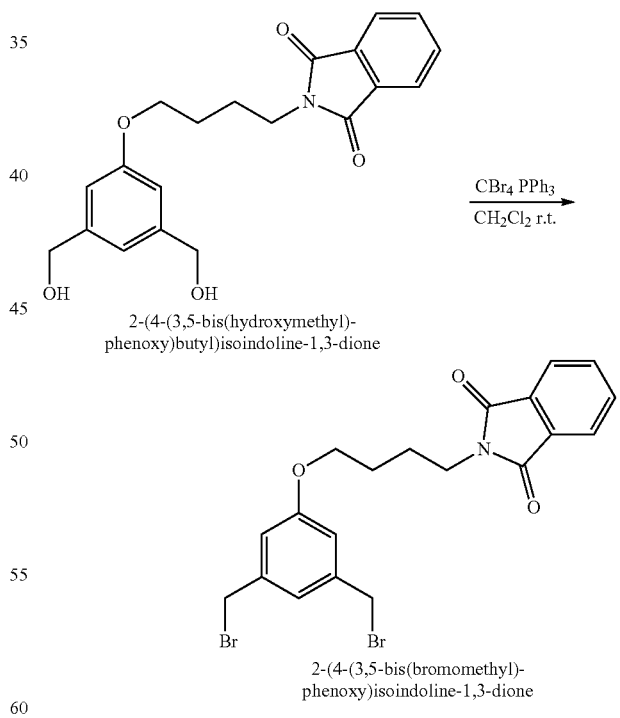

To a stirred solution of 2-(4-(3,5-bis(hydroxymethyl)phenoxy)butyl)isoindoline-1,3-dione (7.44 g, 21 mmol, 1 eq.) in 420 mL of anhydrous dichloromethane (CH$_2$Cl$_2$) in an ice bath, triphenylphosphine (PPh$_3$, 2.3 eq.) and carbon tetrabromide (CBr$_4$, 4.5 eq.) were slowly added. The resultant reaction mixture was allowed to warm to room temperature, stirred for 16, and added methanol (MeOH) to quench the reaction. After CH$_2$Cl$_2$ and MeOH were evaporated, the residue was partitioned in CH$_2$Cl$_2$/water. The CH$_2$Cl$_2$ layer was dried over MgSO$_4$ and concentrated by evaporation to give a crude product, which was purified by silica-column chromatography to yield product (5.2 g, 51%).

$^1$H NMR (300 MHz, CDCl$_3$) δ 1.90-1.81 (m, 4H), 3.77 (t, J=6.6 Hz, 2H), 4.00 (t, J=5.7 Hz, 2H), 4.41 (s, 4H), 6.82 (s, 2H), 6.98 (s, 1H), 7.74-7.70 (m, 2H), 7.86-7.84 (m, 2H).

Step 5

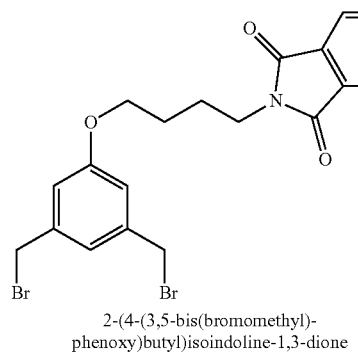

2-(4-(3,5-bis(bromomethyl)-phenoxy)butyl)isoindoline-1,3-dione

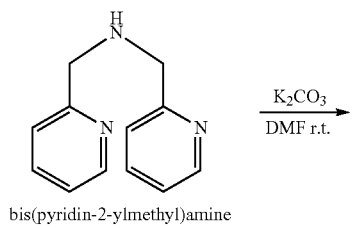

bis(pyridin-2-ylmethyl)amine

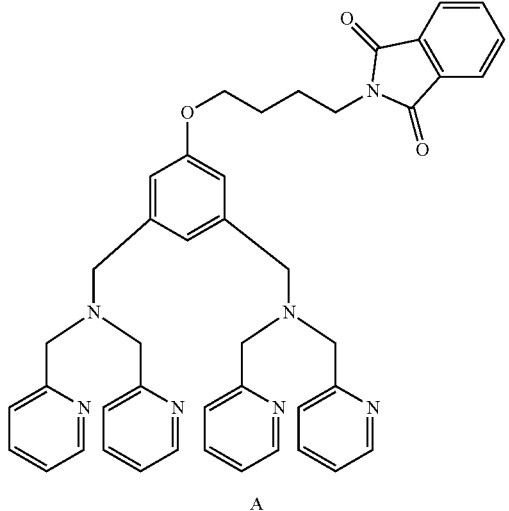

A

To a stirred solution of 2-(4-(3,5-bis(bromomethyl)phenoxy)butyl)isoindoline-1,3-dione (3.86 g, 8.06 mmol, 1 eq.) in 25 mL of dry dimethylformamide (DMF) at room temperature, bis(pyridin-2-ylmethyl)amine (2 eq.) and K$_2$CO$_3$ (5 eq.) were slowly added. After stirring for 16 hours, DMF was evaporated. The resultant crude mixture was partitioned in CH$_2$Cl$_2$/water. The CH$_2$Cl$_2$ layer was dried over MgSO$_4$, and concentrated to give a crude product, which was purified by silica-column chromatography to yield product A (4.8 g, 83%).

$^1$H NMR (400 MHz, CDCl$_3$) δ 1.89-1.82 (m, 4H), 3.61 (s, 4H), 3.78-3.74 (m, 10H), 3.96 (t, J=6.0 Hz, 2H), 6.82 (s, 2H), 7.03 (s, 1H), 7.12-7.08 (m, 4H), 7.63-7.53 (m, 8H), 7.69-7.67 (m, 2H), 7.82-7.80 (m, 2H), 8.48 (d, J=4.8 Hz, 4H).

Step 6

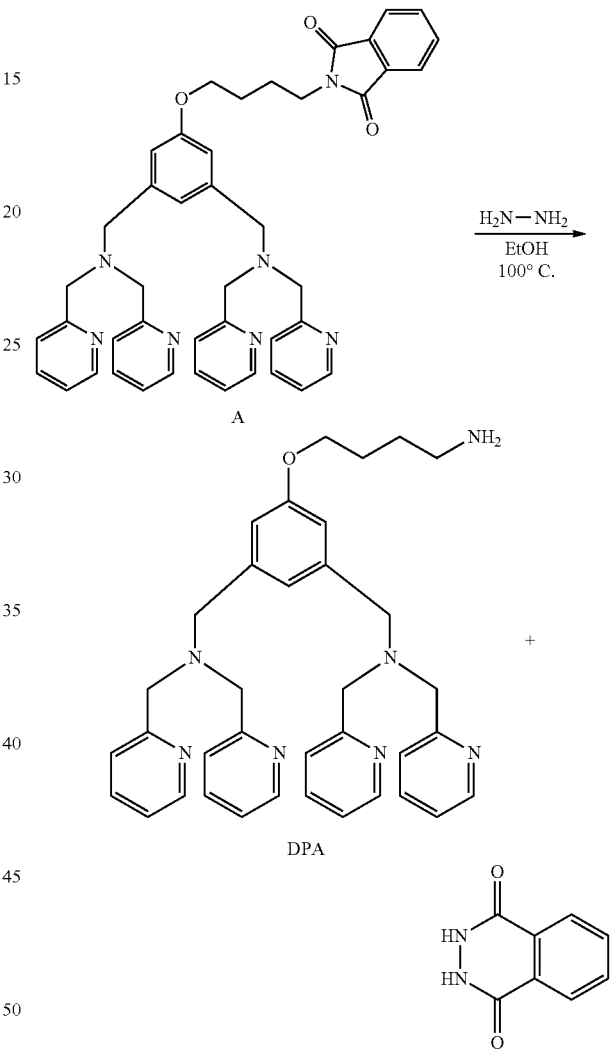

To a stirred solution of compound A (5.9 g, 8.23 mmol, 1 eq.) in 200 mL of ethanol (EtOH) at room temperature, hydrazine (H$_2$N—NH$_2$, 10 eq.) was slowly added. The resultant reaction mixture was stirred for 16 hours, heated at reflux for 2 hours, and then cooled to room temperature. Removal of EtOH gave a crude mixture, which was extracted by CH$_2$Cl$_2$ twice. The CH$_2$Cl$_2$ solutions were combined, dried over MgSO$_4$, and concentrated to afford DPA (4.1 g, 85%).

$^1$H NMR (300 MHz, CDCl$_3$) δ 1.65-1.55 (m, 2H), 1.84-1.75 (m, 2H), 2.75 (t, J=6.9 Hz, 2H), 3.56 (s, 4H), 3.78 (s, 8H), 3.94 (t, J=6.6 Hz, 2H), 6.84 (s, 2H), 7.04 (s, 1H), 7.13-7.08 (m, 4H), 7.63-7.55 (m, 8H), 8.48 (d, J=4.5 Hz, 4H).

Synthesis of Nine DPA Linkers, DL-1 to DL-9

DL-1

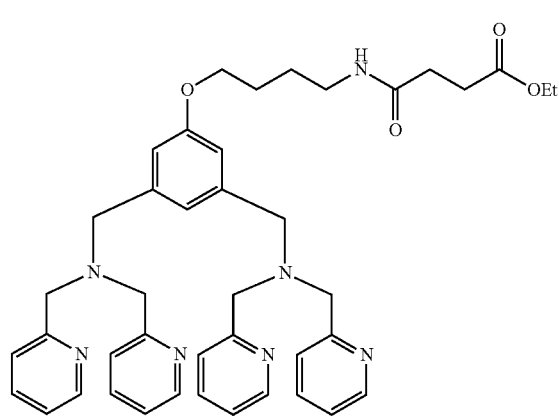 [SMILES: CCOC(=O)CCC(=O)NCCCCOc1cc(CN(Cc2ccccn2)Cc2ccccn2)cc(CN(Cc2ccccn2)Cc2ccccn2)c1]

DPA (400 mg, 0.681 mmol, 1 eq.) and triethylamine (1 mL) were dissolved in CH$_2$Cl$_2$ (40 mL), followed by addition of ethyl 4-chloro-4-oxobutanoate at 0° C. The resultant solution, after stirring at 0° C. for 2 hours, was washed with a saturated ammonium chloride aqueous solution three times (3×40 ml). The CH$_2$Cl$_2$ layers were dried over MgSO$_4$ and concentrated under reduced pressure to yield DL-1.

$^1$H NMR (400 MHz, CDCl$_3$) δ 1.27-1.19 (m, 3H), 1.70-1.67 (m, 2H), 1.84-1.78 (m, 2H), 2.44 (t, J=6.4 Hz, 2H), 2.77 (t, J=6.4 Hz, 2H), 3.43-3.29 (m, 2H), 3.64 (s, 4H), 3.79 (s, 8H), 3.96 (t, J=6 Hz, 2H), 4.16-4.09 (m, 2H), 6.83 (s, 2H), 7.05 (s, 1H), 7.14-7.11 (m, 4H), 7.64-7.57 (m, 8H), 8.50 (d, J=4.4 Hz, 4H).

DL-2

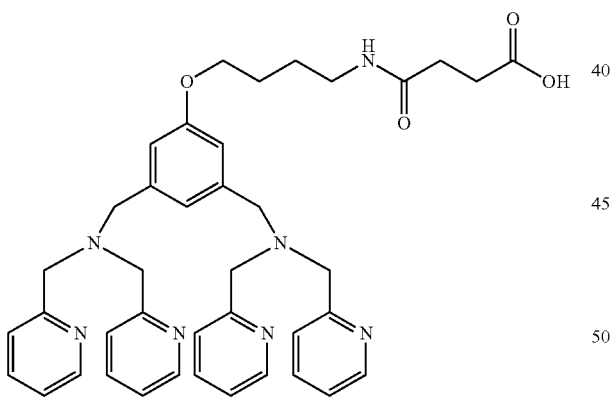

DL-1 (487 mg, 0.68 mmol, 1 eq.) was dissolved in MeOH (4 mL) and a LiOH aqueous solution (4 mL, 0.5 N), and then stirred at room temperature for 15 hours. After removal of MeOH, the resultant residue was extracted with CH$_2$Cl$_2$ (100 mL). The CH$_2$Cl$_2$ solution was then washed with a saturated ammonium chloride aqueous solution twice (2×100 mL), dried over MgSO$_4$, and concentrated under reduced pressure to yield DL-2 (380 mg).

$^1$H NMR (300 MHz, CDCl$_3$) δ 1.71-1.67 (m, 2H), 1.82-1.79 (m, 2H), 2.48 (m, 2H), 2.68 (m, 2H), 3.34 (m, 2H), 3.63 (s, 4H), 3.80 (s, 8H), 3.96 (t, J=8 Hz, 2H), 6.83 (s, 2H), 6.90 (s, 1H), 7.15-7.11 (m, 4H), 7.66-7.54 (m, 8H), 8.51 (d, J=4.8 Hz, 4H).

DL-3

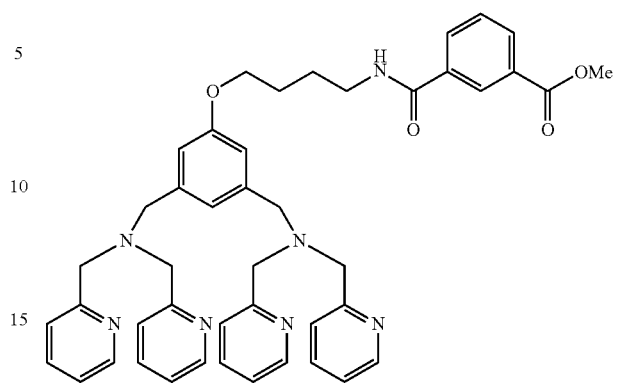

To a solution of DPA (400 mg, 0.68 mmol, 1 eq.) in CH$_2$Cl$_2$ (40 mL) were added triethylamine (2 mL) and methyl 3-(chlorocarbonyl) benzoate at 0° C. The resultant reaction mixture, after stirring at 0° C. for 2 hours, was diluted with CH$_2$Cl$_2$ (100 mL) The CH$_2$Cl$_2$ solution was washed with a saturated aqueous solution of NH$_4$Cl twice (2×100 mL), dried over MgSO$_4$, and concentrated under reduced pressure to give a crude product, which is purified by column chromatography (silica gel; MeOH:CH$_2$Cl$_2$=1:13) to yield DL-3 (280 mg, 55%).

$^1$H NMR (400 MHz, CDCl$_3$) δ 1.91-1.84 (m, 4H), 3.58-3.54 (m, 2H), 3.63 (s, 4H), 3.78 (s, 8H), 3.91 (s, 3H), 4.02 (t, J=5.2 Hz, 2H), 6.85 (s, 2H), 7.05 (s, 1H), 7.13-7.10 (m, 4H), 7.50-7.46 (m, 1H), 7.63-7.56 (m, 8H), 8.00 (d, J=7.6 Hz, 1H), 8.12 (d, J=8 Hz, 1H), 8.36 (s, 1H), 8.49 (d, J=4.4 Hz, 4H).

DL-4

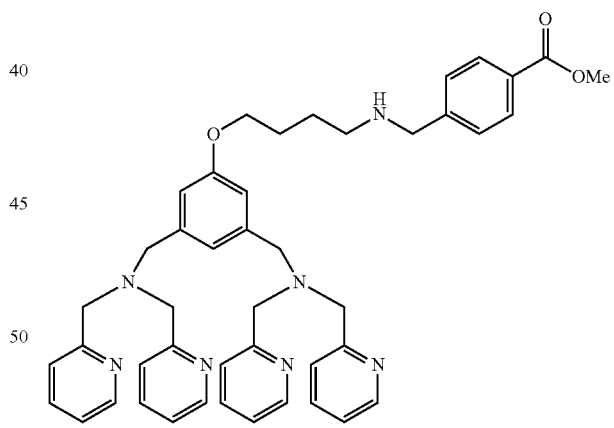

DPA (1 g, 1.7 mmol, 1 eq.) and methyl 4-formylbenzoate (840 mg, 5.12 mmol, 3 eq) were dissolved in MeOH (20 mL) and stirred at 65° C. for 15 hours. After the solution was cooled to 0° C., sodium borohydride (1 g, 26 mmol, 15 eq) was added. The mixture was stirred at 0° C. for another hour. Removal of MeOH under reduced pressure gave a residue, which was extracted with CH$_2$Cl$_2$ (100 mL) The CH$_2$Cl$_2$ solution was washed with a saturated aqueous solution of NH$_4$Cl twice (2×100 mL), dried over MgSO$_4$, and concentrated under reduced pressure. The resultant residue was purified by column chromatography (silica gel; MeOH:CH$_2$Cl$_2$=1:9) to yield DL-4 (700 mg, 56%).

¹H NMR (300 MHz, CDCl₃) δ 1.90-1.68 (m, 4H), 2.71 (t, J=7.2 Hz, 2H), 3.63 (s, 4H), 3.79 (s, 8H), 3.82 (s, 2H), 3.86 (s, 3H), 3.95 (t, J=6 Hz, 2H), 6.83 (s, 2H), 7.04 (s, 1H), 7.14-7.09 (m, 4H), 7.40 (d, J=8.1 Hz, 2H), 7.63-7.55 (m, 8H), 7.98 (d, J=8.1 Hz, 2H), 8.48 (d, J 4.2 Hz, 4H).

DL-5

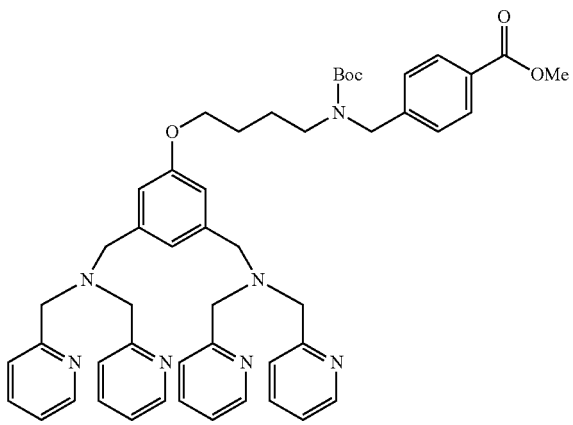 [SMILES: COC(=O)c1ccc(CN(CCCCOc2cc(CN(Cc3ccccn3)Cc3ccccn3)cc(CN(Cc3ccccn3)Cc3ccccn3)c2)C(=O)OC(C)(C)C)cc1]

DL-4 (600 mg, 0.82 mmol, 1 eq) and di-tert-butyl dicarbonate (360 mg, 1.65 mmol, 2 eq) were dissolved in CH₂Cl₂ (60 mL) and stirred at room temperature for 15 hours. After CH₂Cl₂ was removed, a residue was obtained and purified by column chromatography (silica gel; MeOH:CH₂Cl₂=1:13) to yield DL-5 (550 mg, 81%).

¹H NMR (300 MHz, CDCl₃) δ 1.45-1.40 (m, 9H), 1.72 (m, 2H), 1.89 (m, 2H), 3.31-3.21 (m, 2H), 3.64 (s, 4H), 3.79 (s, 8H), 3.89 (s, 3H), 3.92 (m, 2H), 4.47 (m, 2H), 6.82 (s, 2H), 7.07 (s, 1H), 7.14-7.09 (m, 4H), 7.27 (d, J=9 Hz, 2H), 7.63-7.56 (m, 8H), 7.98 (d, J=8.7 Hz, 2H), 8.50 (d, J=4.8 Hz, 4H).

DL-6

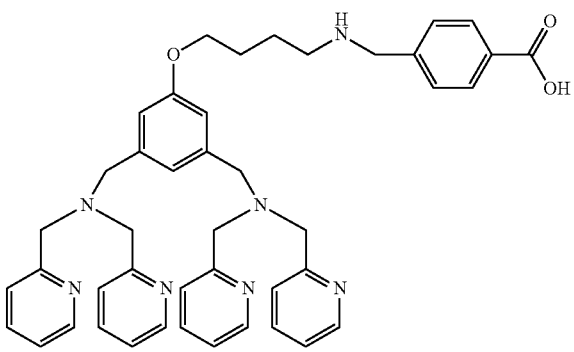 [SMILES: O=C(O)c1ccc(CNCCCCOc2cc(CN(Cc3ccccn3)Cc3ccccn3)cc(CN(Cc3ccccn3)Cc3ccccn3)c2)cc1]

DL-4 (300 mg, 0.41 mmol) was dissolved in MeOH (3 mL) and an aqueous LiOH solution (3 mL, 0.5 N). The resultant mixture was stirred at room temperature for 15 hours. Removal of MeOH gave a residue, which was extracted with CH₂Cl₂ (100 mL) The CH₂Cl₂ solution was then washed with a saturated aqueous solution of NH₄Cl twice (2×100 mL), dried over MgSO₄, and concentrated under reduced pressure to yield DL-6 (260 mg, 88%).

DL-7

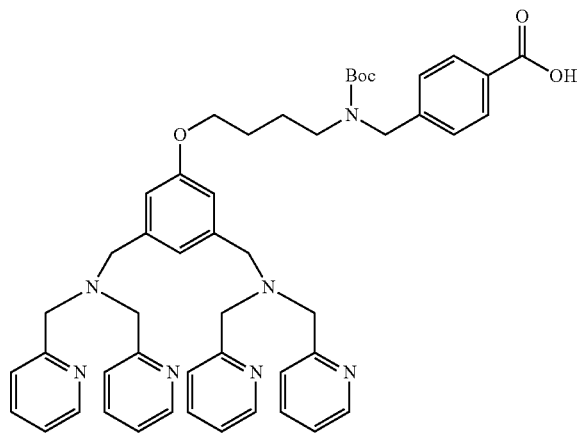 [SMILES: CC(C)(C)OC(=O)N(CCCCOc1cc(CN(Cc2ccccn2)Cc2ccccn2)cc(CN(Cc2ccccn2)Cc2ccccn2)c1)Cc1ccc(C(=O)O)cc1]

DL-5 (550 mg, 0.66 mmol) was dissolved in MeOH (6 mL) and an aqueous LiOH solution (6 mL, 0.5 N). The resultant mixture was stirred at room temperature 15 hours. MeOH was removed to give a residue, which was extracted with CH₂Cl₂ (100 mL). The CH₂Cl₂ solution was washed with a saturated aqueous solution of NH₄Cl twice (2×100 ml), dried over MgSO₄, and concentrated under reduced pressure to yield DL-7 (480 mg, 89%).

¹H NMR (300 MHz, CDCl₃) δ 1.50-1.26 (m, 13H), 3.29-3.23 (m, 2H), 3.65 (s, 4H), 3.81 (m, 10H), 4.53 (s, 2H), 6.77 (s, 2H), 6.93 (s, 1H), 7.15-7.11 (m, 4H), 7.38 (m, 2H), 7.63-7.53 (m, 8H), 8.10 (d, J=7.8 Hz, 2H), 8.54 (d, J=4.2 Hz, 2H)

DL-8

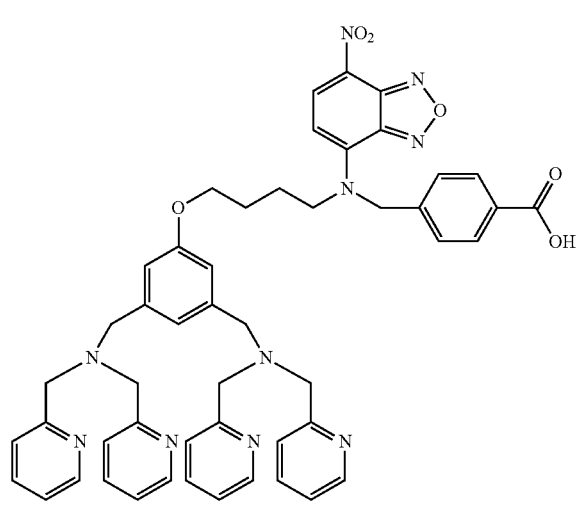 [SMILES: O=C(O)c1ccc(CN(CCCCOc2cc(CN(Cc3ccccn3)Cc3ccccn3)cc(CN(Cc3ccccn3)Cc3ccccn3)c2)c2ccc([N+](=O)[O-])c3nonc23)cc1]

DL-6 (260 mg, 0.36 mmol, 1 eq), K₂CO₃ (745 mg, 5.40 mmol, 15 eq), 4-chloro-7-nitrobenzo[c][1,2,5]oxadiazole (100 mg, 0.50 mmol), and CH₂Cl₂ (30 mL) were mixed and stirred at 40° C. for 15 hours. The resultant reaction mixture was then extracted with CH₂Cl₂ (100 mL) Subsequently, the CH₂Cl₂ solution was washed with water twice (2×100 mL), dried over MgSO₄, and concentrated under reduced pressure. The resultant residue was purified by column chromatography (silica gel; MeOH:CH₂Cl₂=1:1) to yield DL-8 (200 mg, 63%)

¹H NMR (400 MHz, DMSO) δ 1.36 (m, 1H), 1.69-1.51 (m, 3H), 3.13 (m, 2H), 3.54 (s, 4H), 3.66 (m, 10H), 3.98 (m, 2H), 6.68 (m, 1H), 6.79 (d, J=4.4 Hz, 2H), 7.04 (d, J=5.6 Hz, 1H), 7.21-7.17 (m, 4H), 7.35-7.25 (m, 2H), 7.54-7.51 (m, 4H), 7.71-7.63 (m, 4H), 7.86 (d, J=8.4 Hz, 2H), 8.38 (m, 1H), 8.44 (d, J=5.2 Hz, 4H).
DL-9

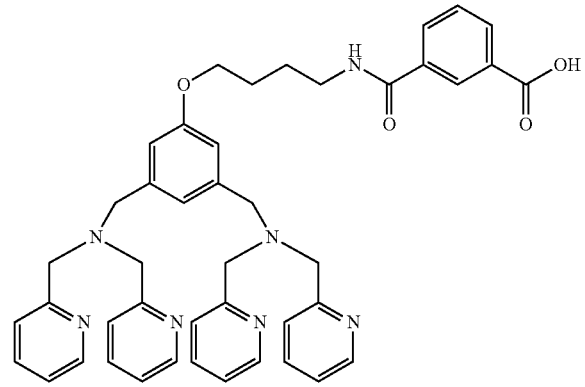 [SMILES: O=C(O)c1cccc(C(=O)NCCCCOc2cc(CN(Cc3ccccn3)Cc3ccccn3)cc(CN(Cc3ccccn3)Cc3ccccn3)c2)c1]

A solution of DL-3 (0.37 mmol) in MeOH (3 mL) and an aqueous LiOH solution (3 mL, 0.5 N) was stirred at room temperature for 15 hours. MeOH was removed under reduced pressure to give a residue, which was extracted with $CH_2Cl_2$ (100 mL). The $CH_2Cl_2$ solution was then washed with a saturated aqueous solution of $NH_4Cl$ twice (2×100 mL), dried over $MgSO_4$, and concentrated under reduced pressure to yield DL-9 (240 mg, 88%).

$^1H$ NMR (300 MHz, $CDCl_3$) δ 1.97-1.86 (m, 4H), 3.64 (m, 6H), 3.80 (s, 8H), 4.14 (m, 2H), 7.08 (s, 2H), 7.20-7.12 (m, 5H), 7.62-7.51 (m, 8H), 8.21 (d, J=7.2 Hz, 2H), 8.47 (s, 1H), 8.56 (d, J=4.8 Hz, 4H).

EXAMPLE 1

Preparation of Compound 1

Compound 1 of this invention was prepared following the procedure described below.

To a solution of DL-2 (200 mg, 0.29 mmol, 1 eq) in DMF (20 mL) were added 4,11-diethyl-4,9-dihydroxy-1H-pyrano[3',4':6,7]indolizino[1,2-b]quinoline-3,14 (4H,12H)-dione (170 mg, 0.44 mmol, 1.5 eq), hydroxybenzotriazole (117 mg, 0.87 mmol, 3 eq), N-(3-dimethylaminopropyl)-N'-ethylcarbodiimide hydrochloride (170 mg, 0.87 mmol, 3 eq), and N-methylmorpholine (175 mg, 1.74 mmol, 6 eq). After stirring at room temperature for 15 hours, the resultant reaction mixture was extracted with $CH_2Cl_2$ (300 mL) Subsequently, the $CH_2Cl_2$ solution was washed with a saturated aqueous solution of $NaHCO_3$ (300 mL) and water (5×300 mL), dried over $MgSO_4$, and then concentrated under reduced pressure to give a residue. Compound 1 (130 mg, 42%) was obtained by purifying the residue with column chromatography (silica gel; $MeOH:CH_2Cl_2$=1:13).

$^1H$ NMR (400 MHz, $CDCl_3$) δ 1.01 (t, J=7.2 Hz, 3H), 1.34 (t, J=7.6 Hz, 3H), 1.74-1.67 (m, 2H), 1.94-1.77 (m, 4H), 2.62 (t, J=6.4 Hz, 2H), 3.00 (t, J=6.4 Hz, 2H), 3.11-3.06 (m, 2H), 3.39-3.34 (m, 2H), 3.61 (s, 4H), 3.76 (s, 8H), 3.92 (t, J=j=6.0 Hz, 2H), 5.20 (s, 2H), 5.28 (d, J=16.4 Hz, 1H), 5.71 (d, J=16.4 Hz, 1H), 6.77 (s, 2H), 7.04 (s, 1H), 7.12-7.09 (m, 4H), 7.63-7.50 (m, 10H), 7.77 (d, J=2.4 Hz, 1H), 8.14 (d, J=9.2 Hz, 1H), 8.47 (d, J=4.8 Hz, 4H). Mass: $(EM+2H^+)/2$. found 532.27.

EXAMPLES 2-51

Preparation of Compounds 2-51

The synthesis of Compound 42 is described immediately below. As for compounds 2-41 and 43-51, they were obtained following a similar procedure or a procedure similar to that described in Example 1 above.

Scheme 1 below depicts a synthetic sequence of preparing a linker, i.e., 42-Linker, from commercially available B via intermediates C and D.

Synthesis of 42-Linker, a Linker for Use in Preparing Compound 42:

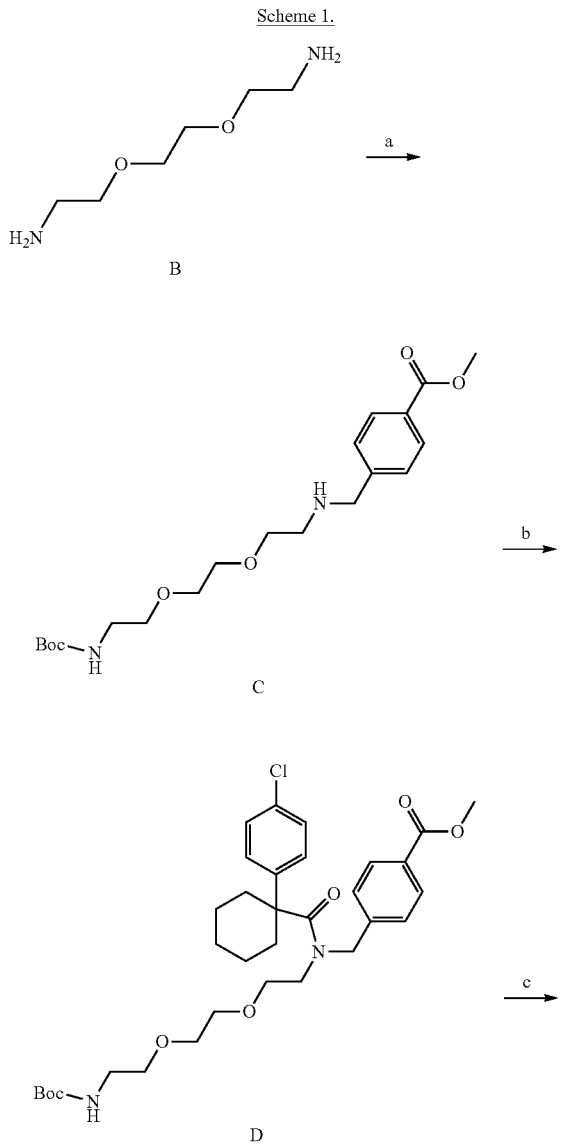

Scheme 1.

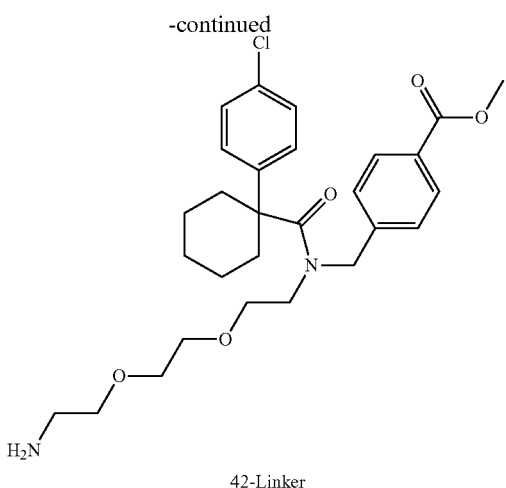

42-Linker

Synthesis of a linker:
a I. Boc₂O, DCM, 3 hours; and II. Methyl 4-formylbenzoate, NaBH₄, MeOH, room temperature, 1 hour;
b 1-(4-Chlorophenyl)cyclo-hexanecarbonyl chloride, DCM, room temperature, 1 hour;
c 4M HCl in 1,4-dioxane, MeOH, room temperature, 12 hours.

Synthesis of Compound C:

To a solution of the commercial available B (15 g, 101.21 mmol) in CH$_2$Cl$_2$ (300 mL) was added trimethylamine (TEA, 1 eq.), followed by di-tert-butyl dicarbonate (Boc$_2$O, 0.5 eq). The reaction was stirred at room temperature for 3 hours, after which time the solvent was removed in vacuo. The crude was partitioned between H$_2$O and DCM. The layers were separated, and the organics were dried over sodium sulfate (Na$_2$SO$_4$) and concentrated to a transparent oil. To the transparent oil in 200 ml of MeOH was added methyl 4-formylbenzoate (15 g, 91.35 mmol, 0.9 eq.). The sodium borohydride (3.7 g, 97.80 mmol, 0.9 eq.) was added after stirring at room temperature for 3 hours. The MeOH was removed and the residue dissolved in 200 ml CH$_2$Cl$_2$. The protonated product was extracted from CH$_2$Cl$_2$ with 200 ml NH$_4$Cl$_{(aq)}$. The organic layers were combined, dried with Na$_2$SO$_4$, filtered and the solvent evaporated. Purification of the crude residue by flash chromatography on silica gel eluting with EtOAc/Hexane (2:1) to give 12.03 g of product C as a transparent oil (30.36 mmol, 30%).

Synthesis of Compound D:

To the compound C (12.03 g, 30.36 mmol) in 200 ml CH$_2$Cl$_2$ was added 1-(4-Chlorophenyl)cyclo-hexanecarbonyl chloride (11.57 g, 45.54 mmol, 1.5 eq.) and triethylamine (10 ml, 43.08 mmol). The reaction was stirred for 2 hours at room temperature. The protonated product was extracted from 200 ml CH$_2$Cl$_2$ with 200 ml NH$_4$Cl$_{(aq)}$. The organic layer was dried with Na$_2$SO$_4$, filtered, and the solvent evaporated. Purification of the crude residue by flash chromatography on silica gel eluting with EA/Hexane (2:1) gave 13.11 g of compound D as a transparent oil (21.25 mmol, 70%).

Synthesis of Compound 42-Linker:

To the compound D (13.11 g, 21.25 mmol) in MeOH (200 mL) was added 4 M hydrochloric acid (HCl) in dioxane (10 mL). The reaction was stirred at room temperature for 2 hours, after which time it was concentrated in vacuo. The crude was partitioned between NaH$_4$Cl$_{(aq)}$ and DCM. The layers were separated, and the organics were dried (Na$_2$SO$_4$) and concentrated to obtain compound 46-Linker as a transparent oil (7.68 g, 14.87 mmol, 70%).

Scheme 2 below depicts a synthetic sequence of preparing Compound 42 from the intermediate DPA via intermediates E, F, G, H, and I.

Synthesis of Compound 42:

Scheme 2

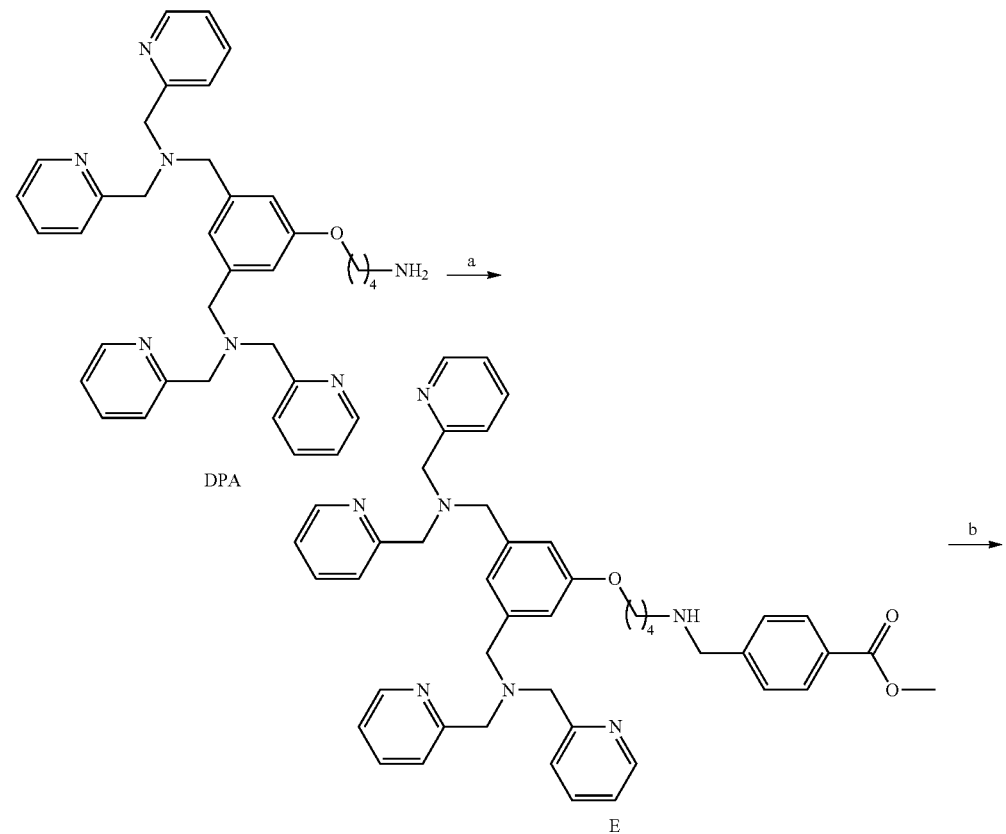

-continued
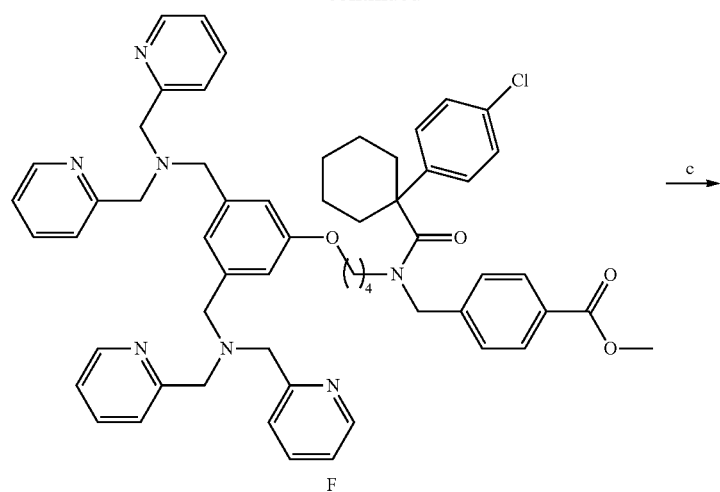
F
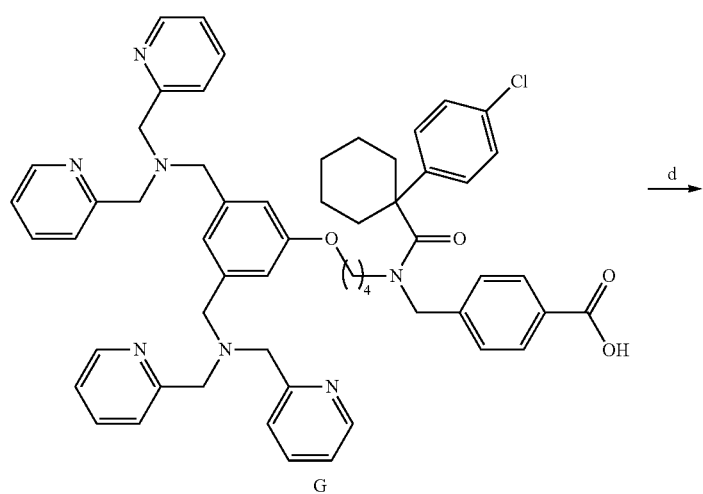
G
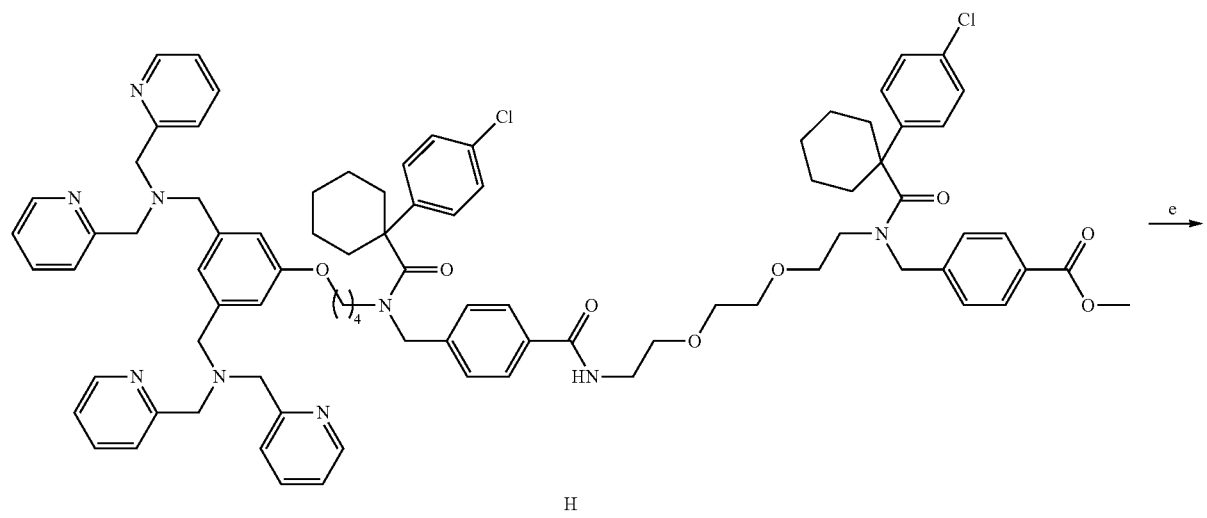
H

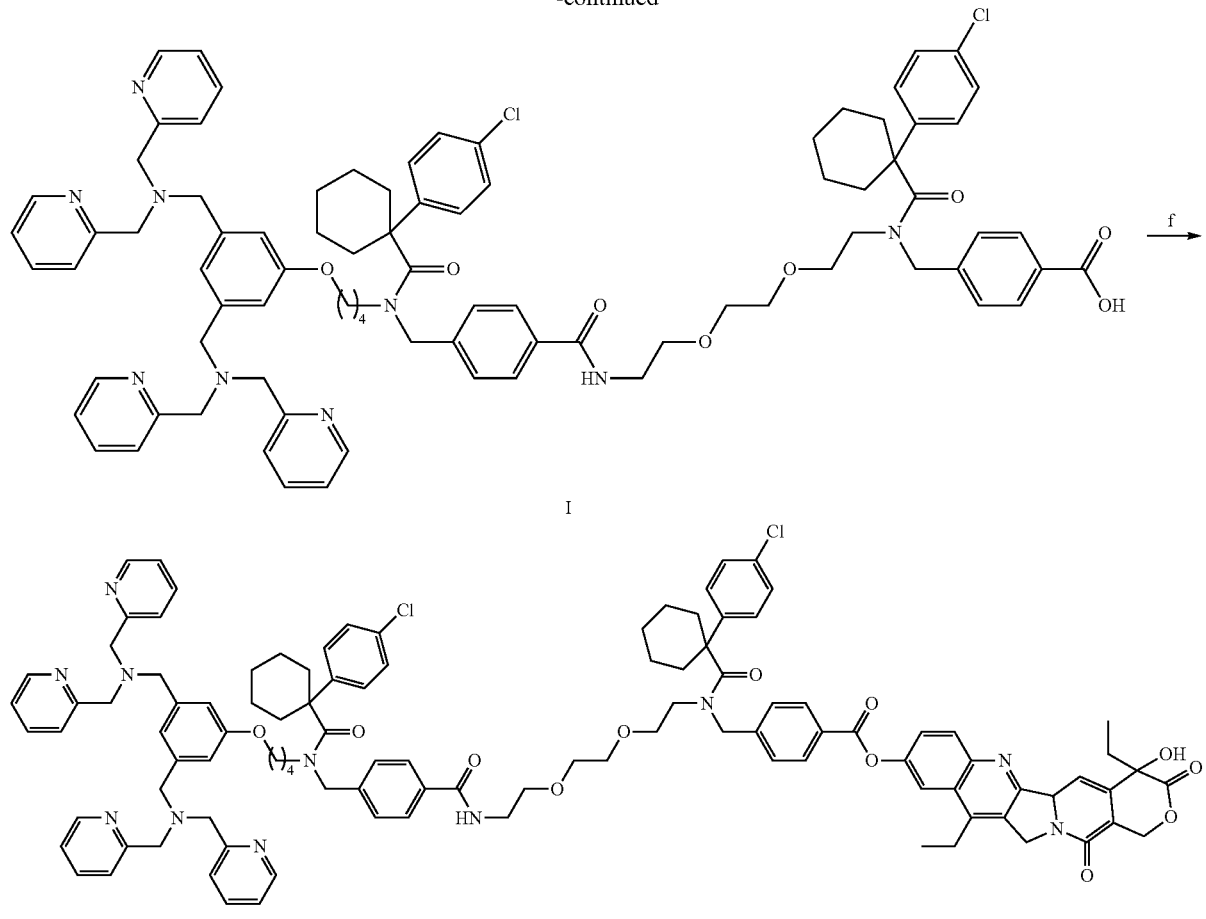

Compound 42

Synthesis of Compound 42.
a Methyl 4-formylbenzoate, NaBH$_4$, MeOH, room temperature, 1 hour (90%);
b 1-(4-Chlorophenyl)cyclo-hexanecarbonyl chloride, CH$_2$Cl$_2$, room temperature, 1 hour (90%);
c 0.5M LiOH$_{(aq)}$, MeOH, room temperature, 15 hours (90%);
d 42-Linker, HOBt, EDCI, NMM, room temperature, 15 hours (40%);
e 0.5M LiOH$_{(aq)}$, MeOH, room temperature, 15 hours (82%);
f HOBt, EDCI, NMM, 4,11-diethyl-4,9-dihydroxy-1H-pyrano[3′,4′:6,7]indolizino[1,2-b]quinoline-3,14-(4H,12H)-dione, room temperature, 15 hours (30%).

Synthesis of Compound E:

To the above-mentioned DPA (10 g, 17.01 mmol) in 200 ml of MeOH was added methyl 4-formylbenzoate (5 g, 30.45 mmol, 1.8 eq.). Sodium borohydride (3.7 g, 97.80 mmol, 5.7 eq.) was added after stirring at room temperature for 3 hours. MeOH was removed and the residue was dissolved in 200 ml of CH$_2$Cl$_2$. The protonated product was extracted from CH$_2$Cl$_2$ with 200 ml of 1M HCl$_{(aq)}$. The aqueous layer was neutralized and the product was extracted into 200 ml of CH$_2$Cl$_2$. The organic layers were combined, dried with Na$_2$SO$_4$, and filtered, and the solvent was evaporated to give 11.26 g of product E as a yellow oil (15.30 mmol, 90%). $^1$H NMR (300 MHz, CDCl$_3$): δ 1.70-1.78 (m, 2H), 1.80-1.86 (m, 2H), 2.71 (t, J=6.8 Hz, 2H), 3.62 (s, 4H), 3.78 (s, 8H), 3.87 (s, 2H), 3.89 (s, 3H), 3.95 (t, J=6.4 Hz, 2H), 6.82 (s, 2H), 7.03 (s, 1H), 7.03-7.13 (m, 4H), 7.40 (d, J=8.0 Hz, 2H), 7.55-7.62 (m, 8H), 7.98 (d, J=8.0 Hz, 2H), 8.48 (d, J=8.0 Hz, 2H).

Synthesis of Compound F:

To the compound E (11.26 g, 15.30 mmol) in 200 ml of CH$_2$Cl$_2$ was added 1-(4-Chlorophenyl)cyclo-hexanecarbonyl chloride (7.71 g, 30.00 mmol, 2 eq.) and trimethylamine (5 ml, 21.54 mmol). The reaction was stirred for 2 hours at room temperature. The protonated product was extracted from 200 ml of CH$_2$Cl$_2$ with 200 ml of 1M HCl$_{(aq)}$. The aqueous layer was neutralized and the product was extracted into 200 ml of CH$_2$Cl$_2$. The organic layer was dried with Na$_2$SO$_4$, filtered, and the solvent was evaporated to give 13.17 g of product F as a yellow oil (13.77 mmol, 90%). $^1$H NMR (300 MHz, CDCl$_3$): δ 1.62 (brs, 12H), 2.24 (brs, 2H), 2.90 (brs, 1H), 3.23 (brs, 1H), 3.63 (s, 4H), 3.78 (s, 8H), 3.88 (s, 3H), 0.3.92 (m, 2H), 4.02-4.14 (m, 2H), 6.78 (s, 2H), 6.95-7.39 (m, 11H), 7.55-7.63 (m, 8H), 7.93 (d, J=7.2 Hz, 2H), 8.48 (d, J=6.4 Hz, 4H).

Synthesis of Compound G:

To the compound F (13.17 g, 13.77 mmol) in 300 ml of MeOH was added 50 ml of 0.5M LiOH$_{(aq)}$. The reaction mixture was stirred at room temperature for 15 hours. The solvent was removed and the residue was redissolved in CH$_2$Cl$_2$. The insoluble residue was filtered off. The filtrate was washed with water, dried over MgSO$_{4(s)}$ and the solvent was removed under vacuum. The product G was obtained as yellowish powder (11.68 g, 12.39 mmol, 90%), which was directly used for the next step.

Synthesis of Compound H:

A solution containing G (11.68 g, 12.39 mmol) in 40 ml of DMF was heated to 40° C. EDCI (2 g, 12.8 mmol) and HOBt (2 g, 14.8 mmol) were added and the resulting reaction was allowed to stir at room temperature for 30 minutes, compound 42-Linker, 4-({{2-[2-(2-Amino-ethoxy)-ethoxy]-ethyl}-[1-(4-chloro-phenyl)-cyclohexanecarbonyl]-amino}-methyl)-benzoic acid methyl ester (9.6 g, 18.58 mmol) was added followed by addition of N-methylmorpholine (NMM, 5 ml, 45.5 mmol). The reaction was stirred at room temperature for 15 hours, after which time it was diluted with $H_2O$. The aqueous solution was separated and extracted with 200 ml of $CH_2Cl_2$. The combined extracts were washed with brine (4×100 mL), dried over $Na_2SO_{4(s)}$, filtered, and evaporated. Purification of the crude residue by flash chromatography on pH=7 silica gel eluting with $MeOH/CH_2Cl_2$(1:9) gave rise to ester compound H (7.14 g, 4.95 mmol, 40%).

Synthesis of Compound I:

To the compound H (7.14 g, 4.95 mmol) in 200 ml of MeOH was added 30 ml 0.5M $LiOH_{(aq)}$. The reaction mixture was stirred at room temperature for 15 hours. The solvent removed and the residue was redissolved in 100 ml $CH_2Cl_2$. The insoluble residue filtered off. The filtrate was washed with water, dried over $MgSO_{4(s)}$) and the solvent removed under vacuum. The product compound I was obtained as white powder (5.83 g, 4.08 mmol, 82%), which was directly used for the next step.

Synthesis of Compound 42:

A solution of I (5.83 g, 4.08 mmol) in 20 ml of DMF was heated to 40° C. 1-Ethyl-3-(3-dimethylaminopropyl)carbodi-imide (EDCI, 1 g, 6.4 mmol, 1.5 eq.) and hydroxybenzotria-zole (HOBt, 1 g, 7.2 mmol, 1.7 eq.) were added and the reaction allowed to stir. After stirring at room temperature for 30 min, 4,11-diethyl-4,9-dihydroxy-1H-pyrano[3',4':6,7]in-dolizino[1,2-b]quinoline-3,14-(4H,12H)-dione (3 g, 7.64 mmol, 1.87 eq.) was added followed by N-methylmorpholine (NMM, 5 ml, 45.5 mmol). The reaction was stirred at room temperature for 15 hours, after which time it was diluted with $H_2O$. The aqueous solution was separated and extracted with 100 ml of $CH_2Cl_2$. The combined extracts were washed with brine (4×100 mL), dried over $Na_2SO_{4(s)}$, filtered, and evaporated. Purification of the crude residue by flash chromatography on pH=7 silica gel eluting with $MeOH/CH_2Cl_2$ (0.5:9.5) gave rise to white power ester Compound 42 (2.21 g, 1.22 mmol, 30%).

Compound 2 was prepared from DL-9 at a yield of 40%. $^1$H NMR (400 MHz, $CD_3OD$) δ 1.02 (t, J=7.6 Hz, 3H), 1.39 (t, J=7.6 Hz, 3H), 1.93-1.98 (m, 6H), 3.21-3.23 (m, 2H), 3.57 (m, 2H), 3.78 (s, 4H), 3.96 (d, J=16 Hz, 4H), 4.11 (m, 2H), 4.34 (d, J=16 Hz, 4H), 5.32 (s, 2H), 5.38 (d, J=16.4 Hz, 1H), 5.58 (d, J=16.4 Hz, 1H), 6.72 (s, 1H), 6.81 (s, 2H), 7.60 (d, J=7.6 Hz, 4H), 7.65 (s, 1H), 7.67-7.76 (m, 4H), 8.11-8.22 (m, 6H), 8.39 (d, J=7.2 Hz, 1H), 8.69 (d, J=4 Hz, 4H). Mass: $(EM+2H^+)/2$. found 555.27.

Compound 3:

$^1$H NMR (400 MHz, DMSO) δ 0.86 (t, J=6.8 Hz, 3H), 1.24 (t, J=7.6 Hz, 3H), 1.45 (m, 4H), 1.71 (m, 4H), 1.85 (m, 2H), 2.67 (m, 2H), 3.14-3.16 (m, 2H), 3.55 (s, 4H), 3.67 (s, 8H), 3.94 (m, 2H), 5.30 (s, 2H), 5.42 (s, 2H), 6.80 (s, 2H), 7.04 (s, 1H), 7.20-7.23 (m, 4H), 7.31 (s, 1H), 7.54 (d, J=7.6 Hz, 4H), 7.61 (d, J=9.2 Hz, 1H), 7.68-7.72 (m, 4H), 7.95 (s, 1H), 8.16 (d, J=8.8 Hz, 1H), 8.45 (d, J=5.6 Hz, 4H). Mass: $(EM+2H^+/2$. found 510.

Compound 4:

$^1$H NMR (300 MHz, $CDCl_3$) δ 1.05 (t, J=7.2 Hz, 3H), 1.39 (t, J=7.5 Hz, 3H), 1.97-1.83 (m, 6H), 3.13 (q, J=7.5 Hz, 2H), 3.50 (s, 4H), 3.54 (s, 8H), 3.60-3.64 (m, 2H), 4.04 (m, 2H), 5.28 (d, J=11.7 Hz, 2H), 5.30 (d, J=16.8 Hz, 1H), 5.74 (d, J=16.2 Hz, 1H), 6.80 (s, 2H), 7.12 (s, 1H), 7.31-7.18 (m, 12H), 738-7.41 (m, 8H), 7.55-7.60 (m, 1H), 7.66-7.68 (m, 2H), 7.93 (d, J=2.1 Hz, 1H), 8.06 (d, J=7.8 Hz, 1H), 8.27 (d, J=9 Hz, 1H), 8.34 (d, J=7.5 Hz, 1H), 8.63 (s, 1H). Mass: $(EM+2H^+)/2$. found 553.74.

Compound 5:

$^1$H NMR (300 MHz, $CDCl_3$) δ 1.05 (t, J=7.2 Hz, 3H), 1.41 (t, J=7.8 Hz, 3H), 1.83-1.97 (m, 6H), 2.78 (t, J=7.2 Hz, 2H), 3.13-3.21 (m, 2H), 3.65 (s, 4H), 3.80 (s, 8H), 3.96-4.00 (m, 4H), 5.27 (s, 2H), 5.31 (d, J=16.2 Hz, 1H), 5.76 (d, J=16.2 Hz, 1H), 6.84 (s, 2H), 7.07 (s, 1H), 7.10-7.15 (m, 4H), 7.52-7.66 (m, 11H), 7.69 (d, J=2.1 Hz, 1H), 7.95 (d, J=1.8 Hz, 1H), 8.21 (d, J=7.8 Hz, 2H), 8.28 (d, J=9 Hz, 1H), 8.50 (d, J=4.8 Hz, 4H). Mass: $(EM+2H^+)/2$. found 549.

Compound 6:

$^1$H NMR (300 MHz, $CDCl_3$): δ=8.61 (t, J=1.5 Hz, 1H), 8.49 (dt, J=4.8, 1.2 Hz, 4H), 8.34 (dt, J=7.8, 1.5 Hz, 1H), 8.25 (d, J=9.0 Hz, 1H), 8.07 (dt, J=8.1, 1.5 Hz, 1H), 7.92 (d, J=2.1 Hz, 1H), 7.67-7.63 (m, 3H), 7.62-7.56 (m, 9H), 7.41 (d, J=7.5 Hz, 1H), 7.30-7.27 (m, 5H), 7.25-7.18 (m, 1H), 7.14-7.10 (m, 4H), 7.07 (s, 1H), 6.80 (s, 2H), 6.15-6.11 (m, 1H), 5.73 (d, J=16.5 Hz, 1H), 5.31-5.25 (m, 3H), 4.84 (dd, J=14.0, 8.0 Hz, 1H), 3.89 (t, J=5.6 Hz, 2H), 3.79 (s, 8H), 3.64 (s, 4H), 3.36-3.10 (m, 6H), 1.97-1.83 (m, 2H), 1.66-1.57 (m, 4H), 1.40 (t, J=7.6 Hz, 3H), 1.04 (t, J=7.4 Hz, 3H). Mass: $(EM+2H^+)/2$. found 629.

Compound 7:

$^1$H NMR (300 MHz, $CDCl_3$): δ=8.46 (d, J=4.5 Hz, 4H), 8.28 (d, J=8.4 Hz, 2H), 8.24 (d, J=9.3 Hz, 1H), 7.97 (d, J=8.4 Hz, 2H), 7.87 (s, 1H), 7.66-7.55 (m, 10H), 7.11-7.07 (m, 4H), 7.04 (s, 1H), 6.79 (s, 2H), 5.68 (d, J=16.5 Hz, 1H), 5.27-5.22 (m, 3H), 3.95-3.89 (m, 2H), 3.77 (s, 8H), 3.62 (s, 4H), 3.10-3.08 (m, 4H), 1.90-1.72 (m, 6H), 1.35 (t, J=7.5 Hz, 3H), 0.98 (t, J=7.2 Hz, 3H). Mass: $(EM+2H^+)/2$. found 574.

Compound 8:

$^1$H NMR (400 MHz, $CDCl_3$): δ=8.48 (d, J=4.4 Hz, 4H), 8.38 (s, 1H), 8.04-8.00 (m, 2H), 7.76-7.71 (m, 3H), 7.60-7.57 (m, 4H), 7.54-7.51 (m, 5H), 7.48 (dd, J=9.2, 1.6 Hz, 1H), 7.30 (t, J=8.0 Hz, 1H), 7.11-7.08 (m, 4H), 6.96 (s, 1H), 6.83 (s, 2H), 6.06 (m, 1H), 5.68 (d, J=16.0 Hz, 1H), 5.22 (d, J=16.0 Hz, 1H), 5.19 (d, J=27.2 Hz, 1H), 5.14 (d, J=27.2 Hz, 1H), 3.99 (t, J=6.0 Hz, 2H), 3.76 (s, 8H), 3.60 (s, 4H), 3.39-3.36 (m, 2H), 3.00 (q, J=7.2 Hz, 2H), 1.92-1.81 (m, 4H), 1.74 (q, J=6.8 Hz, 2H), 1.32 (t, J=7.6 Hz, 3H), 0.99 (t, J=7.2 Hz, 3H). Mass: $(EM+2H^+)/2$. found 563.25.

Compound 9:

$^1$H NMR (400 MHz, $CDCl_3$): δ=8.65 (s, 1H), 8.49 (d, J=4.4 Hz, 4H), 8.41 (s, 1H), 8.26 (d, J=8 Hz, 1H), 8.16-8.08 (m, 3H), 8.01 (d, J=8 Hz, 1H), 7.87 (d, J=2.4 Hz, 2H), 7.64-7.51 (m, 8H), 7.14 (t, J=6 Hz, 4H), 7.00 (s, 1H), 6.79 (d, J=4.4 Hz, 2H), 5.45 (dd, J=172, 16.4, 2H), 5.21 (s, 1H), 5.08 (s, 2H), 5.03 (s, 1H), 3.88-3.82 (m, 10H), 3.66 (s, 4H), 3.58-3.46 (m, 4H), 3.25-3.22 (m, 2H), 3.10-2.95 (m, 4H), 2.58-2.51 (m, 2H), 1.94-1.83 (m, 2H), 1.70-1.57 (m, 4H), 1.36 (t, J=8 Hz, 3H), 1.02 (t, J=8 Hz, 3H). Mass: $(EM+2H^+)/2$. found 667.29.

Compound 11:

$^1$H NMR (300 MHz, $CDCl_3$): δ=8.47 (dd, J=5.1, 0.9 Hz, 4H), 8.22-8.19 (m, 2H), 7.85-7.82 (m, 2H), 7.64-7.52 (m, 16H), 7.43-7.30 (m, 6H), 7.11-7.04 (m, 5H), 6.85 (s, 2H), 5.71 (d, J=16.2 Hz, 1H), 5.27 (d, J=16.2 Hz, 1H), 5.22 (s, 2H), 4.68 (s, 4H), 4.05 (m, 2H), 3.76 (s, 8H), 3.61 (4H), 3.57 (m, 2H), 3.09 (q, J=7.5 Hz, 2H), 1.93-1.83 (m, 6H), 1.35 (t, J=7.8 Hz, 3H), 1.02 (t, J=7.5 Hz, 3H). Mass: $(EM+2H^+)/2$. found 646.29.

Compound 12:

¹H NMR (300 MHz, CDCl₃) δ 1.03 (t, J=7.5 Hz, 3H), 1.39 (t, J=7.5 Hz, 3H), 1.85 (m, 6H), 2.58-2.51 (m, 1H), 3.24-3.03 (m, 6H), 3.38-3.29 (m, 1H), 3.52-3.48 (m, 2H), 3.67 (s, 4H), 3.82 (s, 8H), 3.91-3.87 (m, 1H), 4.00 (t, J=4.8 Hz, 2H), 4.69 (d, J=3.0 Hz, 2H), 5.27 (d, J=12.0 Hz, 2H), 5.30 (d, J=16.5 Hz, 1H), 5.74 (d, J=16.2 Hz, 1H), 6.86 (s, 2H), 7.04 (s, 1H), 7.15-7.11 (m, 4H), 7.40-7.36 (m, 2H), 7.71-7.55 (m, 12H), 7.83 (d, J=2.1 Hz, 1H), 8.23 (d, J=9.3 Hz, 1H), 8.49 (d, J=4.8 Hz, 4H). Mass: (EM+2H⁺)/2. found 641.26.

Compound 13:

¹H NMR (300 MHz, CDCl₃) δ 1.06-0.88 (m, 6H), 1.40 (t, J=7.5 Hz, 3H), 1.83-1.65 (m, 4H), 1.97-1.85 (m, 2H), 2.26 (t, J=7.5 Hz, 1H), 2.41 (t, J=7.2 Hz, 1H), 3.16 (m, 2H), 3.35 (m, 1H), 3.49 (m, 1H), 3.65 (s, 2H), 3.67 (s, 2H), 3.80 (s, 8H), 3.96 (m, 2H), 4.68 (s, 1H), 4.72 (s, 1H), 5.27 (s, 2H), 5.31 (d, J=14.1 Hz, 1H), 5.75 (d, J=16.2 Hz, 1H), 6.84 (s, 2H), 7.15-7.07 (m, 5H), 7.41-7.34 (m, 2H), 7.69-7.56 (m, 10H), 7.96-7.94 (m, 1H), 8.18 (d, J=8.4 Hz, 1H), 8.31-8.24 (m, 2H), 8.50 (d, J=4.5 Hz, 4H). Mass: (EM+2H⁺)/2. found 583.27.

Compound 14:

¹H NMR (300 MHz, CDCl₃) δ 1.04 (t, J=7.5 Hz, 3H), 1.40 (t, J=8.1 Hz, 3H), 1.97-1.81 (m, 6H), 3.21-3.13 (m, 2H), 3.60 (t, J=7.2 Hz, 2H), 3.67 (s, 4H), 3.82 (s, 8H), 3.97 (m, 2H), 4.92 (s, 2H), 5.28 (d, J=3.9 Hz, 2H), 5.32 (d, J=13.2 Hz, 1H), 5.76 (d, J=16.2 Hz, 1H), 6.85 (s, 2H), 6.95-6.92 (m, 1H), 7.15-7.10 (m, 5H), 7.41 (d, J=4.8 Hz, 1H), 7.48 (d, J=7.8 Hz, 2H), 7.69-7.56 (m, 11H), 7.96 (m, 1H), 8.31-8.24 (m, 3H), 8.50 (d, J=4.5 Hz, 4H). Mass: (EM+2H⁺)/2. found 603.74.

Compound 15:

¹H NMR (300 MHz, CDCl₃): δ=8.51 (d, J=4.2 Hz, 4H), 8.31-8.16 (m, 3H), 7.98-7.95 (m, 1H), 7.72-7.53 (m, 10H), 7.37 (d, J=8.1 Hz, 2H), 7.18-7.11 (m, 4H), 7.08 (s, 1H), 6.84 (s, 2H), 5.57 (dd, J=133, 16.5 Hz, 2H), 5.28 (s, 2H), 4.69 (d, J=4.8 Hz, 2H), 3.97 (d, J=5.4 Hz, 2H), 3.86-3.72 (m, 10H), 3.70-3.56 (m, 4H), 3.52-3.29 (m, 2H), 3.22-3.13 (m, 2H), 1.96-1.84 (m, 2H), 1.82-1.54 (m, 12H), 1.41 (t, J=7.2 Hz, 3H), 1.30-1.14 (m, 3H), 1.05 (t, J=7.2 Hz, 3H). Mass: (EM+2H⁺)/2. found 603.78.

Compound 16:

¹H NMR (400 MHz, CDCl₃) δ 1.05 (t, J=7.2 Hz, 3H), 1.41 (t, J=7.6 Hz, 3H), 1.96-1.85 (m, 4H), 3.17 (q, J=8.0 Hz, 2H), 3.29 (s, 1H), 3.57 (s, 1H), 3.69 (s, 4H), 3.83 (s, 9H), 4.00 (s, 1H), 4.64 (s, 1H), 4.87 (s, 1H), 5.29 (d, J=5.6 Hz, 2H), 5.32 (d, J=17.2 Hz, 1H), 5.76 (d, J=16 Hz, 1H), 6.81 (s, 1H), 6.86 (s, 1H), 7.15-7.12 (m, 5H), 7.31-7.29 (m, 2H), 7.49 (m, 3H), 7.63-7.57 (m, 9H), 7.69-7.66 (m, 2H), 7.96 (d, J=2.8 Hz, 1H), 8.25 (d, J=8.4 Hz, 2H), 8.30 (d, J=9.2 Hz, 1H), 8.50 (d, J=4.8 Hz, 4H). Mass: (EM+2H⁺)/2. found 639.72.

Compound 17:

¹H NMR (400 MHz, CDCl₃) δ 1.00 (t, J=7.2 Hz, 3H), 1.38 (t, J=7.6 Hz, 3H), 1.63 (m, 1H), 1.81-1.94 (m, 5H), 3.13 (q, J=7.2 Hz, 2H), 3.37 (m, 1H), 3.61 (m, 5H), 3.78 (m, 9H), 4.00 (m, 1H), 4.71 (s, 1H), 4.90 (s, 1H), 5.24 (d, J=8 Hz, 2H), 5.27 (d, J=16 Hz, 1H), 5.70 (d, J=16.4 Hz, 1H), 6.77 (s, 1H), 6.84 (s, 1H), 7.07-7.11 (m, 5H), 7.32-7.38 (m, 4H), 7.50-7.56 (m, 15H), 7.65 (d, J=9.2 Hz, 1H), 7.68 (s, 1H), 7.93 (d, J=2.4 Hz, 1H), 8.23 (d, J=8.4 Hz, 1H), 8.27 (d, J=9.2 Hz, 1H), 8.47 (d, J=4.4 Hz, 4H). Mass: (EM+2H⁺)/2. found 638.83.

Compound 18:

¹H NMR (300 MHz, CDCl₃) δ 1.04 (t, J=7.5 Hz, 3H), 1.37 (t, J=7.8 Hz, 3H), 1.50-1.46 (m, 2H), 1.77 (m, 2H), 1.93-1.83 (m, 2H), 3.16 (q, J=7.5 Hz, 2H), 3.66 (s, 4H), 3.74-3.72 (m, 2H), 3.81 (s, 8H), 4.09-3.96 (m, 4H), 4.82 (d, J=9.3 Hz, 2H), 5.28 (d, J=4.2 Hz, 2H), 5.31 (d, J=14.7 Hz, 1H), 5.75 (d, J=16.2 Hz, 1H), 6.75 (s, 1H), 6.85 (s, 1H), 7.26-7.10 (m, 15H), 7.50 (d, J=7.8 Hz, 2H), 7.68-7.55 (m, 10H), 7.95 (d, J=1.8 Hz, 1H), 8.21-8.17 (m, 2H), 8.29 (d, J=9.0 Hz, 1H), 8.49 (d, J=4.5 Hz, 4H). Mass: (EM+2H⁺)/2. found 645.79.

Compound 19:

¹H NMR (300 MHz, CDCl₃) δ 1.01 (t, J=7.2 Hz, 3H), 1.38 (t, J=7.5 Hz, 3H), 1.74 (m, 2H), 1.93-1.84 (m, 6H), 3.18-3.10 (m, 2H), 3.39-3.44 (m, 2H), 3.64 (s, 4H), 3.78 (s, 8H), 3.94 (t, J=5.7 Hz, 2H), 4.62 (s, 2H), 5.31-5.25 (m, 3H), 5.71 (d, J=16.5 Hz, 1H), 6.81 (s, 2H), 7.13-7.08 (m, 6H), 7.43 (d, J=8.7 Hz, 2H), 7.62-7.54 (m, 8H), 7.65 (d, J=2.4 Hz, 1H), 7.67 (s, 1H), 7.92 (d, J=2.4 Hz, 1H), 8.15 (d, J=2.7 Hz, 1H), 8.20 (d, J=8.1 Hz, 2H), 8.27 (d, J=9.6 Hz, 1H), 8.48 (d, J=4.8 Hz, 4H), 8.64 (d, J=2.7 Hz, 1H). Mass: (EM+2H⁺)/2. found 632.

Compound 20:

¹H NMR (300 MHz, CDCl₃) δ 1.04 (t, J=7.8 Hz, 3H), 1.40 (t, J=7.2 Hz, 3H), 1.77 (m, 2H), 1.95-1.85 (m, 4H), 3.17-3.12 (m, 2H), 3.56 (m, 2H), 3.69 (s, 4H), 3.82 (s, 8H), 3.96 (m, 2H), 4.92 (s, 2H), 5.28 (s, 2H), 5.30 (d, J=16.5 Hz, 1H), 5.74 (d, J=16.5 Hz, 1H), 6.82 (s, 2H), 7.08 (s, 1H), 7.16-7.12 (m, 4H), 7.42 (d, J=7.8 Hz, 2H), 7.67-7.56 (m, 10H), 7.95 (s, 1H), 8.23 (d, J=7.5 Hz, 2H), 8.28 (d, J=9 Hz, 1H), 8.52 (m, 4H), 8.68 (s, 1H). Mass: (EM+2H⁺)/2. found 627.

Compound 21:

¹H NMR (300 MHz, CDCl₃) δ 1.03 (t, J=7.2 Hz, 3H), 1.39 (t, J=7.5 Hz, 3H), 1.96-1.85 (m, 4H), 2.09 (m, 2H), 3.16-3.11 (m, 2H), 3.64 (m, 2H), 3.67 (s, 4H), 3.80 (s, 8H), 4.06 (t, J=6 Hz, 2H), 4.13 (m, 2H), 5.33-5.27 (m, 3H), 5.74 (d, J=16.8 Hz, 1H), 6.17 (d, J=8.4 Hz, 1H), 6.84 (s, 2H), 7.15-7.10 (m, 5H), 7.39 (d, J=8.1 Hz, 2H), 7.66-7.54 (m, 10H), 7.94 (s, 1H), 8.28-8.23 (m, 3H), 8.35 (d, J=9.3 Hz, 1H), 8.48 (d, J=5.1 Hz, 4H). Mass: (EM+2H⁺)/2. found 630.

Compound 22:

¹H NMR (400 MHz, CDCl₃): δ=8.51 (s, 4H), 8.31-8.18 (m, 3H), 7.97-7.94 (m, 1H), 7.72-7.60 (m, 10H), 7.44-7.30 (m, 2H), 7.19-7.07 (m, 5H), 6.86 (s, 2H), 5.54 (dd, J=172, 16.4 Hz, 2H), 5.28 (s, 2H), 4.73 (d, J=16.4 Hz, 2H), 3.99 (s, 2H), 3.83-3.74 (m, 10H), 3.70-3.67 (m, 4H), 3.50 (s, 1H), 3.38 (s, 1H), 3.18 (s, 2H), 2.50-2.42 (m, 2H), 1.97-1.86 (m, 2H), 1.81 (s, 4H), 1.73-1.67 (m, 2H), 1.45-1.39 (m, 3H), 1.32-1.30 (m, 6H), 1.08-1.02 (m, 3H), 0.89-0.87 (m, 314). Mass: (EM+2H⁺)/2. found 604.79.

Compound 23:

¹H NMR (400 MHz, CDCl₃) δ 1.04 (t, J=7.2 Hz, 3H), 1.41 (t, J=7.6 Hz, 3H), 1.59 (m, 1H), 1.76 (m, 1H), 1.96-1.83 (m, 4H), 3.20-3.14 (m, 2H), 3.30 (m, 1H), 3.59 (m, 1H), 3.67 (s, 4H), 3.81 (s, 8H), 3.89-4.02 (m, 2H), 4.66 (s, 1H), 4.90 (s, 1H), 5.28 (d, J=5.6 Hz, 2H), 5.31 (d, J=17.2 Hz, 1H), 5.75 (d, J=16.4 Hz, 1H), 6.78 (s, 1H), 6.86 (s, 1H), 7.14-7.10 (m, 5H), 7.42-7.35 (m, 5H), 7.63-7.57 (m, 10H), 7.69-7.66 (m, 2H), 7.96 (d, J=2.8 Hz, 1H), 8.24 (d, J=8 Hz, 2H), 8.29 (d, J=9.2 Hz, 1H), 8.50 (d, J=4.8 Hz, 4H). Mass: (EM+2H⁺)/2. found 600.76.

Compound 24:

¹H NMR (300 MHz, CDCl₃) δ 1.04 (t, J=7.5 Hz, 3H), 1.44-1.37 (m, 4H), 1.70-1.65 (m, 1H), 1.99-1.86 (m, 4H), 3.19-3.15 (m, 2H), 3.68-3.65 (m, 6H), 3.82-3.80 (m, 10H), 4.09-3.94 (m, 2H), 5.29 (s, 2H), 5.31 (d, J=16.2 Hz, 1H), 5.75 (d, J=16.2 Hz, 1H), 6.68 (s, 1H), 6.90 (s, 1H), 7.14-7.12 (m, 5H), 7.28 (d, J=5.1 Hz, 2H), 7.64-7.39 (m, 12H), 7.72-7.67 (m, 2H), 7.99-7.80 (m, 4H), 8.17 (d, J=8.1 Hz, 1H), 8.32-8.27 (m, 2H), 8.50 (d, J=4.5 Hz, 4H). Mass: (EM+2H⁺)/2. found 625.77.

Compound 25:

¹H NMR (300 MHz, CDCl₃) δ 1.00 (t, J=7.2 Hz, 3H), 1.38 (t, J=7.5 Hz, 3H), 1.60-1.49 (m, 4H), 1.93-1.81 (m, 2H), 2.46 (s, 1H), 2.54 (s, 2H), 3.03 (m, 1H), 3.17-3.10 (m, 2H), 3.44 (m, 1H), 3.64 (s, 4H), 3.78 (s, 8H), 3.86 (m, 2H), 4.50 (s, 1H), 4.72 (s, 1H), 5.25 (d, J=4.2 Hz, 2H), 5.27 (d, J=16.8 Hz, 1H), 5.70 (d, J=16.5 Hz, 1H), 6.80-6.77 (m, 2H), 7.12-7.08 (m, 5H), 7.19-7.17 (m, 1H), 7.35-7.33 (m, 1H), 7.50-7.42 (m, 3H), 7.65-7.54 (m, 11H), 7.68 (s, 1H), 7.92 (d, J=2.4 Hz, 1H), 8.12-8.06 (m, 2H), 8.28 (d, J=9.0 Hz, 1H), 8.47 (d, J=4.8 Hz, 4H). Mass: (EM+2H$^+$)/2. found 658.26.

Compound 26:
$^1$H NMR (300 MHz, CDCl$_3$) δ 1.04 (t, J=7.2 Hz, 3H), 1.29 (m, 2H), 1.40 (t, J=7.5 Hz, 3H), 1.68 (m, 8H), 1.95-1.86 (m, 4H), 2.28 (m, 2H), 2.95 (m, 1H), 3.16 (q, J=7.5 Hz, 2H), 3.30 (m, 1H), 3.67 (s, 4H), 3.81 (s, 8H), 3.91 (m, 2H), 4.22 (s, 1H), 4.65 (s, 1H), 5.28 (d, J=3.6 Hz, 2H), 5.31 (d, J=15.3 Hz, 1H), 5.76 (d, J=16.5 Hz, 1H), 6.81 (s, 2H), 7.15-7.10 (m, 5H), 7.38-7.20 (m, 6H), 7.61-7.56 (m, 8H), 7.69-7.64 (m, 2H), 7.95 (d, J=1.8 Hz, 1H), 8.17 (d, J=7.8 Hz, 2H), 8.29 (d, J=9.3 Hz, 1H), 8.50 (d, J=4.2 Hz, 4H). Mass: (EM+2H$^+$)/2. found 658.28.

Compound 27:
$^1$H NMR (300 MHz, CDCl$_3$) δ 1.04 (t, J=7.2 Hz, 3H), 1.41 (t, J=7.5 Hz, 3H), 1.77-1.60 (m, 2H), 1.93-1.84 (m, 4H), 3.17 (q, J=7.2 Hz, 2H), 3.27 (m, 1H), 3.61 (m, 1H), 3.66 (s, 4H), 3.81 (s, 8H), 4.01-3.94 (m, 2H), 4.61 (s, 1H), 4.90 (s, 1H), 5.28 (s, 2H), 5.31 (d, J=15.3 Hz, 1H), 5.75 (d, J=16.2 Hz, 1H), 6.79 (s, 1H), 6.85 (s, 1H), 7.14-7.10 (m, 5H), 7.69-7.55 (m, 16H), 7.96 (s, 1H), 8.25 (d, J=7.5 Hz, 2H), 8.30 (d, J=9.0 Hz, 1H), 8.50 (d, J=4.8 Hz, 4H). Mass: (EM+2H$^+$)/2. found 634.76.

Compound 28:
$^1$H NMR (300 MHz, CDCl$_3$): δ=8.49 (dd, J=4.5, 0.9 Hz, 4H), 8.16 (d, J=9.3 Hz, 1H), 7.78 (d, J=2.1 Hz, 1H), 7.63-7.50 (m, 10H), 7.13-7.09 (m, 4H), 7.06 (s, 1H), 6.85 (s, 2H), 5.85 (t, J=6.0 Hz, 1H), 5.72 (d, J=16.2 Hz, 1H), 5.28 (d, J=16.2 Hz, 1H), 5.17 (s, 2H), 4.01 (t, J=5.4 Hz, 2H), 3.80 (s, 8H), 3.65 (s, 4H), 3.40 (q, J=6.0 Hz, 2H), 3.07 (q, J=7.5 Hz, 2H), 1.95-1.82 (m, 6H), 1.34 (t, J=7.5 Hz, 3H), 1.01 (t, J=7.2 Hz, 3H). Mass: (EM+2H$^+$)/2. found 504.

Compound 29:
$^1$H NMR (300 MHz, CDCl$_3$): δ=8.48 (d, J=4.8 Hz, 4H), 8.19 (d, J=9.0 Hz, 1H), 7.85-7.55 (m, 12H), 7.12-7.08 (m, 5H), 6.79 (s, 2H), 5.71 (dd, J=16.5, 7.2 Hz, 1H), 5.29 (d, J=16.5 Hz, 1H), 5.21 (d, J=7.8 Hz, 2H), 3.92 (m, 1H), 3.78-3.74 (m, 11H), 3.63-3.59 (m, 5H), 3.36-3.34 (m, 2H), 3.11-3.08 (m, 2H), 2.40-1.72 (m, 10H), 1.37-1.32 (m, 3H), 1.04 (t, J=7.2 Hz, 3H). Mass: (EM+2H$^+$)/2. found 552.

Compound 31:
$^1$H NMR (400 MHz, CDCl$_3$): δ=8.49 (d, J=4.4 Hz, 4H), 8.23 (dd, J=9.2, 5.2 Hz, 1H), 7.88-7.56 (m, 15H), 7.45-7.41 (m, 4H), 7.35 (t, J=6.4 Hz, 1H), 7.11-7.08 (m, 5H), 6.84 (s, 1H), 6.79 (s, 1H), 5.73 (d, J=16.0 Hz, 1H), 5.30 (d, J=16.0 Hz, 1H), 5.24 (s, 2H), 4.79 (s, 1H), 4.68 (s, 1H), 3.99 (t, J=5.6 Hz, 2H), 3.80-3.77 (m, 8H), 3.64-3.61 (m, 4H), 3.58-3.54 (m, 2H), 3.12-3.10 (m, 2H), 1.89-1.88 (m, 6H), 1.38-1.33 (m, 3H), 1.04-1.01 (m, 3H). Mass: (EM+2H$^+$)/2. found 586.77.

Compound 32:
$^1$H NMR (400 MHz, CDCl$_3$): δ=8.48 (d, J=4.8 Hz, 4H), 8.15 (t, J=8.0 Hz, 1H), 7.77 (s, 1H), 7.62-7.54 (m, 10H), 7.11 (t, J=6.0 Hz, 4H), 7.05 (s, 1H), 6.82 (s, 2H), 6.13-6.09 (m, 1H), 5.69 (d, J=16.4 Hz, 1H), 5.26 (d, J=16.4 Hz, 1H), 5.20 (s, 2H), 4.36 (d, J=12.8 Hz, 1H), 4.25 (d, J=12.0 Hz, 1H), 3.96 (t, J=5.6 Hz, 2H), 3.78 (s, 8H), 3.63 (s, 4H), 3.34 (q, J=6.4 Hz, 2H), 3.13-3.04 (m, 3H), 2.87 (t, J=11.2 Hz, 1H), 2.33-2.28 (m, 1H), 1.93-1.79 (m, 8H), 1.71 (q, J=7.6 Hz, 2H), 1.37 (t, J=7.6 Hz, 3H), 0.99 (t, J=7.2 Hz, 3H). Mass: (EM+2H$^+$)/2. found 559.26.

Compound 33:
$^1$H NMR (300 MHz, CDCl$_3$): δ=8.47 (d, J=4.8 Hz, 4H), 8.20 (d, J=9.0 Hz, 1H), 7.80-7.78 (m, 1H), 7.64-7.49 (m, 10H), 7.47-7.41 (m, 1H), 7.10 (t, J=6.0 Hz, 4H), 7.04 (s, 1H), 6.78 (s, 2H), 5.69 (d, J=16.5 Hz, 1H), 5.27 (d, J=16.5 Hz, 1H), 5.22 (s, 2H), 3.91 (m, 2H), 3.82 (m, 2H), 3.76 (s, 8H), 3.72-3.68 (m, 4H), 3.61 (s, 6H), 3.31-3.27 (m, 2H), 3.11 (q, J=7.2 Hz, 2H), 2.47-2.44 (m, 2H), 2.35-2.33 (m, 2H), 2.05-1.95 (m, 2H), 1.92-1.83 (m, 2H), 1.81-1.76 (m, 2H), 1.66 (m, 2H), 1.36 (t, J=7.5 Hz, 3H), 1.12-1.09 (m, 6H), 0.99 (t, J=7.5 Hz, 3H). Mass: (EM+2H$^+$)/2. found 615.80.

Compound 34:
$^1$H NMR (400 MHz, CDCl$_3$): δ=8.38 (d, J=4.0 Hz, 4H), 7.74-7.71 (m, 4H), 7.62-7.58 (m, 7H), 7.35 (dd, J=7.2, 2.4 Hz, 1H), 7.24-7.21 (m, 4H), 6.89 (s, 1H), 6.58 (s, 2H), 5.35 (m, 1H), 4.97 (m, 1H), 4.73 (s, 2H), 4.25-4.24 (m, 1H), 4.13-4.10 (m, 1H), 3.91 (s, 3H), 3.76 (t, J=5.6 Hz, 2H), 3.68 (s, 8H), 3.61 (m, 1H), 3.49 (s, 4H), 3.20-3.17 (m, 1H), 3.08-3.03 (m, 1H), 2.94 (d, J=18.4 Hz, 1H), 2.80 (d, J=18.4 Hz, 1H), 2.49-2.30 (m, 6H), 2.10-1.93 (m, 2H), 1.71-1.53 (m, 4H), 1.25 (d, J=6.8 Hz, 3H). Mass: (EM+2H$^+$)/2. found 605.

Compound 35:
$^1$H NMR (400 MHz, CDCl$_3$): δ=8.49 (d, J=4 Hz, 4H), 8.18 (d, J=9.2 Hz, 1H), 7.79 (s, 1H), 7.68-7.41 (m, 11H), 7.15-7.06 (m, 6H), 5.52 (dd, J=175.6, 16.4 Hz, 2H), 5.22 (s, 2H), 4.14 (s, 2H), 3.96 (s, 4H), 3.83-3.73 (m, 8H), 3.48 (s, 2H), 3.09-3.07 (m, 2H), 1.94-1.86 (m, 2H), 1.34 (t, J=7.6 Hz, 3H), 1.019 (t, J=7.6 Hz, 3H). Mass: (EM+2H$^+$)/2. found 510.

Compound 36:
$^1$H NMR (400 MHz, CDCl$_3$): δ=8.68 (s, 1H), 8.49 (d, J=4.4 Hz, 4H), 8.24 (t, J=8 Hz, 2H), 8.09 (d, J=8 Hz, 1H), 7.87 (d, J=2 Hz, 1H), 7.67 (s, 1H), 7.58-7.43 (m, 10H), 7.11-7.04 (m, 6H), 5.54 (dd, J=178.6, 16 Hz, 2H), 5.27 (s, 2H), 3.83-3.76 (m, 11H), 3.49 (s, 3H), 3.15 (q, J=7.6 Hz, 2H), 2.90 (t, J=6.4 Hz, 2H), 1.95-1.84 (m, 2H), 1.38 (t, J=7.6 Hz, 3H), 1.06 (t, J=7.6 Hz, 3H). Mass: (EM+2H$^+$)/2. found 542.

Compound 37:
$^1$H NMR (300 MHz, CDCl$_3$): δ=8.50-8.48 (m, 4H), 8.31-8.24 (m, 3H), 7.97 (s, 1H), 7.70-7.52 (m, 12H), 7.16-7.10 (m, 6H), 7.06 (s, 1H), 7.04 (s, 1H), 6.78 (s, 2H), 6.05 (s, 1H), 5.76 (d, J=16.5 Hz, 1H), 5.34-5.28 (m, 3H), 4.74 (s, 2H), 4.04 (m, 2H), 3.77 (s, 8H), 3.59 (s, 4H), 3.55 (m, 2H), 3.17 (q, J=7.5 Hz, 2H), 2.54 (q, J=7.5 Hz, 4H), 1.97-1.84 (m, 6H), 1.41 (t, J=7.8 Hz, 3H), 1.12 (t, J=7.5 Hz, 6H), 1.04 (t, J=7.2 Hz, 3H). Mass: (EM+2H$^+$)/2. found 636.

Compound 38:
$^1$H NMR (300 MHz, CDCl$_3$) δ 1.04 (t, J=7.5 Hz, 3H), 1.32-1.25 (m, 2H), 1.40 (t, J=7.5 Hz, 3H), 1.63 (m, 6H), 1.93-1.85 (m, 6H), 2.22-2.17 (m, 2H), 2.90 (m, 1H), 3.20-3.15 (m, 3H), 3.88-3.67 (m, 26H), 4.09 (s, 1H), 4.54 (s, 1H), 5.28 (d, J=10.5 Hz, 2H), 5.31 (d, J=12.0 Hz, 1H), 5.75 (d, J=16.2 Hz, 1H), 6.77 (s, 2H), 6.97 (m, 1H), 7.26-7.11 (m, 10H), 7.72-7.55 (m, 12H), 7.99-7.96 (m, 3H), 8.29-8.26 (m, 3H), 8.49 (d, J=4.8 Hz, 4H). Mass: (EM+2H$^+$)/2. found 798.

Compound 39:
$^1$H NMR (400 MHz, CDCl$_3$): δ=1.03 (t, J=7.2 Hz, 3H), 1.25 (m, 1H), 1.39 (t, J=7.6 Hz, 31-1), 1.65-1.96 (m, 11H), 2.01 (m, 2H), 2.24 (m, 2H), 3.13-3.19 (m, 3H), 3.44-3.54 (m, 5H), 3.59-3.64 (m, 12H), 3.77 (s, 8H), 3.97 (t, J=5.6 Hz, 2H), 4.30 (s, 1H), 4.67 (s, 1H), 5.27 (d, J=12.4 Hz, 2H), 5.30 (d, J=16.0 Hz, 1H), 5.74 (d, J=16.0 Hz, 1H), 6.80 (s, 2H), 7.05 (s, 1H), 7.09-7.12 (m, 5H), 7.20-7.30 (m, 5H), 7.54-7.62 (m, 8H), 7.65-7.68 (m, 2H), 7.76 (m, 4H), 7.94 (d, J=2.4 Hz, 1H), 8.13 (d, J=6.8 Hz, 2H), 8.28 (d, J=9.2 Hz, 1H), 8.48 (d, J=4.8 Hz, 4H). Mass: (EM+2H$^+$)/2. found 798.

Compound 40:
$^1$H NMR (300 MHz, CDCl$_3$): δ=1.04 (t, J=7.2 Hz, 3H), 1.25-1.29 (m, 1H), 1.39 (t, J=7.2 Hz, 3H), 1.66-1.97 (m, 9H), 2.17-2.26 (m, 3H), 2.75 (m, 1H), 3.12-3.20 (m, 3H), 3.39 (m, 1H), 3.74-3.86 (m, 12H), 4.10 (s, 1H), 4.72 (s, 1H), 5.27-5.34

(m, 3H), 5.75 (d, J=16.5 Hz, 1H), 6.99 (s, 2H), 7.12-7.14 (m, 4H), 7.20-7.31 (m, 6H), 7.44-7.46 (m, 4H), 7.55-7.60 (m, 4H), 7.64-7.67 (m, 3H), 7.93 (s, 1H), 8.10-8.18 (m, 2H), 8.28 (d, J=9.3 Hz, 1H), 8.51 (m, 4H). Mass: (EM+2H$^+$)/2. found 645.

Compound 41:
$^1$H NMR (CDCl$_3$, 400 MHz): δ=1.12 (s, 3H), 1.21 (s, 3H), 1.68 (s, 3H), 1.91 (s, 3H), 1.63-2.33 (m, 4H), 2.26 (s, 3H), 2.41 (s, 3H), 2.38-2.58 (m, 8H), 2.72 (t, J=6.8 Hz, 2H), 3.18-3.27 (m, 2H), 3.64 (s, 4H), 3.78 (s, 8H), 3.94 (t, J=6.0 Hz, 2H), 4.19 (d, J=8.4 Hz, 1H), 4.30 (d, J=8.4 Hz, 1H), 4.43 (dd, J=10.8, 6.8 Hz, 1H), 4.96 (d, J=9.2 Hz, 1H), 5.67 (d, J=7.2 Hz, 1H), 5.88-5.93 (m, 2H), 6.20 (t, J=9.2 Hz, 1H), 6.29 (s, 1H), 6.81 (s, 2H), 7.06 (s, 1H), 7.06-7.12 (m, 4H), 7.27-7.63 (m, 24H), 7.79 (d, J=5.6 Hz, 2H), 8.13 (d, J=5.6 Hz, 2H), 8.48 (d, J=4.8 Hz, 4H). Mass: (EM+2H$^+$)/2. found 762.

Compound 42:
$^1$H NMR (CDCl$_3$, 400 MHz): δ=0.98 (t, J=7.2 Hz, 3H), 1.22 (m, 8H), 1.38 (t, J=7.6 Hz, 3H), 1.88 (m, 2H), 2.01 (s, 5H), 2.10-2.41 (m, 8H), 2.85 (s, 1H), 2.92 (s, 1H), 3.15 (m, 3H), 3.44 (s, 2H), 3.50-3.71 (m, 13H), 3.76 (s, 8H), 3.86 (s, 2H), 4.10 (dd, J=7.2 Hz, 4H), 4.32 (s, 2H), 4.53 (s, 1H), 5.24 (s, 2H), 5.30 (d, J=16 Hz, 1H), 5.73 (d, J=16 Hz, 1H), 6.75 (s, 3H), 6.95 (br, 2H), 7.1-7.25 (m, 13H), 7.29 (d, J=8.4 Hz, 2H), 7.52-7.64 (m, 8H), 7.64-7.72 (m, 3H), 7.93 (d, J=2.4 Hz, 1H), 8.14 (d, J=7.2 Hz, 2H), 8.27 (d, J=9.2 Hz, 1H), 8.47 (d, J=8.8 Hz, 4H). Mass: (EM+2H$^+$)/2. found 901.6.

Compound 43:
$^1$H NMR (CDCl$_3$, 400 MHz): δ=1.12 (s, 3H), 1.20 (s, 3H), 1.67 (s, 3H), 1.93 (s, 3H), 2.16 (s, 3H), 2.37 (s, 3H), 2.21-2.76 (m, 8H), 2.97 (d, J=6.8 Hz, 1H), 3.36-3.41 (m, 1H), 3.54-3.62 (m, 1H), 3.71 (t, J=4.4 Hz, 4H), 3.78 (s, 4H), 3.84 (s, 8H), 4.16-4.20 (m, 3H), 4.41-4.57 (m, 3H), 4.70 (s, 1H), 4.94 (d, J=9.2 Hz, 1H), 5.66 (dd, J=6.8, 3.6 Hz, 1H), 5.86-5.90 (m, 1H), 6.17 (q, J=9.2 Hz, 1H), 6.31 (d, J=4.4 Hz, 1H), 6.95 (s, 1H), 7.00 (s, 1H), 7.03-7.09 (m, 4H), 7.19-7.63 (m, 34H), 7.80 (dd, J=17.6, 7.2 Hz, 2H), 8.12 (m, 2H), 8.47 (d, J=4.8 Hz, 4H). Mass: (EM+2H$^+$)/2. found 831.

Compound 44:
$^1$H NMR (400 MHz, CDCl$_3$): δ=1.05 (t, J=7.2 Hz, 3H), 1.40 (t, J=7.6 Hz, 3H), 1.85-1.96 (m, 6H), 3.14-3.54 (m, 2H), 3.52-3.57 (m, 2H), 3.65 (s, 4H), 3.80 (s, 8H), 4.057-4.10 (m, 2H), 5.27 (s, 2H), 5.29 (d, J=16.0 Hz, 1H), 5.73 (d, J=16.0 Hz, 1H), 6.88 (s, 2H), 6.99 (d, J=8.4 Hz, 2H), 7.07-7.12 (m, 2H), 7.28-7.66 (m, 18H), 7.93 (d, J=2.8 Hz, 1H), 8.07 (d, J=8.4 Hz, 2H), 8.26 (d, J=9.2 Hz, 1H), 8.48 (d, J=4.8 Hz, 4H). Mass: (EM+2H$^+$)/2. found 661.4.

Compound 45:
$^1$H NMR (CDCl$_3$, 300 MHz): δ=1.11 (s, 3H), 1.18 (s, 3H), 1.66 (s, 3H), 1.89 (s, 3H), 2.18 (s, 3H), 2.27 (s, 3H), 2.02-2.57 (m, 7H), 2.68 (t, J=6.6 Hz, 2H), 2.79 (t, J=5.7 Hz, 2H), 3.25 (q, J=4.8 Hz, 2H), 3.40 (t, J=5.1 Hz, 2H), 3.54-3.63 (m, 10H), 3.70 (t, J=4.5 Hz, 4H), 3.77 (s, 4H), 3.81 (s, 8H), 4.18 (d, J=8.8 Hz, 1H), 4.28 (d, J=8.8 Hz, 1H), 4.39-4.47 (m, 3H), 4.94 (d, J=9.0 Hz, 1H), 5.43 (d, J=3.6 Hz, 1H), 5.66 (d, J=6.6 Hz, 1H), 5.90 (dd, J=8.4, 3.6 Hz, 1H), 6.16 (t, J=9.0 Hz, 1H), 6.28 (s, 1H), 7.06-7.09 (m, 8H), 7.22-7.61 (m, 33H), 7.79 (dd, J=7.5 Hz, 2H), 8.11 (dd, J=7.5 Hz, 2H), 8.46 (d, J=4.5 Hz, 4H). Mass: (EM+2H$^+$)/2. found 978.

Compound 46:
$^1$H NMR (400 MHz, CDCl$_3$): δ=1.12 (s, 3H), 1.19 (s, 3H), 1.68 (s, 3H), 1.87-1.88 (m, 1H), 1.90 (s, 3H), 2.07-2.13 (m, 1H), 2.20 (s, 3H), 2.28-2.35 (m, 1H), 2.42 (s, 3H), 2.56 (t, J=6.8 Hz, 2H), 2.66-2.67 (m, 1H), 2.80 (t, J=6.8 Hz, 2H), 3.25-3.31 (m, 2H), 3.79-3.96 (m, 18H), 4.11 (s, 2H), 4.20 (d, J=8.8 Hz, 2H), 4.22-4.28 (m, 2H), 4.31 (d, J=8 Hz, 1H), 4.40-4.45 (m, 1H), 4.95 (d, J=8.4 Hz, 1H), 5.48 (d, J=3.6 Hz, 1H), 5.68 (d, J=6.8 Hz, 1H), 5.94 (dd, J=8.4, 3.6 Hz, 1H), 6.22 (t, J=8.8 Hz, 1H), 6.27 (s, 1H), 6.89 (d, J=8.4 Hz, 2H), 7.08-7.13 (m, 4H), 7.20 (d, J=7.6 Hz, 2H), 7.27-7.66 (m, 21H), 7.77 (d, J=7.2 Hz, 2H), 8.14 (d, J=7.2 Hz, 2H), 8.41 (d, J=4.8 Hz, 2H), 8.49 (d, J=4.8 Hz, 2H). Mass: (EM+2H$^+$)/2. found 857.8.

Compound 47:
$^1$H NMR (400 MHz, CDCl$_3$): δ=1.04 (t, J=7.2 Hz, 3H), 1.30 (s, 9H), 1.44 (t, J=7.6 Hz, 3H), 1.86-1.97 (m, 4H), 2.03-2.08 (m, 2H), 3.18-3.24 (m, 2H), 3.36-3.40 (m, 2H), 3.85 (s, 4H), 3.95 (s, 6H), 4.26 (s, 2H), 5.30-5.34 (m, 3H), 5.78 (d, 1.04, J=3.6 Hz, 3H), 7.09-7.13 (m, 2H), 7.17-7.21 (m, 2H), 7.5 (d, J=8 Hz, 2H), 7.60-7.76 (m, 9H), 7.84 (d, J=8.8 Hz, 2H), 8.0 (d, J=2.4 Hz, 1H), 8.28-8.32 (m, 4H), 8.48 (d J=7.6 Hz, 2H), 8.55 (d, J=6.8 Hz, 2H). Mass: (EM+2H$^+$)/2. found 626.8.

Compound 48:
$^1$H NMR (CDCl$_3$, 400 MHz): δ=0.88 (m, 6H), 1.03 (t, J=6.8 Hz, 3H), 1.39 (t, J=7.2 Hz, 3H), 1.90 (m, 2H), 2.23 (br, 5H), 2.93 (br, 2H), 3.13 (m, 3H), 3.25 (s, 2H), 3.41-3.78 (m, 21H), 3.91 (m, 2H), 4.11 (s, 2H), 4.33 (s, 2H), 4.56 (s, 2H), 5.25 (s, 2H), 5.32 (d, J=18.4 Hz, 1H), 5.76 (d, J=16.4 Hz, 1H), 6.74 (s, 2H), 6.98 (s, 2H), 7.04-7.51 (m, 30H), 7.69 (m, 4H), 7.95 (s, 2H), 8.17 (d, J=6 Hz, 2H), 8.30 (d, J=8.8 Hz, 1H).

Compound 49:
$^1$H NMR (300 MHz, CDCl$_3$): δ=1.05 (t, J=7.2 Hz, 3H), 1.25 (m, 3H), 1.41 (t, J=7.5 Hz, 3H), 1.69 (m, 11H), 1.83-2.02 (m, 4H), 2.27 (m, 2H), 2.84 (m, 1H), 3.00 (d, J=5.7 Hz, 2H), 3.14-3.21 (m, 3H), 3.64 (s, 3H), 3.76 (s, 4H), 3.84 (s, 8H), 4.15 (s, 1H), 4.57 (s, 1H), 4.74-4.80 (m, 1H), 5.29 (d, J=4.8 Hz, 2H), 5.32 (d, J=14.7 Hz, 1H), 5.76 (d, J=16.5 Hz, 1H), 6.95 (s, 2H), 7.10-7.14 (m, 4H), 7.18-7.33 (m, 6H), 7.43-7.46 (m, 4H), 7.57-7.62 (m, 4H), 7.67-7.70 (m, 2H), 7.96 (d, J=2.1 Hz, 1H), 8.17 (d, J=8.1 Hz, 2H), 8.29 (d, J=9.0 Hz, 1H), 8.52 (d, J=5.1 Hz, 4H). Mass: (EM+2H$^+$)/2. found 730.

Compound 50:
$^1$H NMR (CDCl$_3$, 400 MHz): δ=0.88 (m, 2H), 1.13 (s, 3H), 1.21 (s, 3H), 1.22-1.30 (m, 4H), 1.68 (s, 3H), 1.69-1.91 (m, 6H), 1.91 (s, 3H), 2.05-2.32 (m, 2H), 2.21 (s, 3H), 2.42 (s, 3H), 2.55-2.97 (m, 6H), 2.76 (t, J=6.8 Hz, 2H), 3.14-3.54 (m, 8H), 3.64 (s, 4H), 3.67 (s, 8H), 3.86 (t, J=5.6 Hz, 2H), 3.95 (t, J=6.0 Hz, 2H), 4.10-4.12 (m, 2H), 4.09 (d, J=4.4 Hz, 1H), 4.19 (d, J=4.4 Hz, 1H), 4.29-4.45 (m, 3H), 4.95-4.97 (m, 1H), 5.45 (d, J=4.0 Hz, 1H), 5.67 (d, J=7.2 Hz, 1H), 5.92 (dd, J=8.4, 4.0 Hz, 1H), 6.19 (t, J=9.2 Hz, 1H), 6.29 (s, 1H), 6.43-6.45 (m, 1H), 6.82 (s, 2H), 6.82-7.14 (m, 5H), 7.27-7.63 (m, 26H), 7.80 (d, J=7.2 Hz, 2H), 8.13 (d, J=7.2 Hz, 2H), 8.50 (d, J=4.8 Hz, 4H). Mass: (EM+2H$^+$)/2. found 937.

Compound 51:
$^1$H NMR (300 MHz, CDCl$_3$): δ=1.05 (t, J=7.2 Hz, 3H), 1.25-1.40 (m, 12H), 1.83-1.91 (m, 6H), 3.16-3.23 (m, 2H), 3.47-4.05 (m, 28H), 4.55 (s, 2H), 4.77 (s, 2H), 5.28-5.34 (m, 3H), 5.76 (d, J=16.2 Hz, 1H), 6.86 (s, 2H), 7.01-7.13 (m, 5H), 7.60-7.66 (m, 16H), 7.96 (d, J=2.4 Hz, 1H), 8.08 (d, J=8.7 Hz, 2H), 8.28 (d, J=9.3 Hz, 1H), 8.48 (d, J=4.2 Hz, 4H). Mass: (EM+2H$^+$)/2. found 760.4.

Zn-DPA conjugates of each of the compounds described above, denoted as Zn-DPA-(Compound number), were prepared following the procedure described below. More specifically, each of Compounds 1-51 was mixed with 2 molar equivalents of zinc nitrate in a solution containing a solvent mixture of dichloromethane and methanol (1:1) at room temperature and stirred for one hour. Removal of the solvent under vacuum yielded the corresponding Zn-DPA conjugate. The analytical data of several Zn-DPA conjugates are shown below as representative examples:

Zn-DPA-(8):

$^1$H NMR (700 MHz, DMSO-d$_6$): δ=0.86 (t, J=7.0 Hz, 3H), 1.25 (t, J=7.7 Hz, 3H), 1.66 (p, J=7.7 Hz, 2H), 1.79-1.89 (m, 4H), 3.16 (q, J=7.7 Hz, 2H), 3.20 (q, J=7.7 Hz, 2H), 3.75 (d, J=16.1 Hz, 4H), 3.84 (s, 4H), 4.11 (br, 2H), 4.33 (d, J=16.1 Hz, 4H), 5.31 (s, 2H), 5.41 (s, 2H), 6.48 (br, 1H), 6.51 (s, 1H), 6.86 (s, 1H), 6.99 (s, 2H), 7.02 (s, 1H), 7.44 (t, J=7.7 Hz, 1H), 7.54 (d, J=7.7 Hz, 4H), 7.60 (t, J=7.0 Hz, 4H), 7.65 (d, J=7.7 Hz, 1H), 7.71 (d, J=7.7 Hz, 1H), 7.65 (dd, J=9.1, 2.1 Hz, 2H), 8.05 (t, J=7.7 Hz, 4H), 8.14 (s, 1H), 8.21 (d, J=9.1 Hz, 1H), 8.37 (s, 1H), 8.63 (d, J=5.6 Hz, 3H), 8.95 (s, 1H). Mass: (EM+Zn+2H$^+$)/2. found 595, (EM+2Zn+2H$^+$)/2. found 627.

Zn-DPA-(11):

$^1$H NMR (700 MHz, DMSO-d$_6$): δ=0.86 (t, J=7.0 Hz, 3H), 1.25 (t, J=7.7 Hz, 3H), 1.79-1.88 (m, 6H), 3.16 (q, J=7.7 Hz, 2H), 3.48 (s, 2H), 3.73 (d, J=16.1 Hz, 4H), 3.81 (br, 4H), 4.10 (br, 1H), 4.32 (d, J=16.1 Hz, 4H), 4.73 (s, 2H), 5.32 (s, 2H), 5.41 (s, 2H), 6.52 (s, 1H), 6.86 (s, 1H), 6.98 (s, 2H), 7.29-7.31 (m, 1H), 7.37 (d, J=7.7 Hz, 2H), 7.40 (t, J=7.7 Hz, 4H), 7.47 (t, J=7.7 Hz, 2H), 7.52 (d, J=7.7 Hz, 4H), 7.58-7.62 (m, 6H), 7.61 (d, J=7.7 Hz, 2H), 7.76 (t, J=7.7 Hz, 2H), 7.93 (d, J=9.1 Hz, 1H), 8.03 (t, J=7.7 Hz, 4H), 8.20 (d, J=5.6 Hz, 1H), 8.42 (s, 1H), 8.63 (d, J=5.6 Hz, 4H), 8.84 (br, 1H). Mass: (EM+Zn+2H$^+$)/2. found 678, (EM+2Zn+2H$^+$)/2. found 710.

Zn-DPA-(17):

$^1$H NMR (700 MHz, DMSO-d$_6$): δ=0.85 (t, J=7.0 Hz, 3H), 1.25 (t, J=7.7 Hz, 3H), 1.74-1.88 (m, 6H), 3.15 (q, J=7.7 Hz, 3H), 3.53 (s, 1H), 3.69-3.83 (m, 8H), 3.94 (br, 1H), 4.16 (br, 1H), 4.30-4.38 (m, 4H), 4.73 (s, 1H), 4.88 (s, 1H), 5.30 (s, 2H), 5.40 (s, 2H), 6.51 (s, 1H), 6.54-6.88 (m, 2H), 6.93 (s, 1H), 7.02 (s, 1H), 7.30-7.64 (m, 17H), 7.68 (d, J=7.7 Hz, 2H), 7.75 (d, J=9.1 Hz, 1H), 8.05 (t, J=7.7 Hz, 4H), 8.15 (s, 1H), 8.18-8.21 (m, 3H), 8.64 (d, J=5.6 Hz, 4H). Mass: (EM+Zn+2H$^+$)/2. found 670, (EM+2Zn+2H$^+$)/2. found 702.

Zn-DPA-(31):

$^1$H NMR (700 MHz, DMSO-d$_6$): δ=0.85 (t, J=7.0 Hz, 3H), 1.19 (t, J=7.0 Hz, 2H), 1.24 (t, J=7.7 Hz, 1H), 1.82-1.84 (m, 6H), 3.07-3.15 (m, 2H), 3.50 (br, 1H), 3.60 (br, 1H), 3.71 (t, J=17.5 Hz, 4H), 3.81 (s, 4H), 4.12-4.14 (m, 2H), 4.31 (t, J=14.7 Hz, 4H), 4.65 (s, 1H), 4.82 (s, 1H), 5.29 (s, 2H), 5.41 (s, 2H), 6.51 (s, 1H), 6.86 (s, 1H), 6.99 (s, 2H), 7.26-7.72 (m, 20H), 7.72 (d, J=7.7 Hz, 1H), 8.03 (t, J=7.7 Hz, 3H), 8.13 (t, J=7.7 Hz, 1H), 8.63 (d, J=4.9 Hz, 4H). Mass: (EM+Zn+2H$^+$)/2. found 618, (EM+2Zn+2H$^+$/2. found 650.

Plasma Stability of Zn-DPA Conjugates

Zn-DPA conjugates, Zn-DPA-(8), Zn-DPA-(12), Zn-DPA-(25), Zn-DPA-(26), and Zn-DPA-(42) prepared from the corresponding compounds 8, 12, 25, 26, and 42, respectively, were incubated in mouse plasma at 37° C. for up to 24 hours to assess the stability of these conjugates.

A sample was analyzed with a High Performance Liquid Chromatography system to determine the concentration of a test conjugate at one of four time points (i.e., 0, 3 hours, 6 hours, and 24 hours). The percentages of the test conjugate remaining at 3, 6, and 24 hours after incubation in the plasma were determined. The results are shown in Table 1 below. A higher percentage indicates greater stability. Among the five test conjugates, Zn-DPA-(26) and Zn-DPA-(42) prepared from Compounds 26 and 42, respectively, were the most stable. After 24 hours of incubation, it was found that 95% or higher of these conjugates remained in the plasma.

TABLE 1

Stability (percentage remaining) of Zn-DPA conjugates, Zn-DPA-(8), Zn-DPA-(12), Zn-DPA-(25), Zn-DPA-(26), and Zn-DPA-(42)

| Zn conjugates | time = 0 | time = 3 hr | time = 6 hr | time = 24 hr |
|---|---|---|---|---|
| Zn-DPA-(8) | 100 | 90 | 82 | — |
| Zn-DPA-(12) | 100 | 84 | 76 | — |
| Zn-DPA-(25) | 100 | 90 | 85 | — |
| Zn-DPA-(26) | 100 | 99 | 97 | 95 |
| Zn-DPA-(42) | 100 | 99 | 98 | 97 |

Growth Inhibition of Cancer Cells

Cell Culture

SCM-1, MiaPaca2 and Colo205 cells were grown in RPMI 1640 (Roswell Park Memorial Institute) medium (RPMI; Gibco), supplemented with 10% fetal bovine serum (FBS; Gibco). Detroit551 cells were grown in Dulbecco's modified Eagle's medium (DMEM) supplemented with 10% FBS 50 U/mL of penicillin and streptomycin, and 1% Nonessential amino acids (NEAA; Gibco).

Zn-DPA conjugates, Zn-DPA-(8), Zn-DPA-(12), Zn-DPA-(25), Zn-DPA-(26), and Zn-DPA-(42) prepared from the corresponding compounds 8, 12, 25, 26, and 42, respectively, were used to inhibit the growth of human cancer cells (SCM-1, Colo205, MiaPaca2) and human embryonic skin fibroblast cells Detroit551 following the procedures described below.

Cell Viability Assay

Cell viability was examined by the MTS assay (Promega, Madison, Wis., USA). More specifically, cells were grown (2500~3000 cells/well) in a flat bottomed 96-well plate for 24 hours. A medium was added along with a test compound at a pre-determined concentration. The cells were further incubated for 72 hours. At the end of the incubation, the medium was removed and diluted with 100 μl of a 3-(4,5-dimethylthiazol-2-yl)-5-(3-carboxymethoxyphenyl)-2-(4-sulfophenyl)-2H-tetrazolium/phenazine methosulfate mixture. The cells were again incubated for 1.5 hours at 37° C. in a humidified incubator with 5% CO$_2$ to allow viable cells to convert the tetrazolium salt into formazan. The conversion was determined by measuring the absorbance at 490 nm using a BioTek PowerWave-X Absorbance Microplate Reader.

The data obtained were normalized using a vehicle (dimethyl sulfoxide, DMSO)-treated control (100% viability) and a background control (0% viability) to verify growth inhibition. The IC$_{50}$ value is defined as the concentration of a compound that induces a 50% reduction in cell viability in comparison with a vehicle-treated control. These values were calculated using GraphPad Prism version 4 software (San Diego, Calif., USA).

The IC$_{50}$ values for five Zn-DPA conjugates, i.e., Zn-DPA-(8), Zn-DPA-(12), Zn-DPA-(25), Zn-DPA-(26), and Zn-DPA-(42), were shown in Table 2 below. Also shown in this table are IC$_{50}$ values for two anticancer compounds, i.e., SN-38 and CPT-11, for comparison. See below for the structures of these two compounds. Note that Zn-DPA-(8), Zn-DPA-(12), Zn-DPA-(25), Zn-DPA-(26), and Zn-DPA-(42), and CPT-11 are prodrugs of the anti-cancer compound SN-38. Zn-DPA-(26), Zn-DPA-(42), and CPT-11 contained SN-38 at about 24%, 18%, and 58%, respectively.

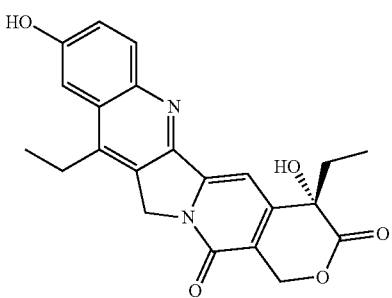 [SMILES: CCc1c2c(nc3ccc(O)cc13)-c1cc3c(c(=O)n1C2)COC(=O)[C@]3(O)CC]

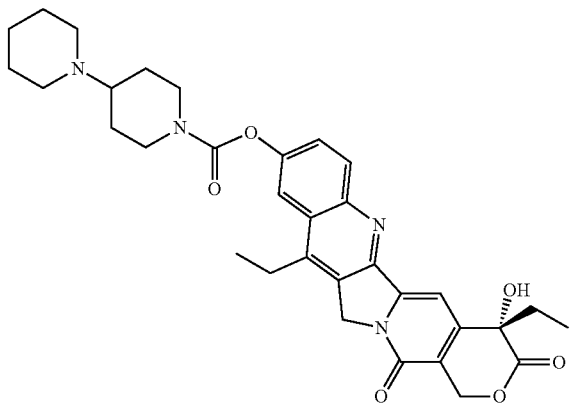 [SMILES: CCc1c2c(nc3ccc(OC(=O)N4CCC(N5CCCCC5)CC4)cc13)-c1cc3c(c(=O)n1C2)COC(=O)[C@]3(O)CC]

TABLE 2

IC$_{50}$ values of Zn-DPA conjugates, Zn-DPA-(8), Zn-DPA-(12), Zn-DPA-(25), Zn-DPA-(26), Zn-DPA-(42), and two anticancer compounds (SN-38 and CPT-11) against human cancer cells (Colo205, SCM-1, MiaPaca2) and human embryonic skin fibroblast Detroit 551.

| Conjugates or Compounds | Colo205 | SCM-1 | MiaPaca2 | Detroit 551 |
|---|---|---|---|---|
| Zn-DPA-(8) | 0.42 | 0.64 | — | 9.3 |
| Zn-DPA-(12) | 0.12 | 0.94 | — | 2.9 |
| Zn-DPA-(25) | 0.58 | 1 | — | 7.2 |
| Zn-DPA-(26) | 1.1 | 2.6 | 0.12 | >10 |
| Zn-DPA-(42) | 3.7 | — | 0.55 | >10 |
| SN-38 | 0.14 | 0.64 | 0.02 | 4 |
| CPT-11 | >10 | >10 | 3.6 | >10 |

*unit in (μM)

In Vivo Antitumor Assay

Two Zn-DPA conjugates, Zn-DPA-(26) and Zn-DPA-(42) were subjected to an in vivo antitumor assay against Colo205 or MiaPaca2 tumors growing in nude mice following the procedure described below.

More specifically, Colo205 or MiaPaca2 cells were cultured and maintained in a flask with a RPMI-1640 medium, which was supplemented with 10% FBS. The cells were harvested and innoculated ($1\times10^6$ cells) subcutaneously into the left flank of a adult male nude mouse. Tumor-bearing mice were grouped at the mean tumor volume of approximately 200 mm$^3$. Tumor dimensions were measured with a digital caliper, and the tumor volume in mm$^3$ was calculated by the formula: Volume=(length×width$^2$)/2.

The mice were housed in sterilized cages equipped with an air filter and sterile bedding materials at the Laboratory Animal Center of National Health Research Institutes. All mice were fed with sterilized water and chow at libitum under 12-hour light/12-hour dark cycle throughout the study.

Several dosages of Zn-DPA-(26) and Zn-DPA-(42), were used in this assay, i.e., 40 mg/kg, 20 mg/kg, and 10 mg/kg, $p<0.05$ vs. vehicle control by one-way ANOVA analysis and the Newman-Keuls multiple comparison test. Both Zn-DPA-(26) and Zn-DPA-(42) in the mixture of 10% DMSO/20% Cremophor EL/70% dextrose were intravenously administered in a regimen of once daily for five consecutive days when dosed at 20 mg/kg or 10 mg/kg, or of twice per week, for two weeks when dosed at 40 mg/kg; CPT-11 (40 mg/kg) was intravenously administered twice a week for two weeks; and SN-38 (10 mg/kg) in the mixture of 10% DMSO/20% Cremophor EL/10% Na$_2$CO$_3$/60% dextrose was intravenously administered at once daily for five consecutive days for two weeks.

Although the amounts of SN-38 contained in Zn-DPA-(26) and Zn-DPA-(42) were only 24% and 18%, respectively (as compared to 58% contained in CPT-11), these two Zn-DPA conjugates were found to unexpectedly show much greater antitumor activities than those of SN-38 and CPT-11 tested in the Colo205 tumor xenograft mouse model. More specifically, it was found that Zn-DPA-(26) unexpectedly showed much higher antitumor activities at dosages of 10 mg/kg and 40 mg/kg, compared to those of SN-38 at 10 mg/kg and CPT-11 at 40 mg/kg; and Zn-DPA-(42), also unexpectedly, showed antitumor activities in a dose-dependent manner and much higher antitumor activities at all three dosages, compared to those of SN-38 at 10 mg/kg and CPT-11 at 40 mg/kg.

Moreover, in the MiaPaca2 tumor xenograft mouse model, Zn-DPA-(42) unexpectedly showed antitumor activities in a dose-dependent manner and much higher antitumor activities at dosages of 40 mg/kg, 20 mg/kg, and 10 mg/kg, compared to those of SN-38 at 10 mg/kg and CPT-11 at 40 mg/kg.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention also can be made, screened for their efficacy in treating a condition that relates to cells containing inside-out phosphatidylserine. Thus, other embodiments are also within the claims.

What is claimed is:

1. A compound of formula (I):

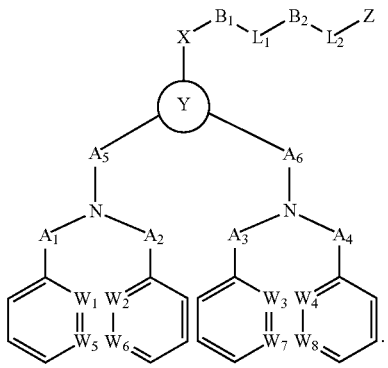

in which
each of $A_1$, $A_2$, $A_3$, $A_4$, $A_5$, and $A_6$, independently, is a $C_1$-$C_6$ bivalent aliphatic radical;
$B_1$ is a $C_1$-$C_6$ bivalent aliphatic radical, a $C_1$-$C_6$ bivalent heteroaliphatic radical, a bivalent aryl radical, or a bivalent heteroaryl radical;
$B_2$ is a bond, a $C_1$-$C_6$ bivalent aliphatic radical, a $C_1$-$C_6$ bivalent heteroaliphatic radical, a bivalent aryl radical, a bivalent heteroaryl radical, $D_1$-$NR_1$—C(O)-$D_2$, $D_1$-C(O)$NR_1$-$D_2$-$NR_1'$—C(O)-$D_3$, $D_1$-$D_2$-C(O)—$NR_1$—C(O)-$D_3$, or $D_1$-$D_2$-$D_3$, each of $D_1$, $D_2$, $D_3$, independently, being a $C_1$-$C_6$ bivalent aliphatic radical, a $C_1$-$C_6$ bivalent heteroaliphatic radical, a bivalent aryl radical, a bivalent heteroaryl radical, a $C_1$-$C_{10}$ bivalent aralkyl radical, or a $C_1$-$C_{10}$ bivalent heteroaralkyl radical, and each of $R_1$ and $R_1'$, independently, being H, a $C_1$-$C_6$ bivalent heteroaliphatic radical, a bivalent aryl radical, a bivalent heteroaryl radical, or a $C_1$-$C_{10}$ bivalent aralkyl radical;
each of $L_1$ and $L_2$, independently, is a bond, $NR_2$, $NR_2C(O)$, $NR_2C(S)$, $NR_2CR_3R_4$, $NR_2SO_2$, $NR_2C(O)NR_3$, or $NR_2C(S)NR_3$, each of $R_2$, $R_3$, and $R_4$, independently, being H, a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, a $C_1$-$C_{14}$ monovalent heteroaralkyl radical, C(s)R', or C(O)R', in which R' is a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical, provided that at least one of $L_1$ and $L_2$ is not a bond;
each of $W_1$, $W_2$, $W_3$, $W_4$, $W_5$, $W_6$, $W_7$, and $W_8$, independently, is N or $CR_5$, $R_5$ being H, halo, cyano, amino, hydroxyl, nitro, sulfhydryl, a $C_1$-$C_6$ aliphatic radical, a $C_1$-$C_6$ heteroaliphatic radical, or a haloaliphatic radical;
X is a bond, O, S, or $NR_6$, $R_6$ being H, a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical;
Y is a aryl ring or a heteroaryl ring; and
Z is an anticancer therapeutic moiety,
wherein each of the aliphatic radical, the heteroaliphatic radical, the aralkyl radical, and the heteroaralkyl radical is unsubstituted or substituted with halo, cyano, amino, hydroxyl, nitro, sulfhydryl, $C_1$-$C_6$ alkoxy, $C_1$-$C_6$ alkylamino, $C_1$-$C_{12}$ dialkylamino, and $C_1$-$C_6$ haloalkyl; and each of the aryl radical and the heteroaryl radical is unsubstituted or substituted with halo, cyano, amino, hydroxyl, nitro, sulfhydryl, a $C_1$-$C_6$ aliphatic radical, a $C_1$-$C_6$ heteroaliphatic radical, or a haloaliphatic radical.

2. The compound of claim 1, wherein Y is

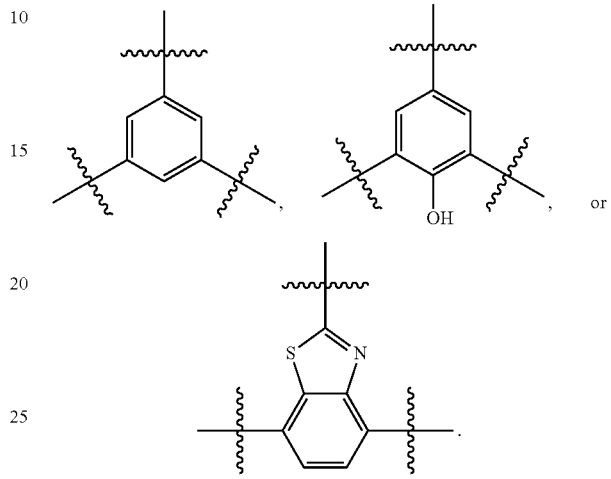

3. The compound of claim 1, wherein each of $W_1$, $W_2$, $W_3$, and $W_4$ is N, and each of $W_5$, $W_6$, $W_7$, and $W_8$ is CH.

4. The compound of claim 1, wherein each of $W_1$, $W_2$, $W_3$, and $W_8$ is N, and each of $W_4$, $W_5$, $W_6$, and $W_7$ is CH.

5. The compound of claim 1, wherein each of $A_1$, $A_2$, $A_3$, $A_5$, $A_5$, and $A_6$ is methylene.

6. The compound of claim 1, wherein $B_1$ is ethylene, propylene, butylene, or hexylene.

7. The compound of claim 1, wherein X is O or NH.

8. The compound of claim 1, wherein $L_2$ is C(O).

9. The compound of claim 1, wherein $L_1$ is a bond, NH, $NHCH_2$, NHC(O), $NHSO_2$, NHC(O)NH,

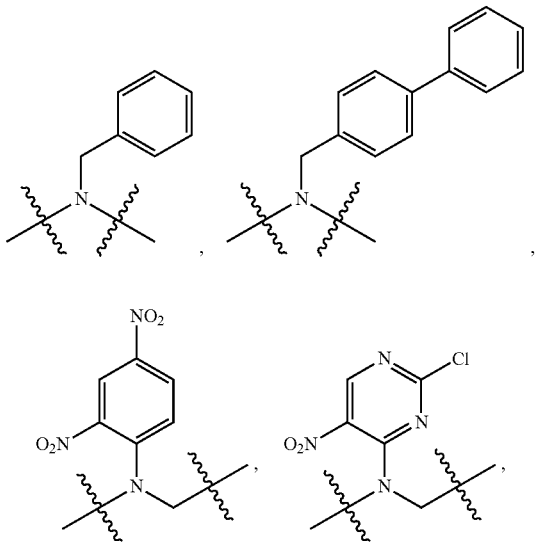

-continued
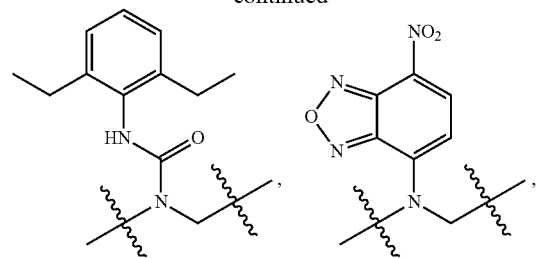
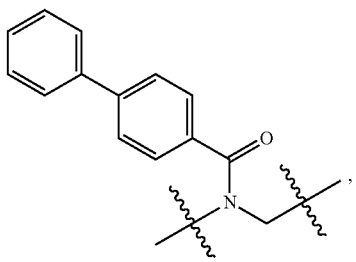
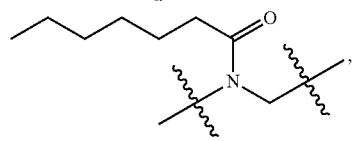
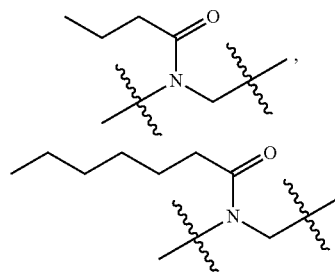
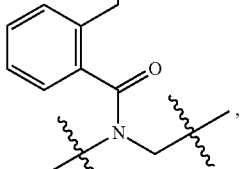
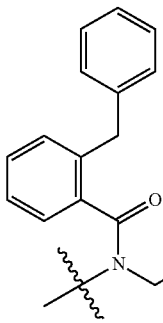
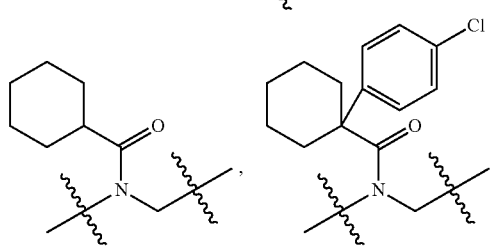
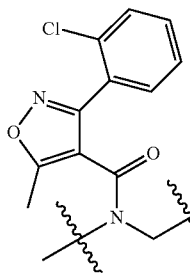
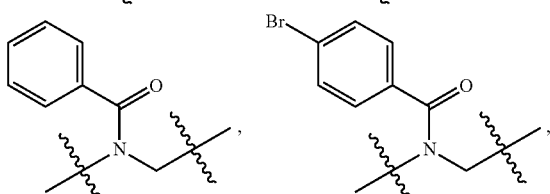
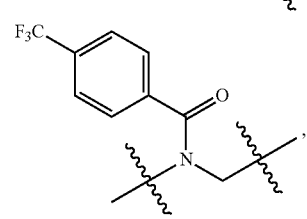
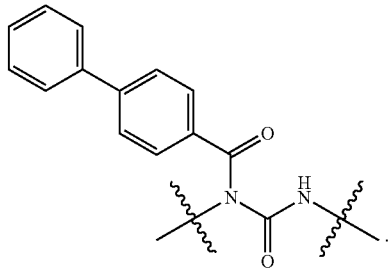
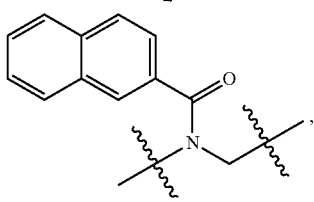
10. The compound of claim 1, wherein $B_2$ is a bond, ethylene, phenylene,
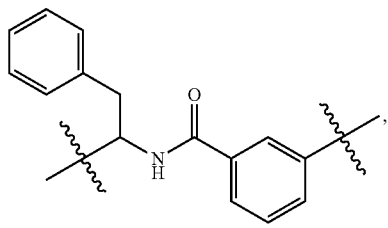
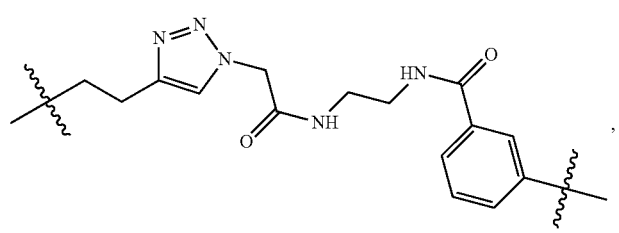

-continued
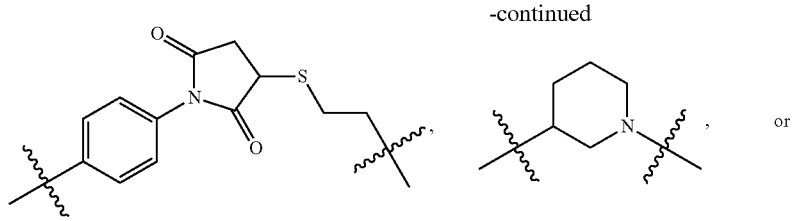
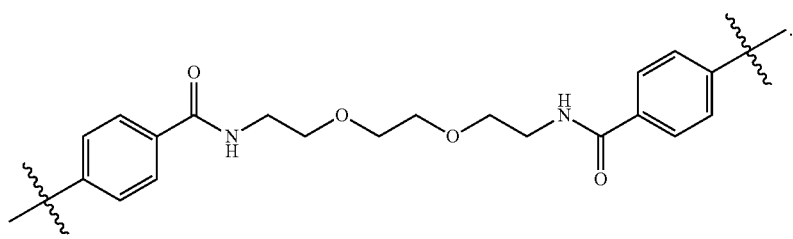
11. The compound of claim 1, wherein Z is
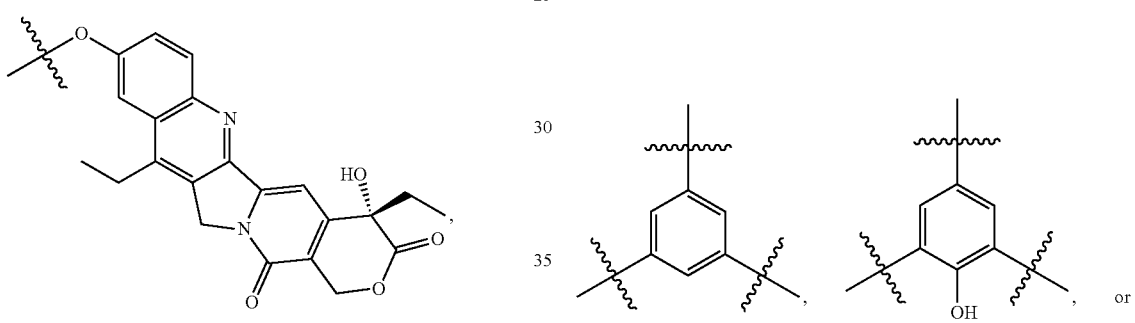
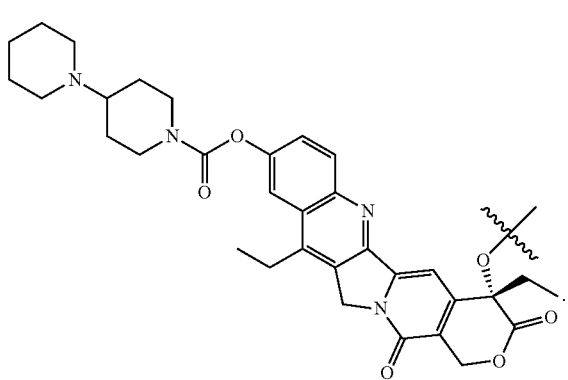
12. The compound of claim 11, wherein Y is
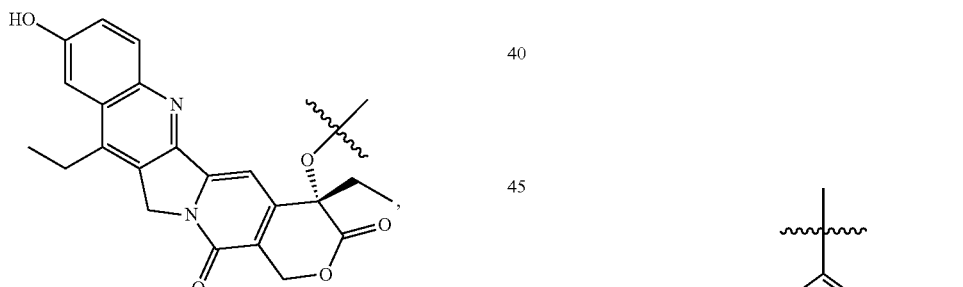
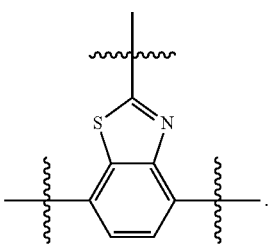
13. The compound of claim 11, wherein each of $A_1, A_2, A_3$, $A_5$, and $A_6$ is methylene.
14. The compound of claim 11, wherein X is O or NH.
15. The compound of claim 12, wherein each of $A_1, A_2, A_3$, $A_5, A_5$, and $A_6$ is methylene; X is O or NH; and $L_2$ is C(O).
16. The compound of claim 1, wherein the compound is one of the following compounds:

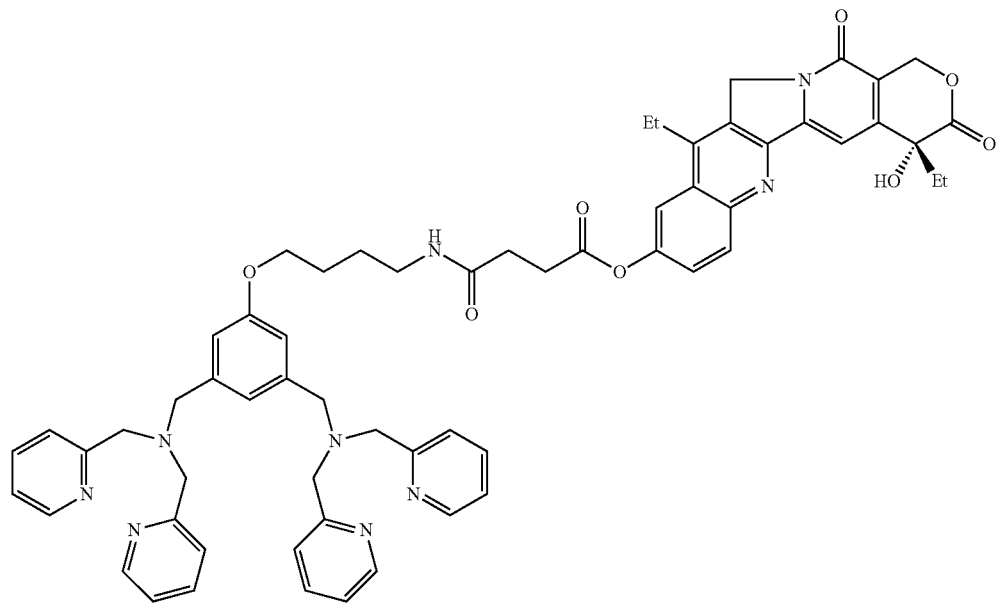
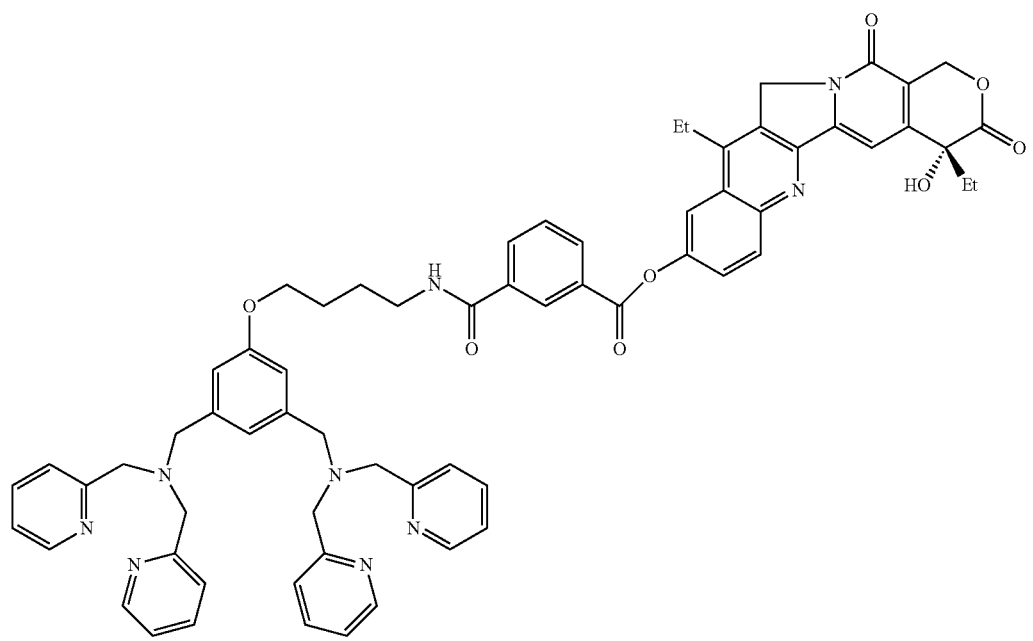

-continued
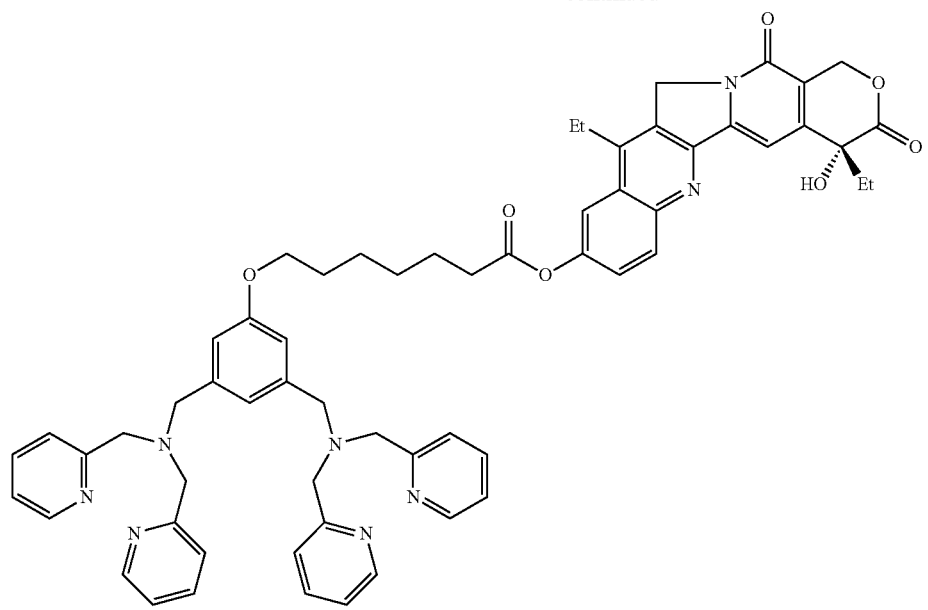
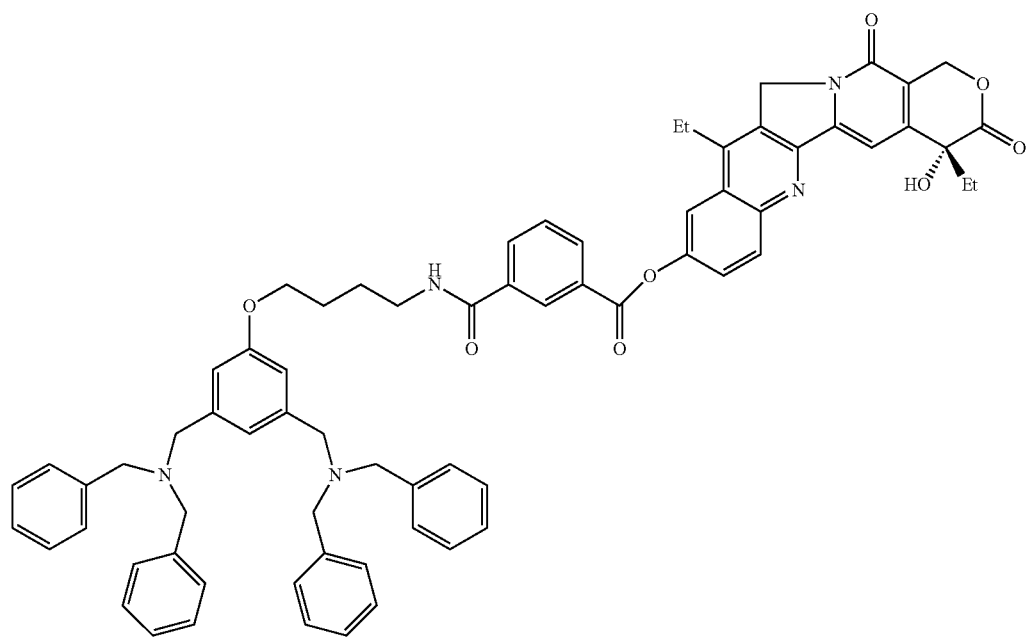

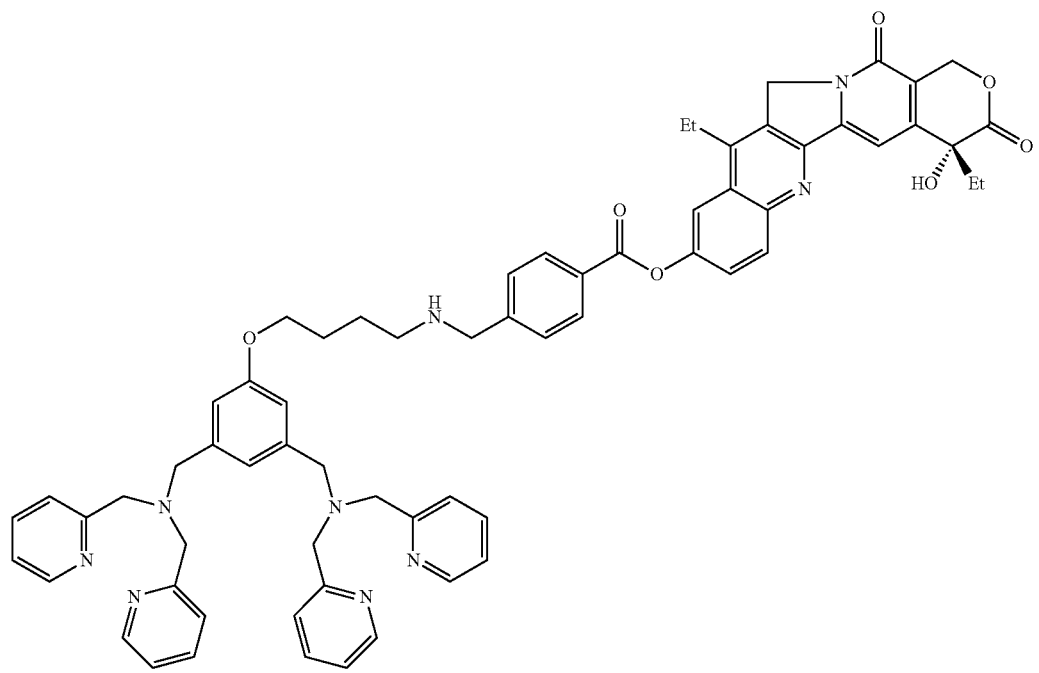
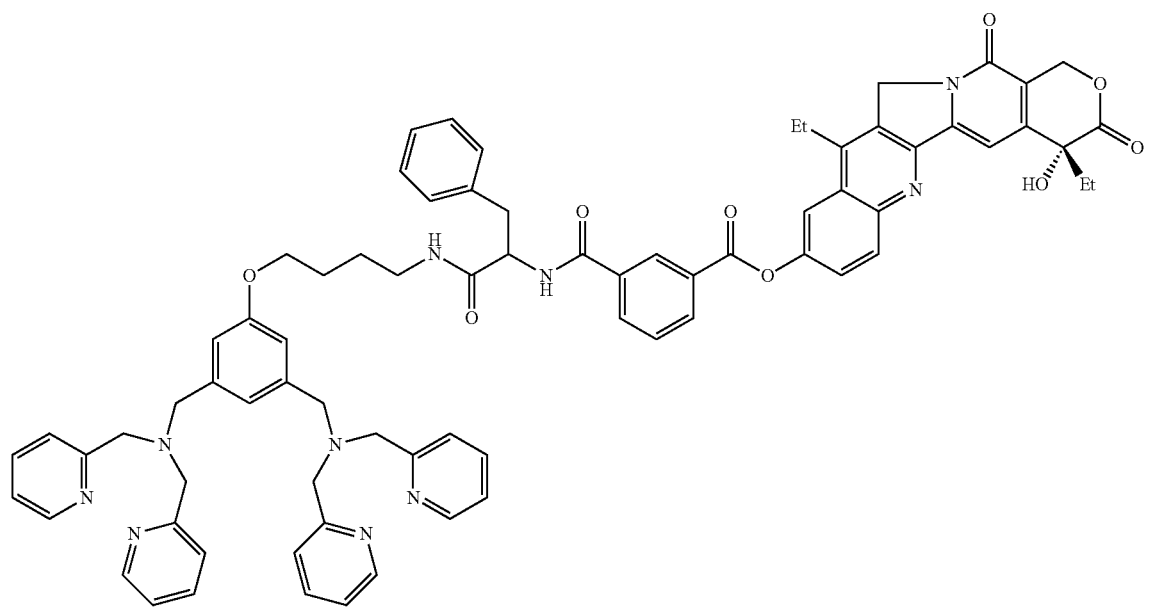

-continued
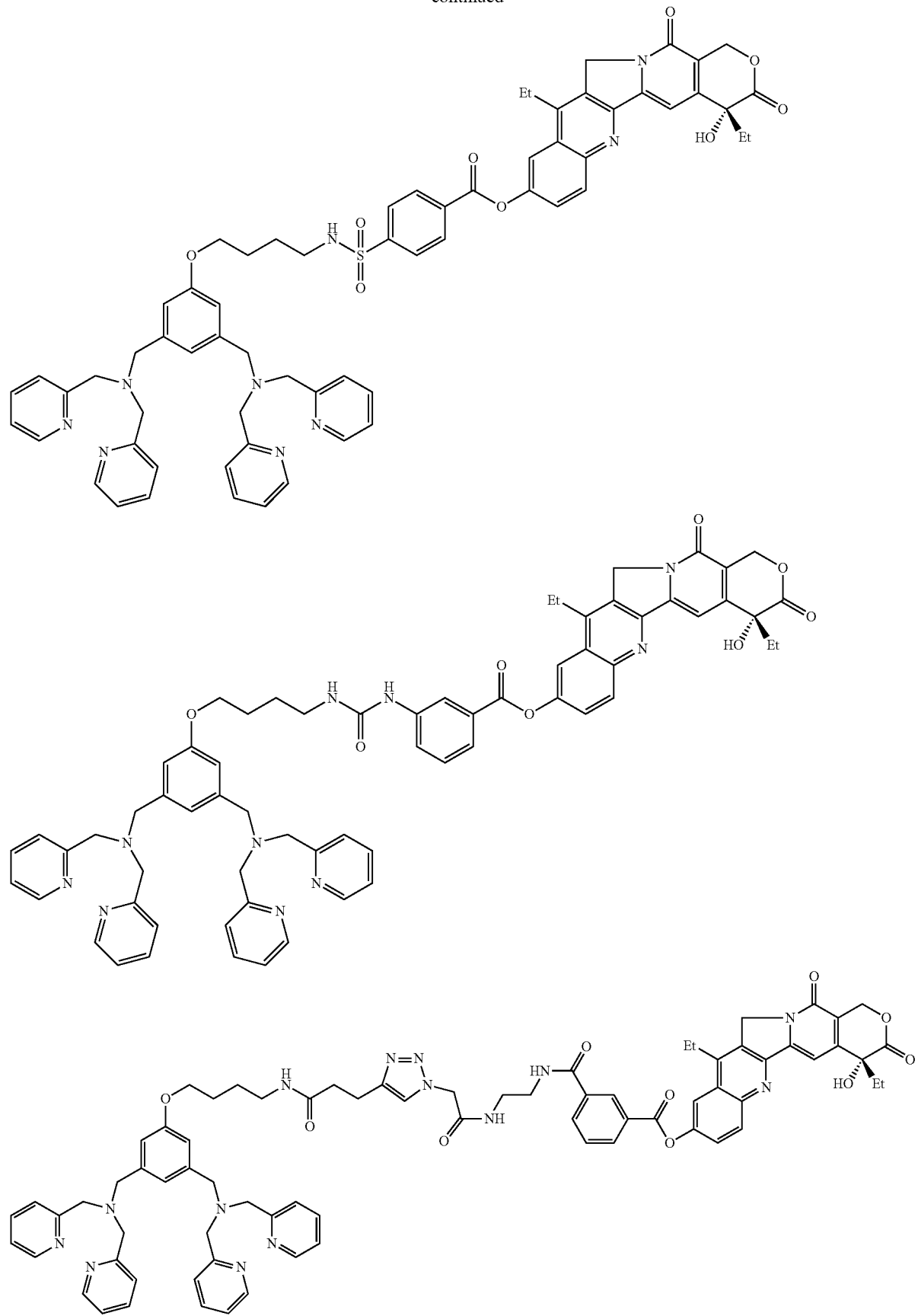

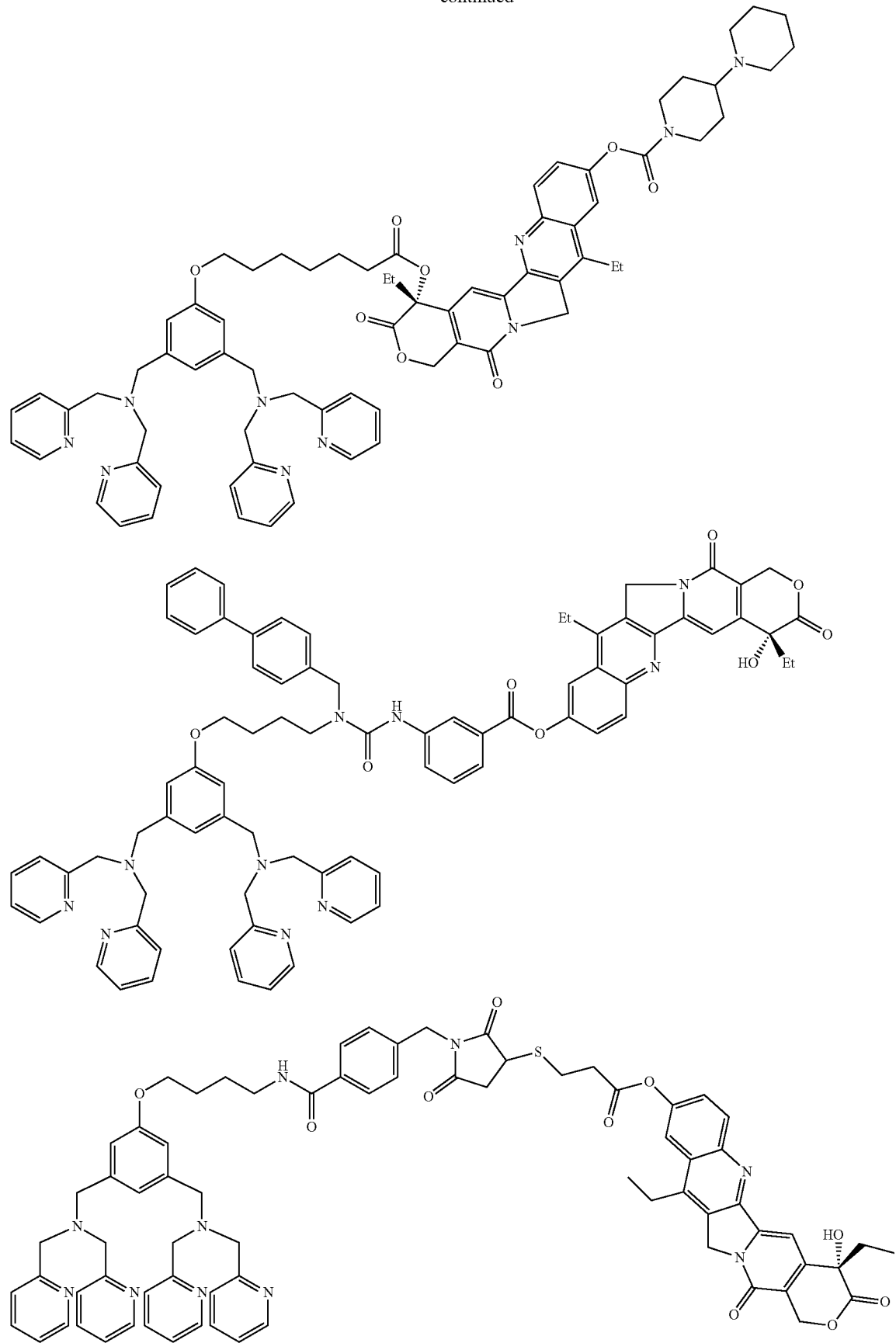

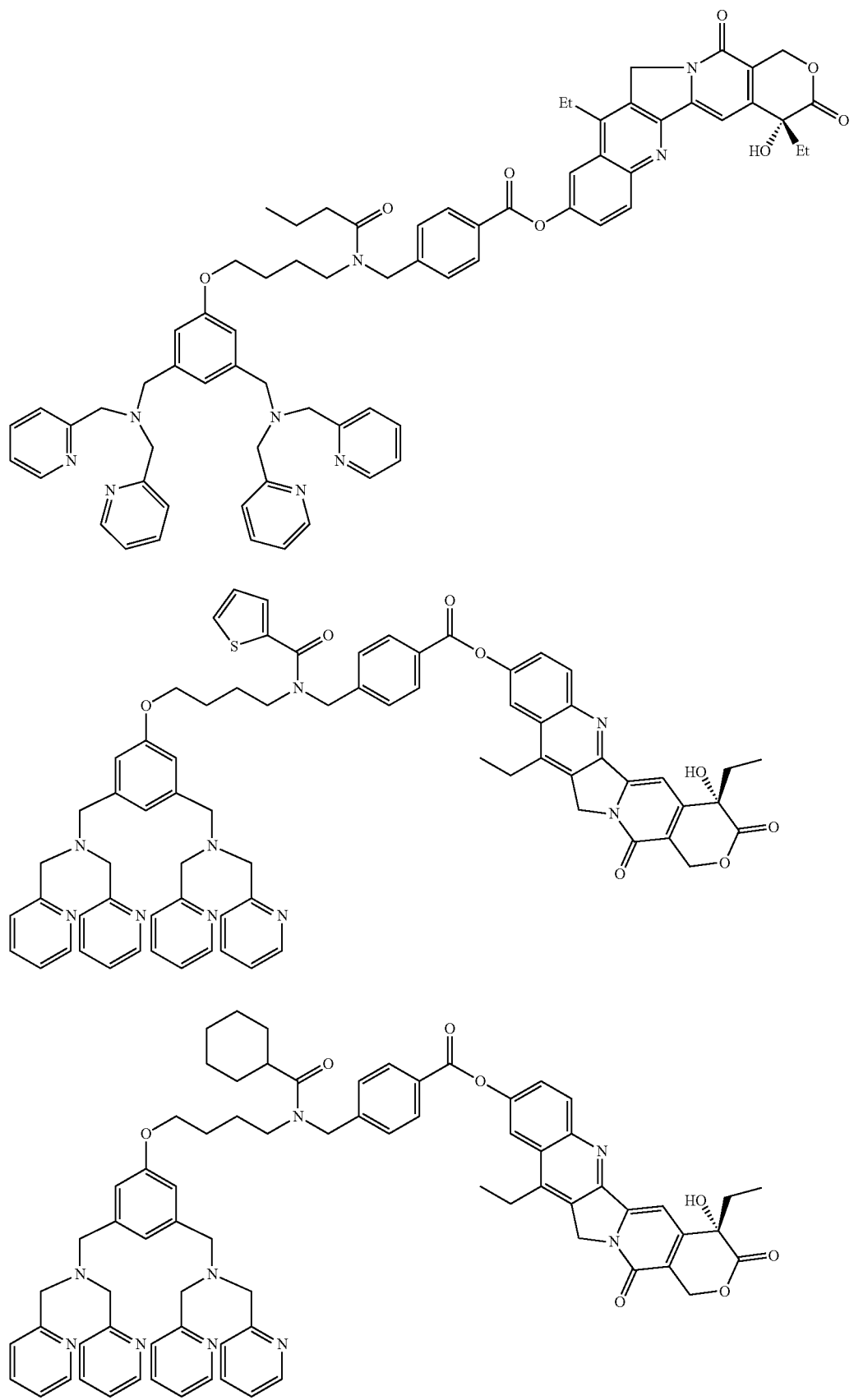

-continued
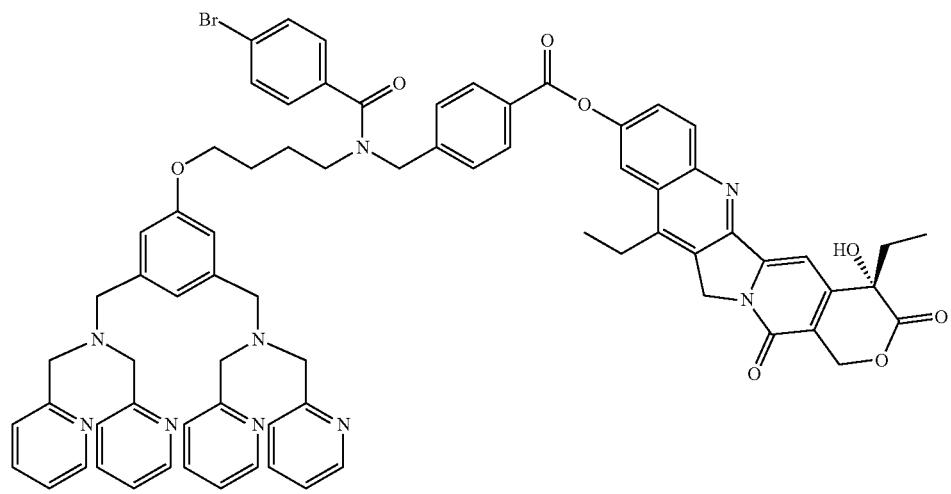
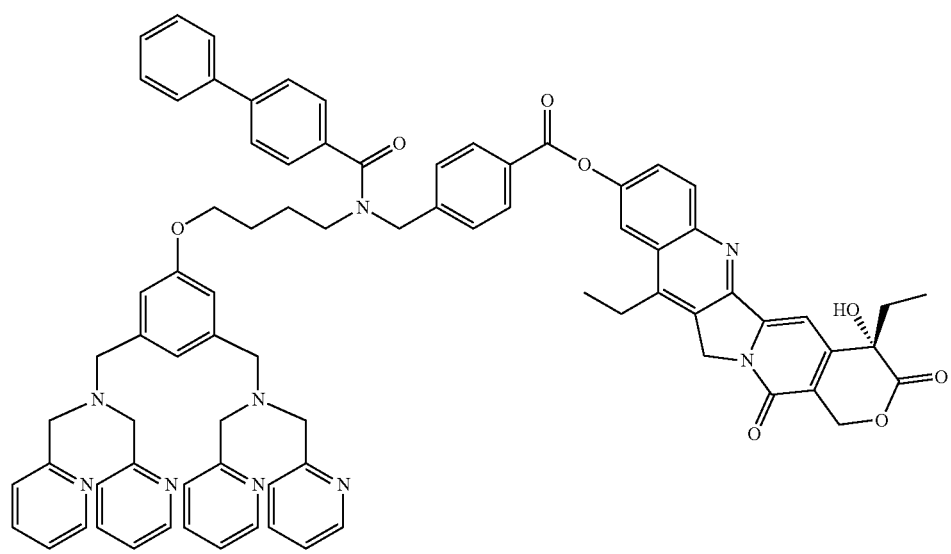
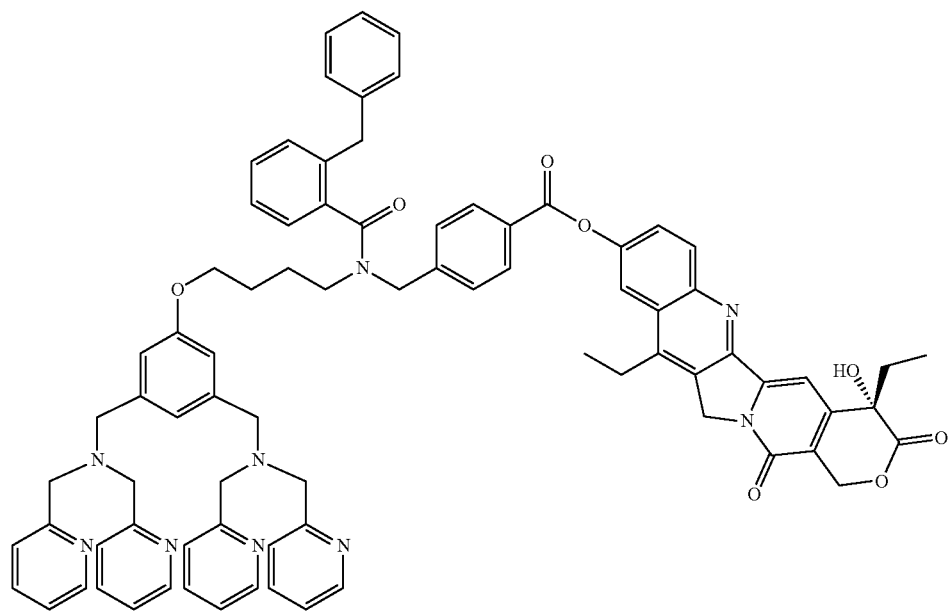

-continued
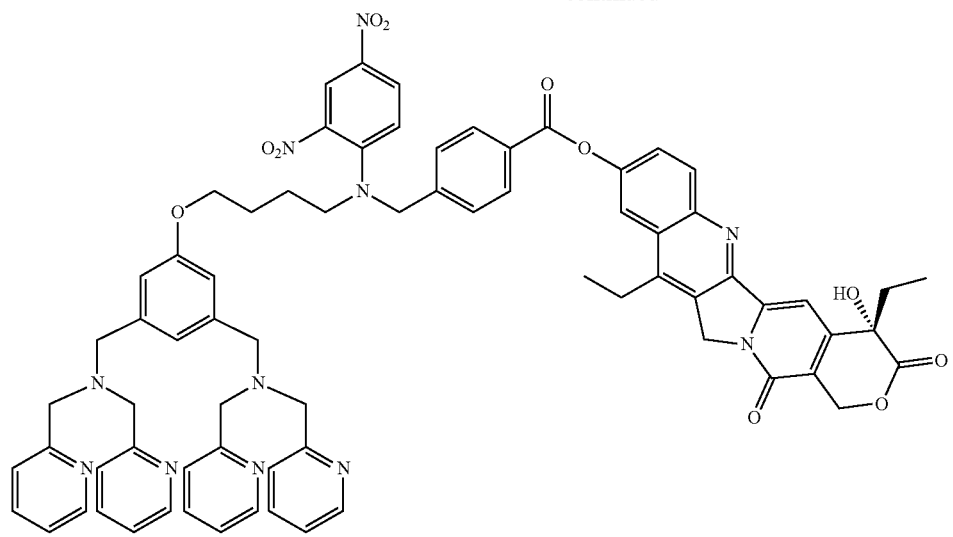
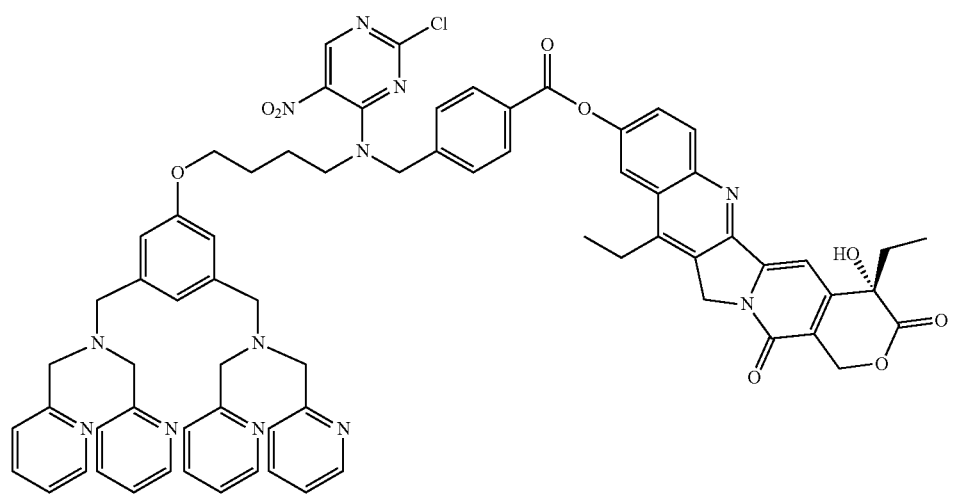
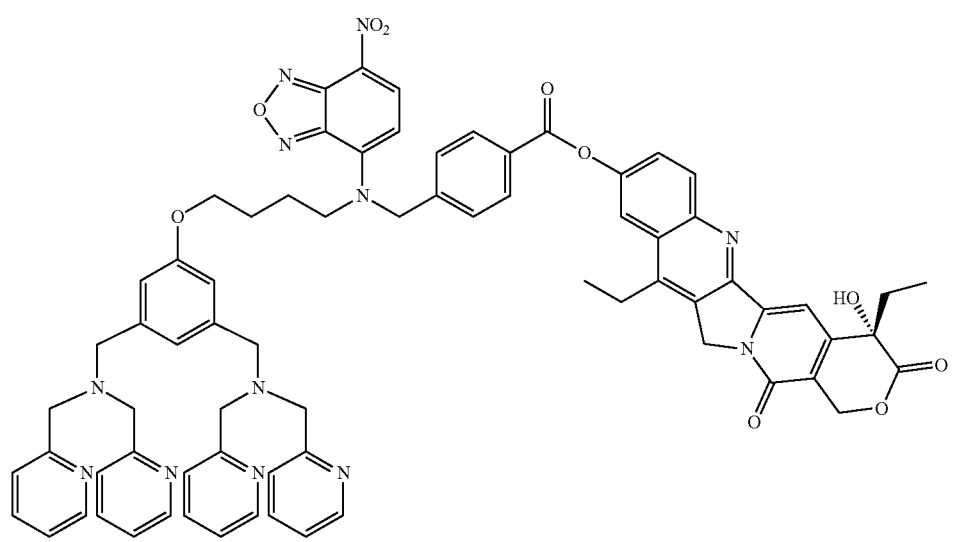

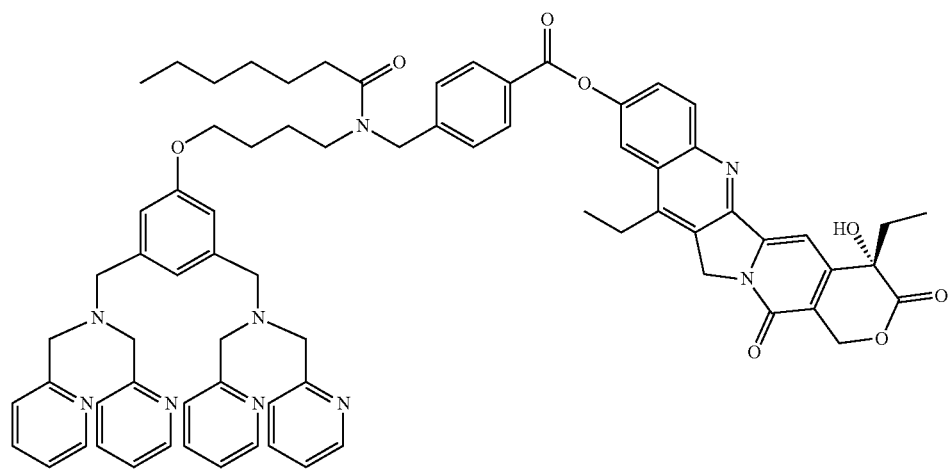
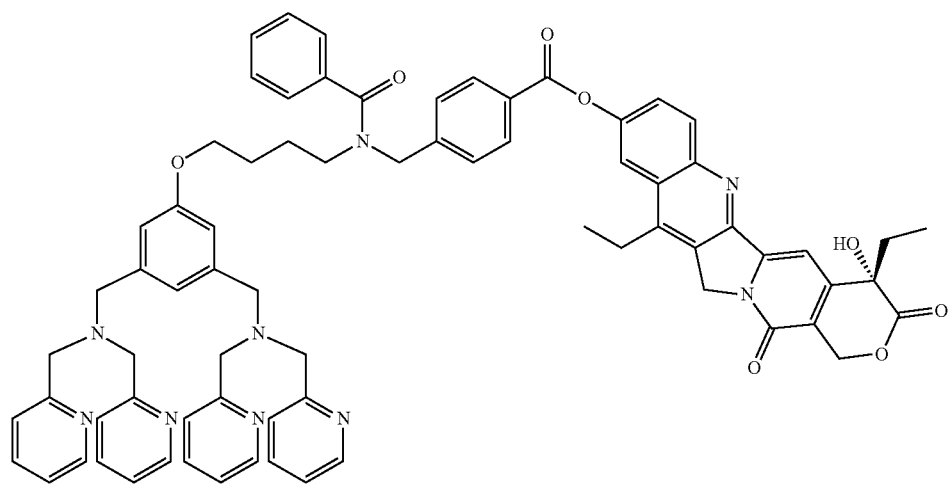
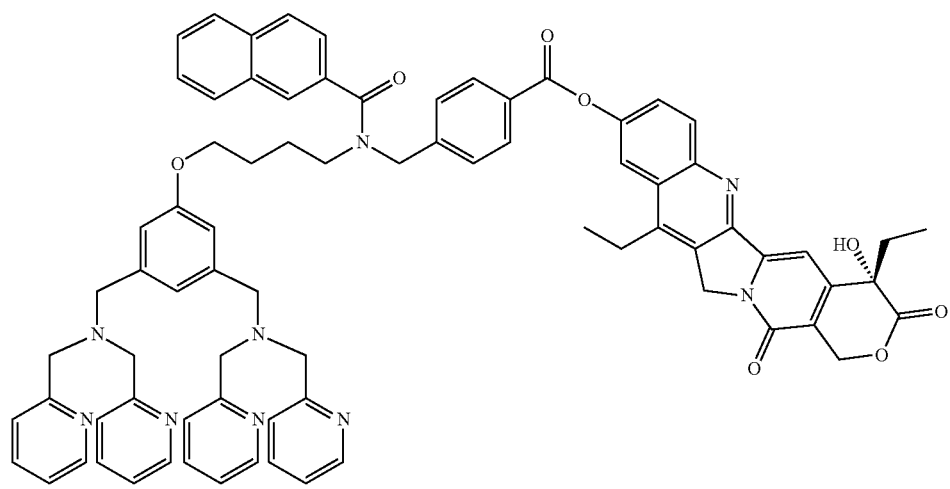

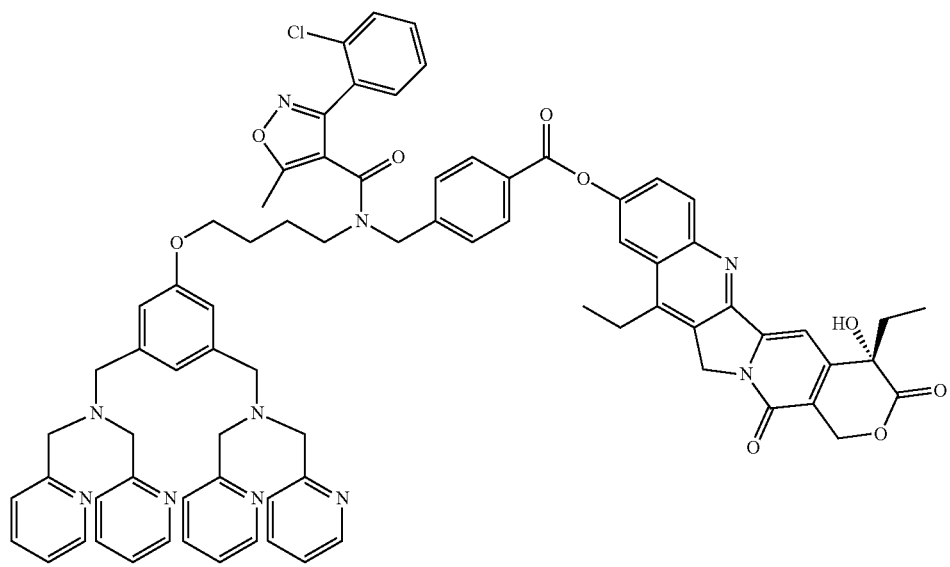
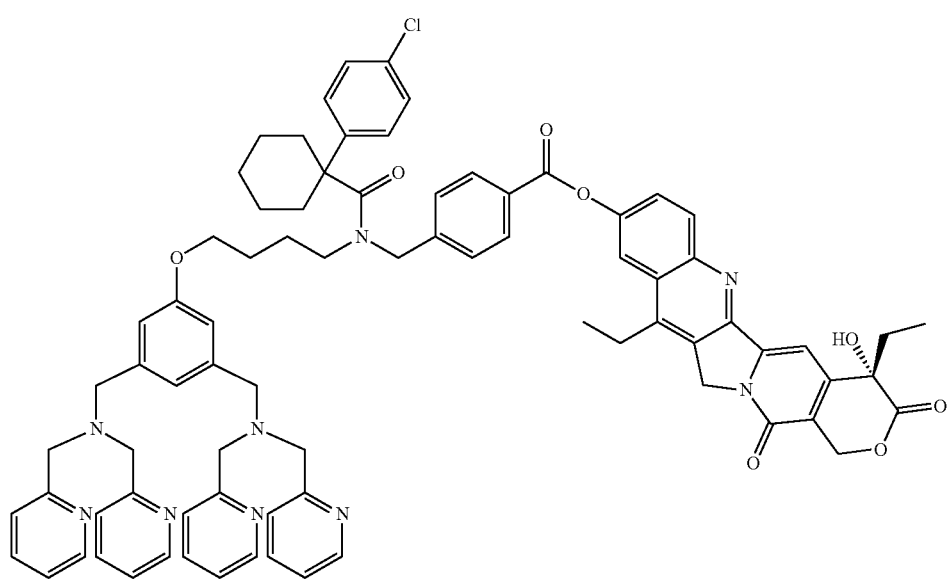
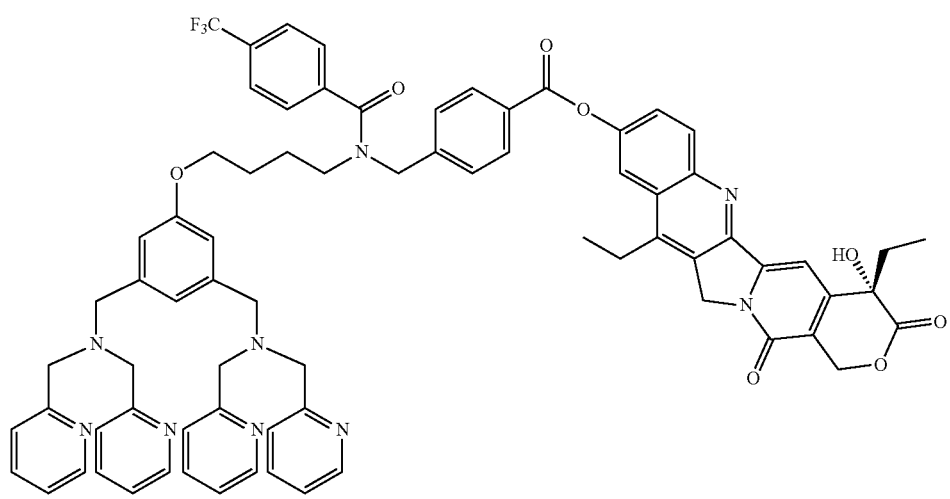

-continued
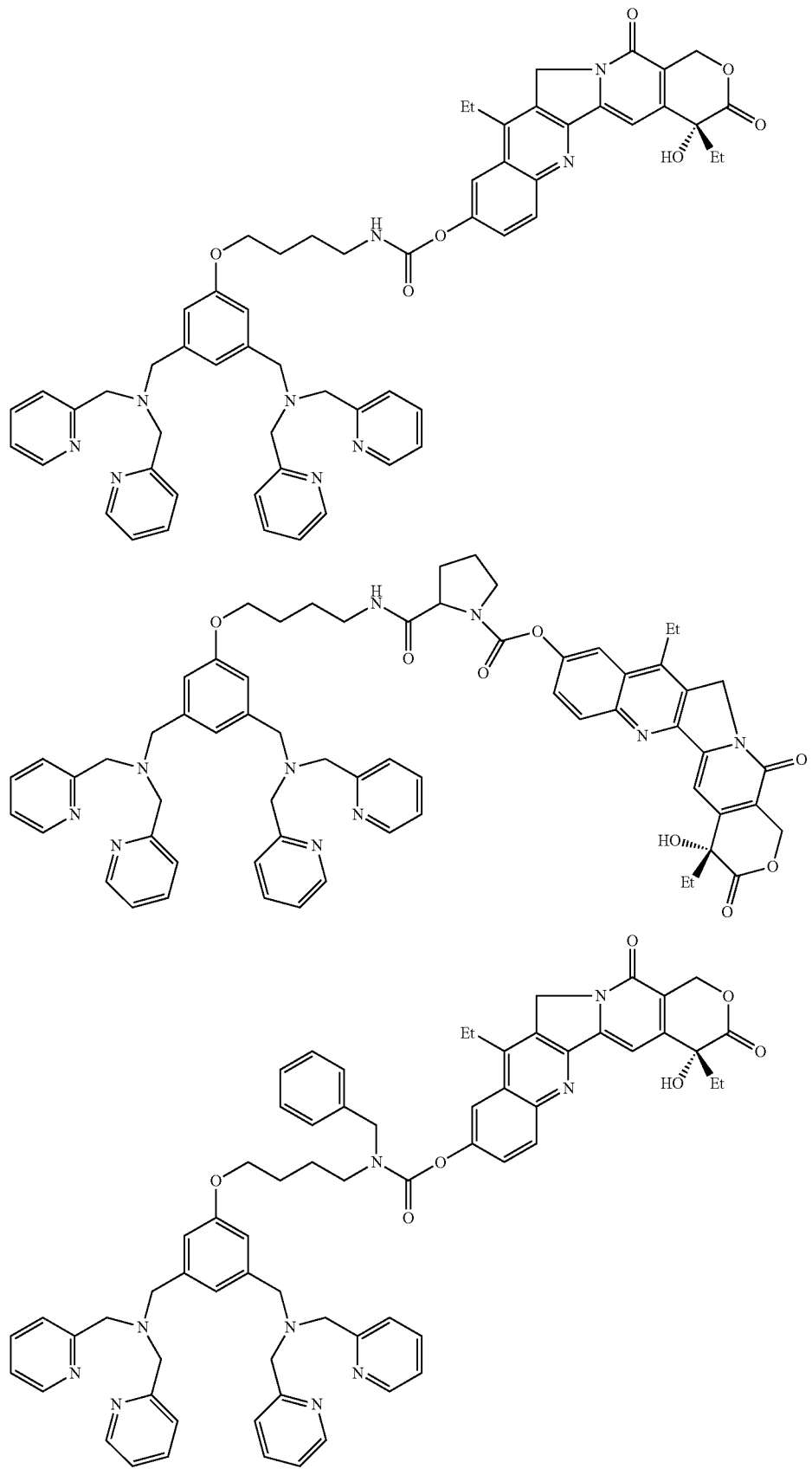

-continued
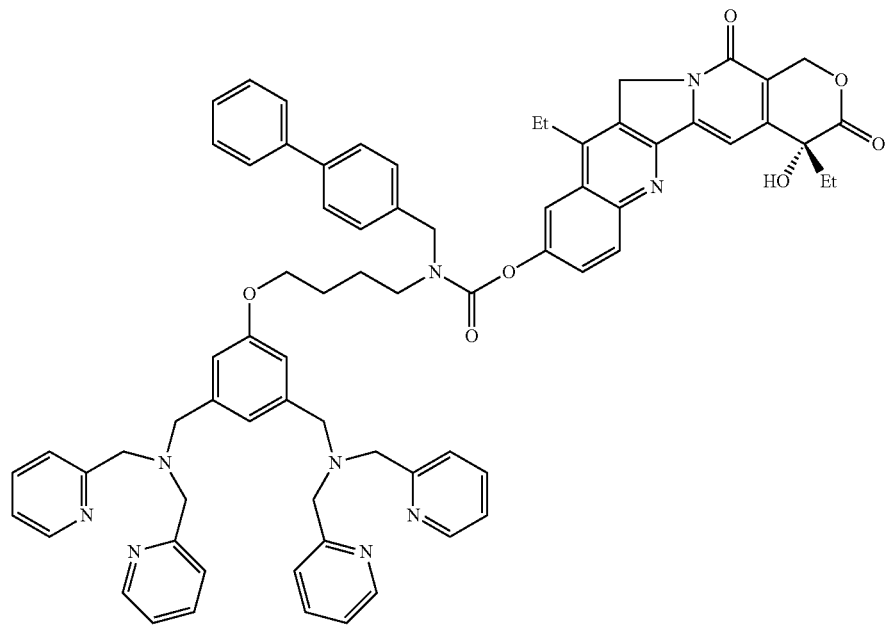
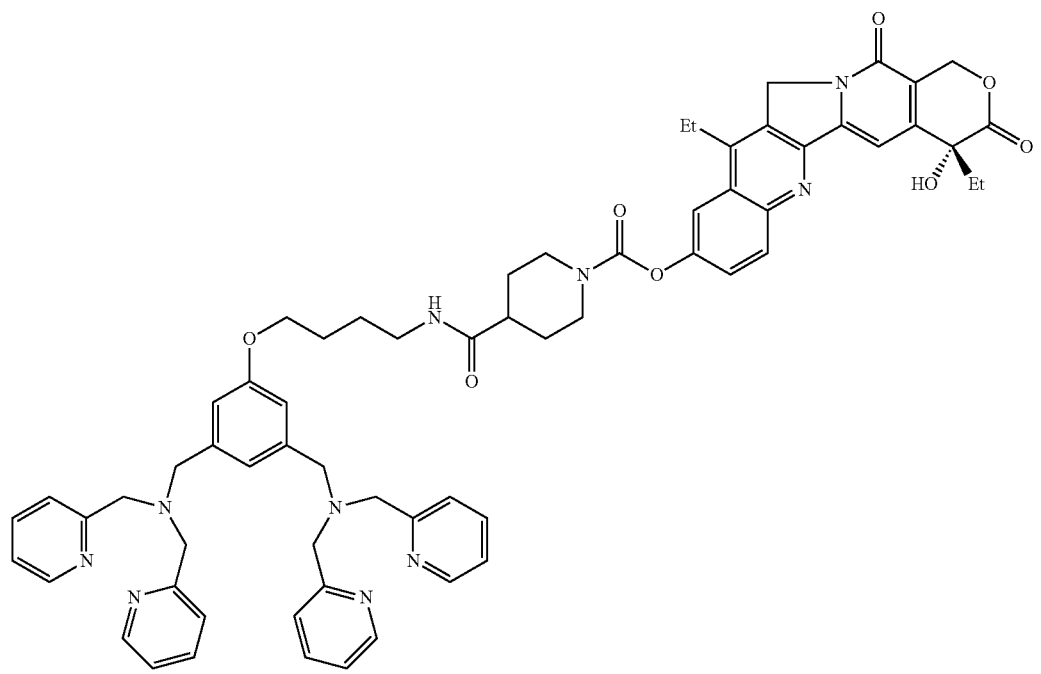

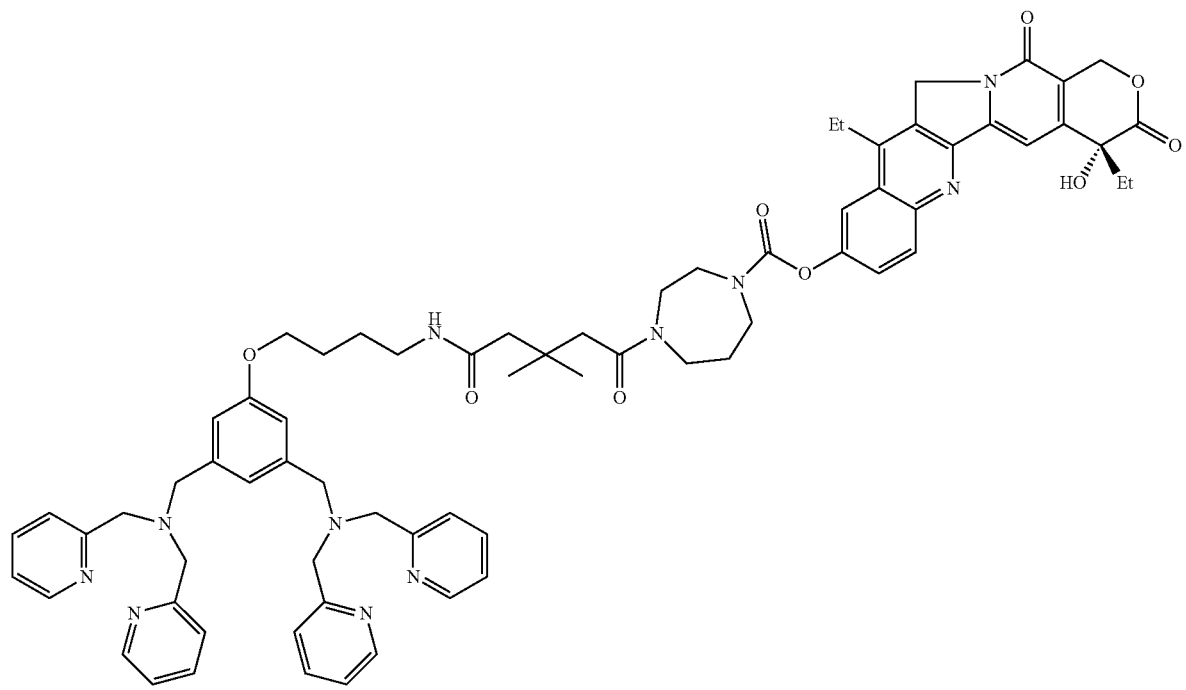
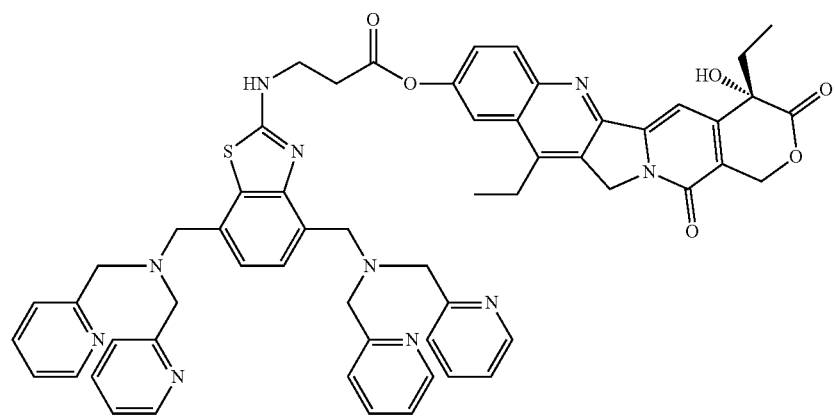
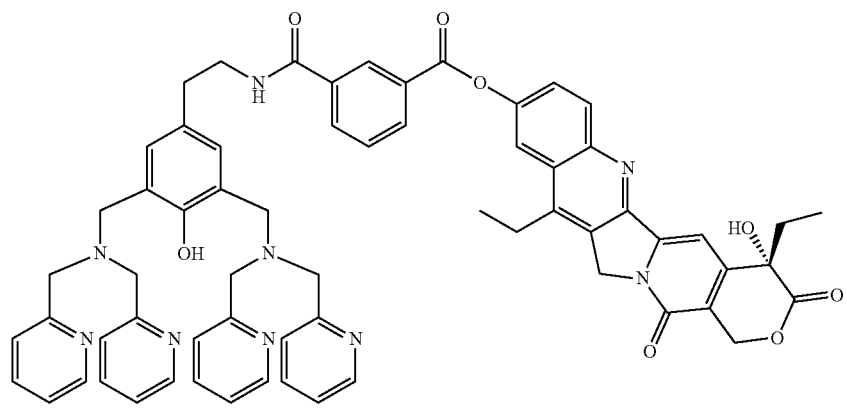

117 118
-continued
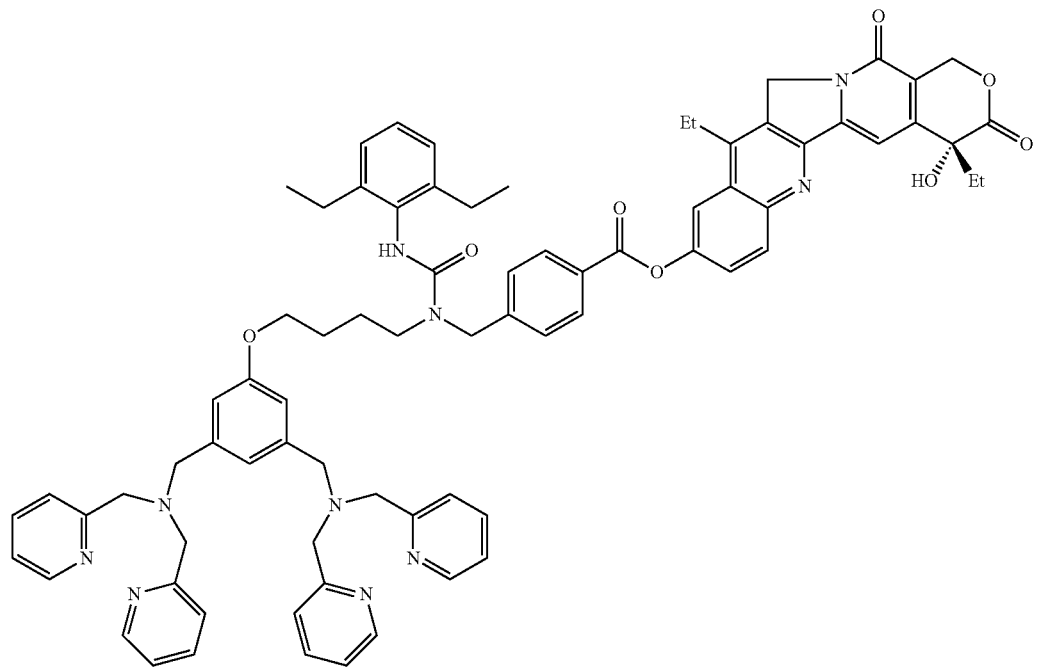
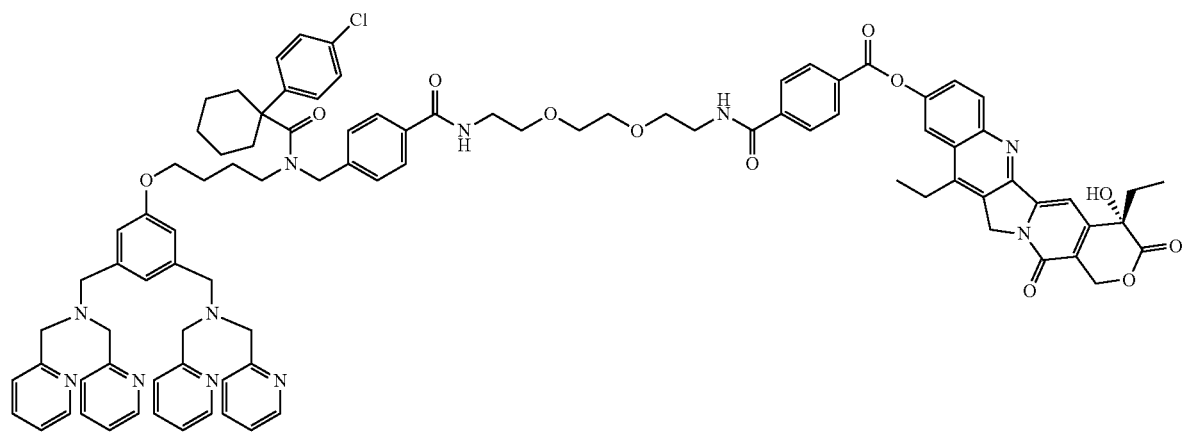
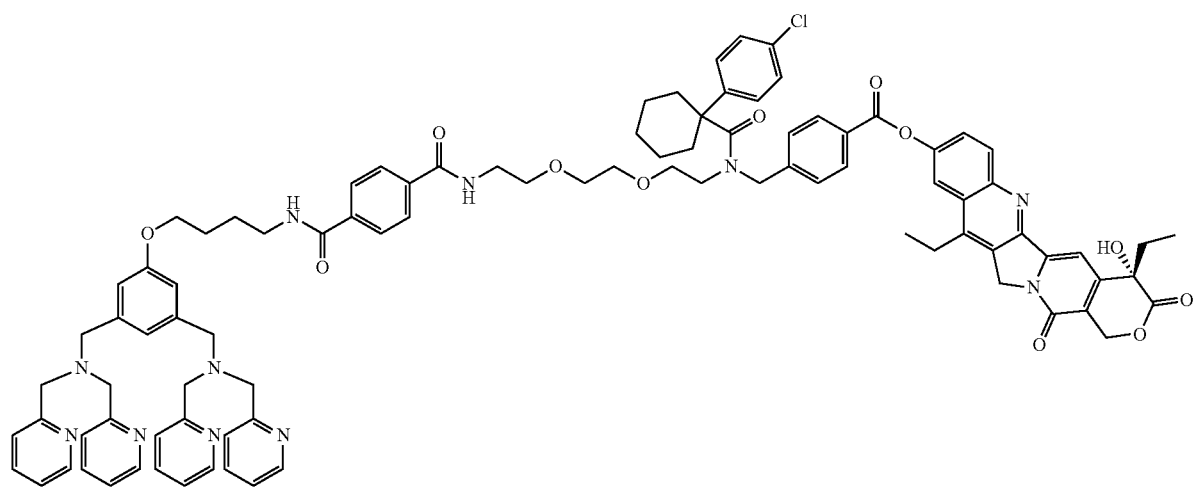

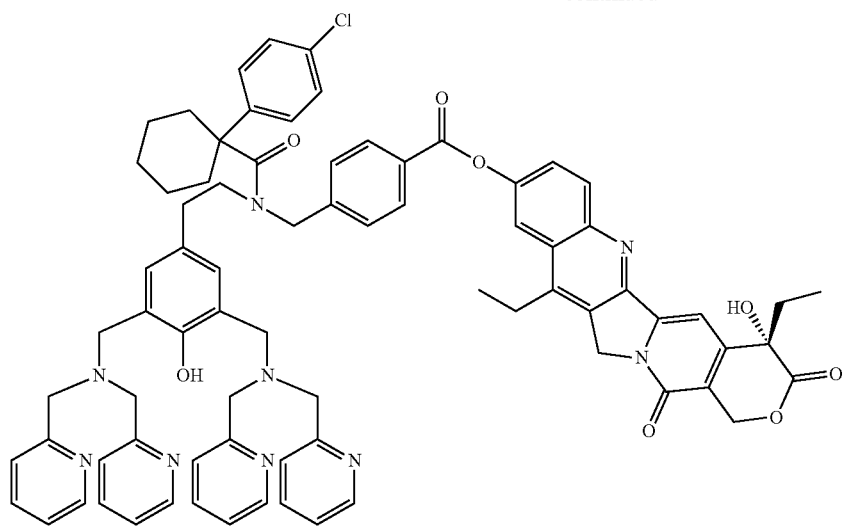
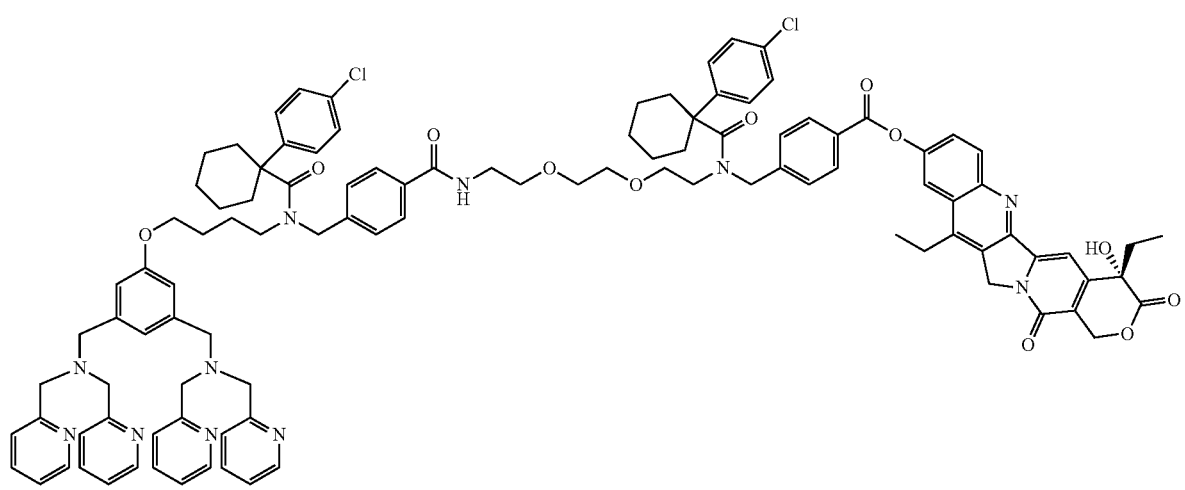 [SMILES: CCc1c2c(nc3ccc(OC(=O)c4ccc(CN(CCOCCOCCNC(=O)c5ccc(CN(CCCCOc6cc(CN(Cc7ccccn7)Cc7ccccn7)cc(CN(Cc7ccccn7)Cc7ccccn7)c6)C(=O)C6(c7ccc(Cl)cc7)CCCCC6)cc5)C(=O)C5(c6ccc(Cl)cc6)CCCCC5)cc4)cc13)-c1cc3c(c(=O)n1C2)COC(=O)[C@]3(O)CC]
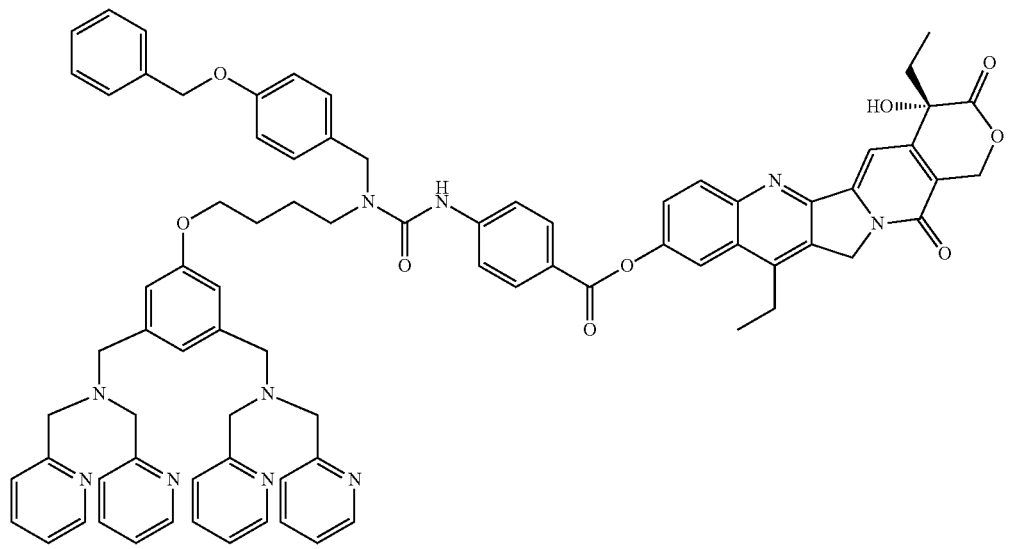

121 122
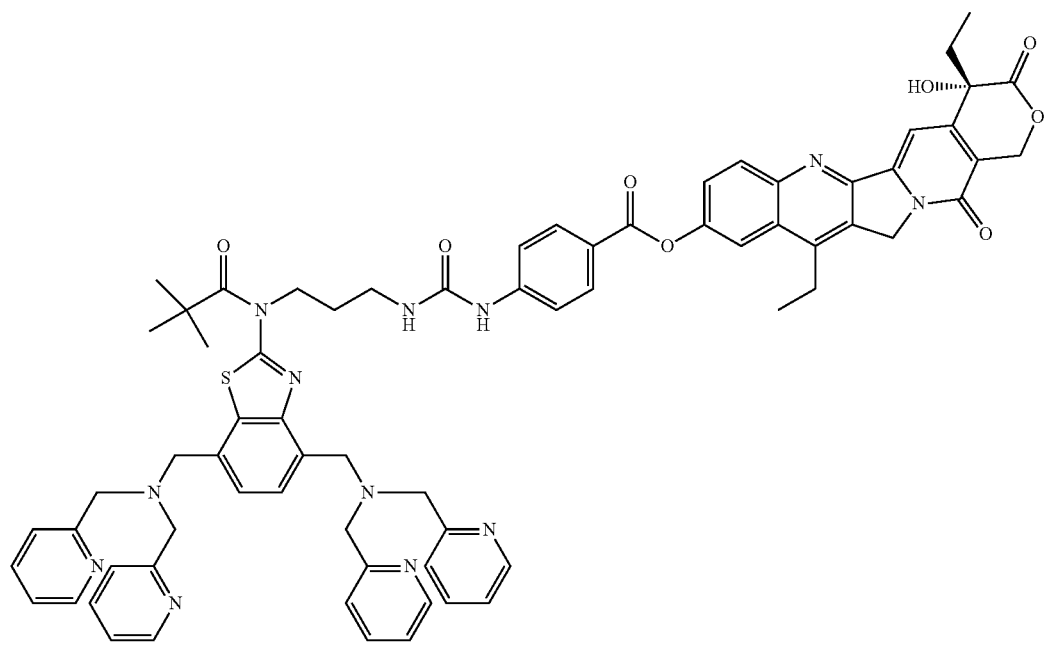
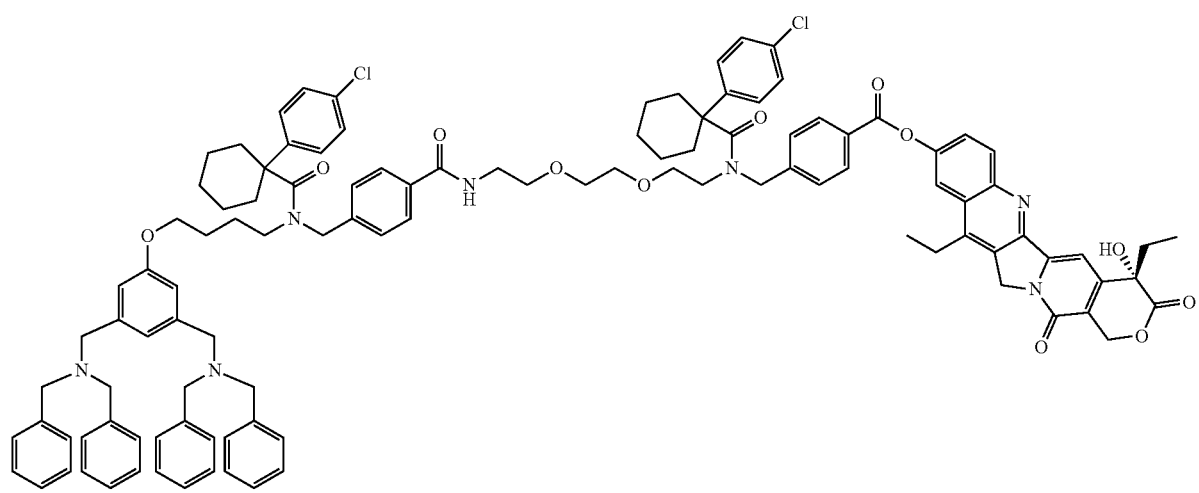

123
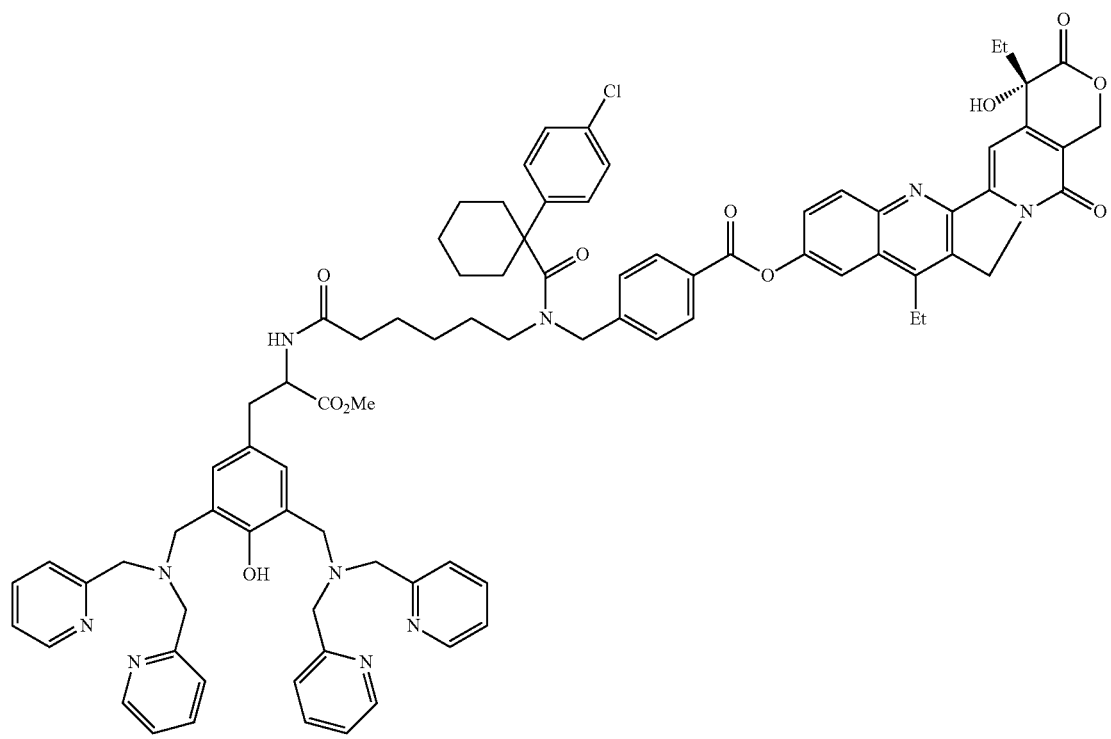
124
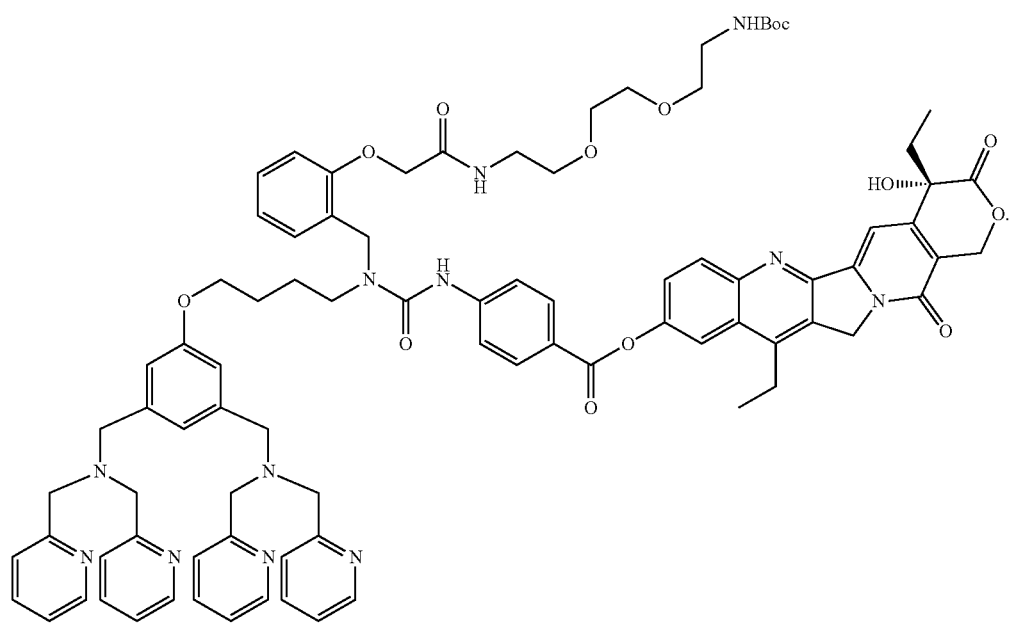

17. The compound of claim 16, wherein the compound is one of the following compounds:
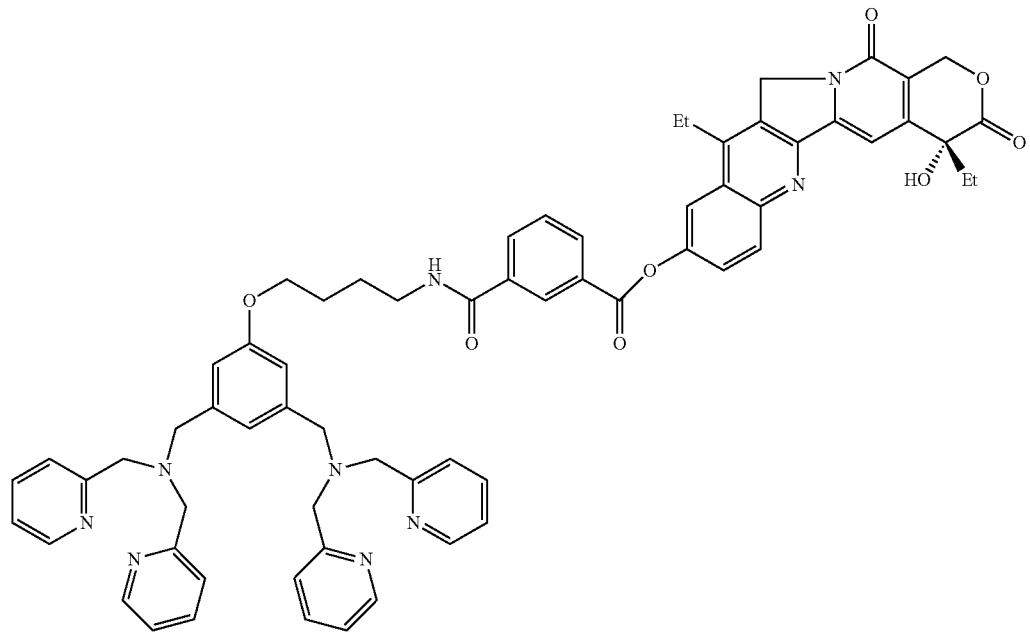
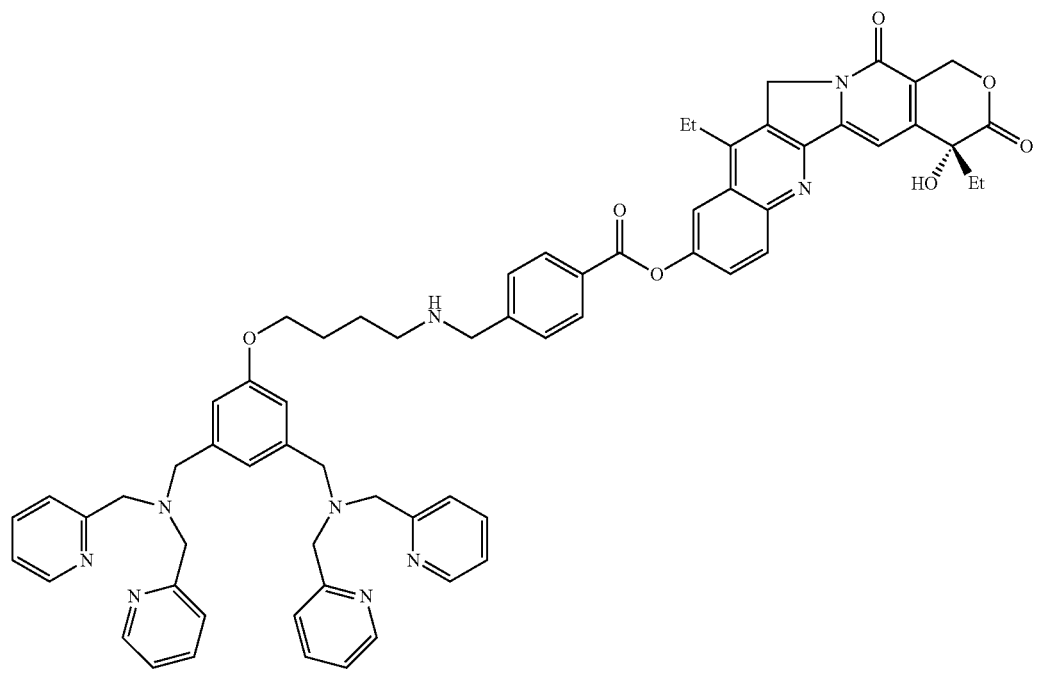

127 128
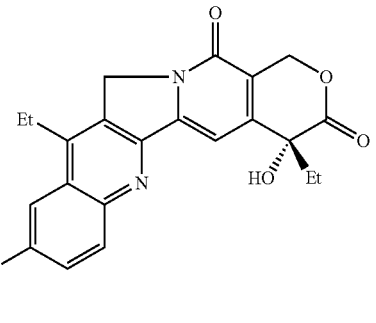
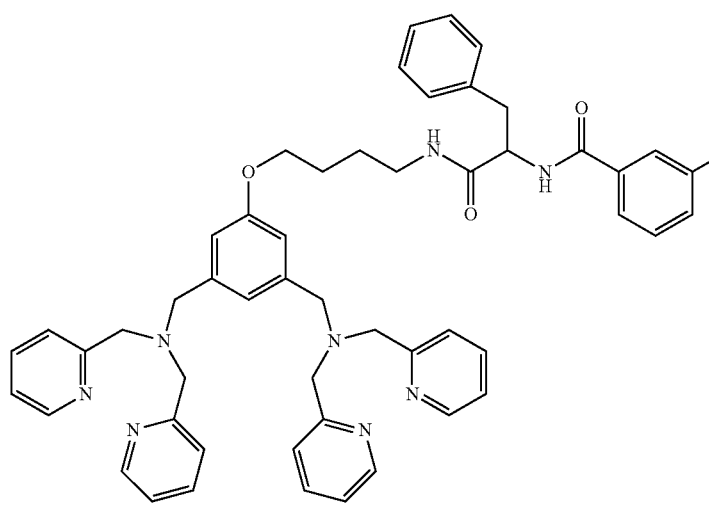
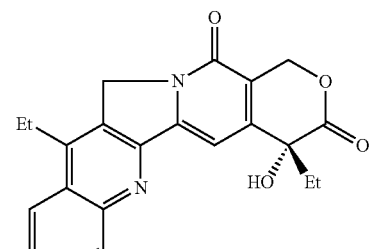
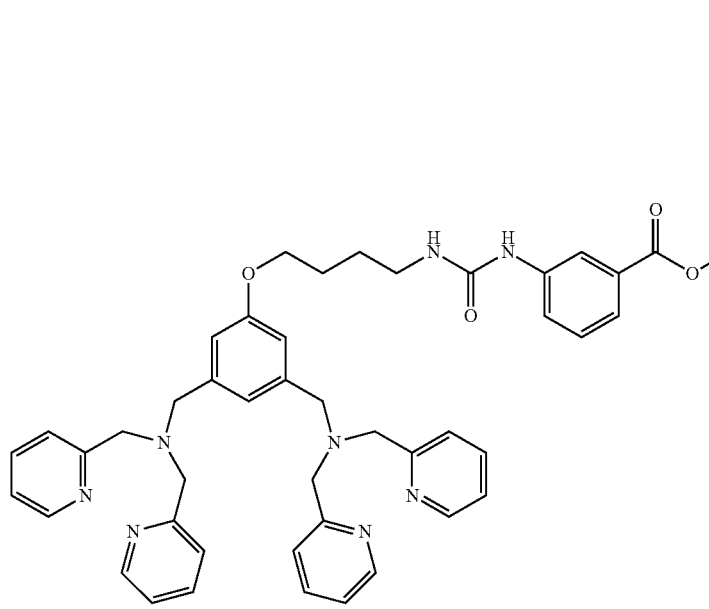
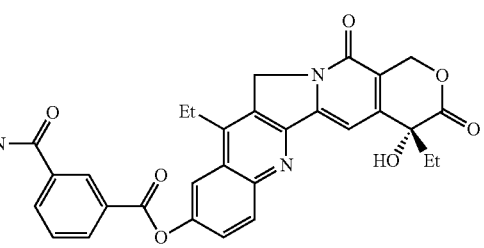
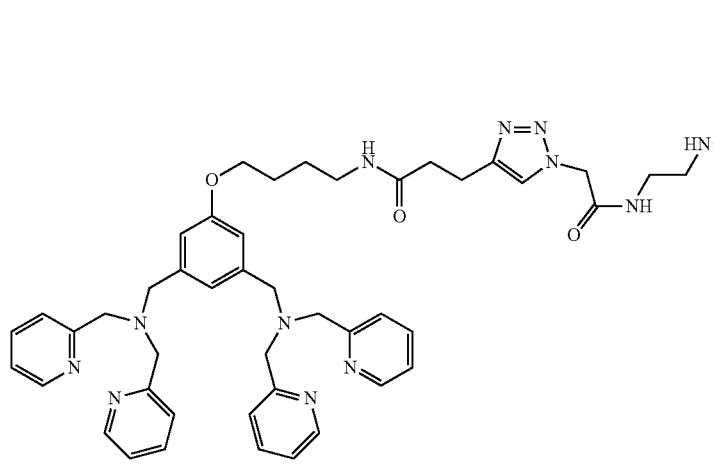

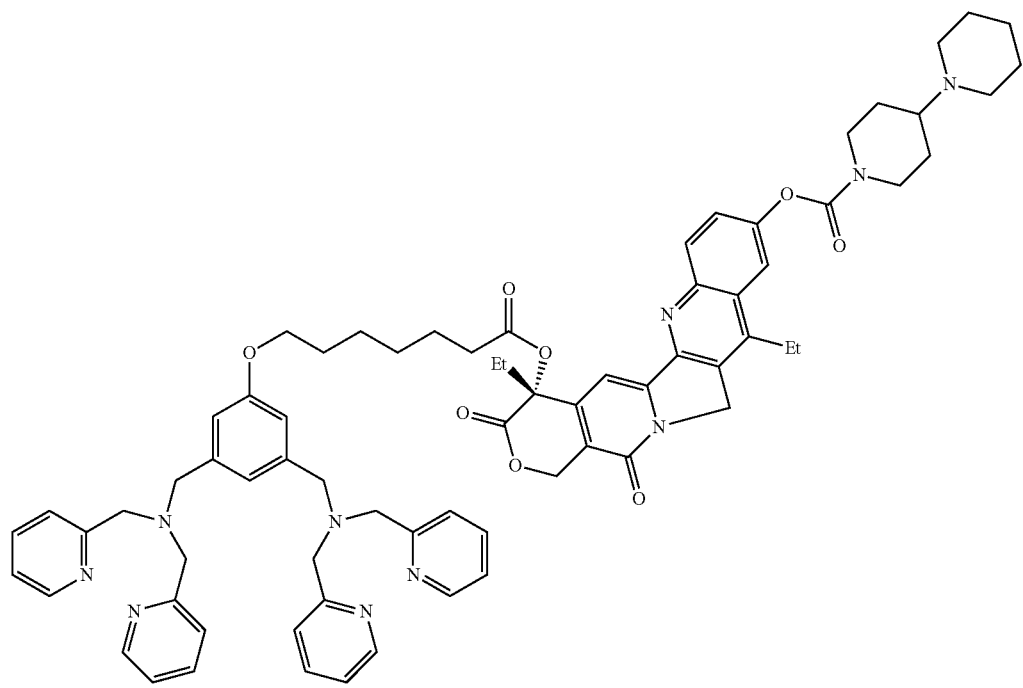
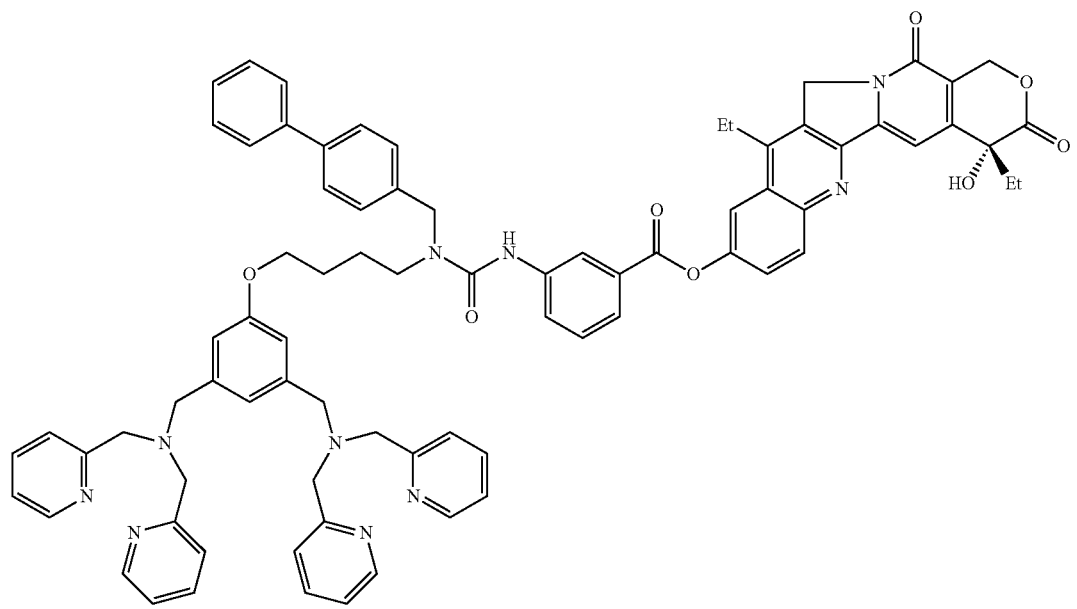

-continued
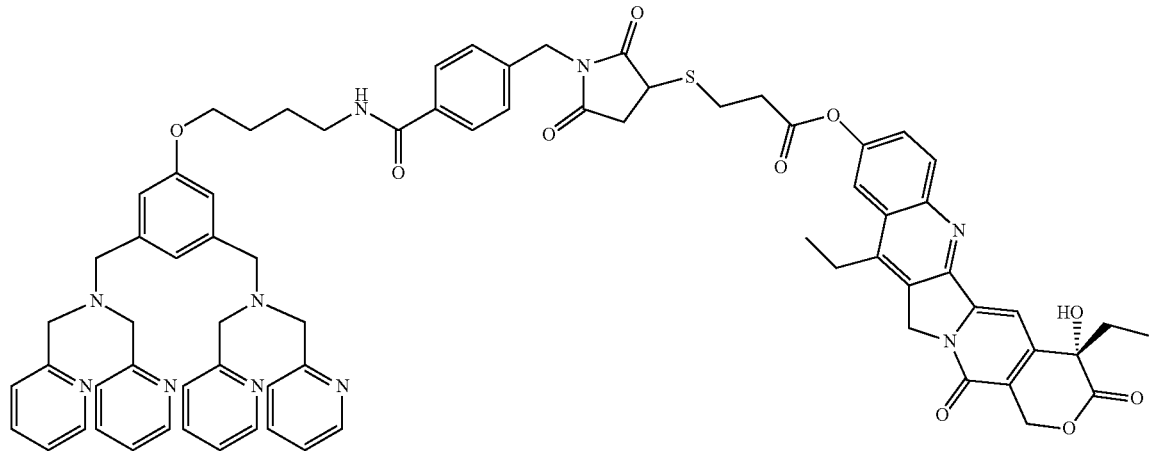
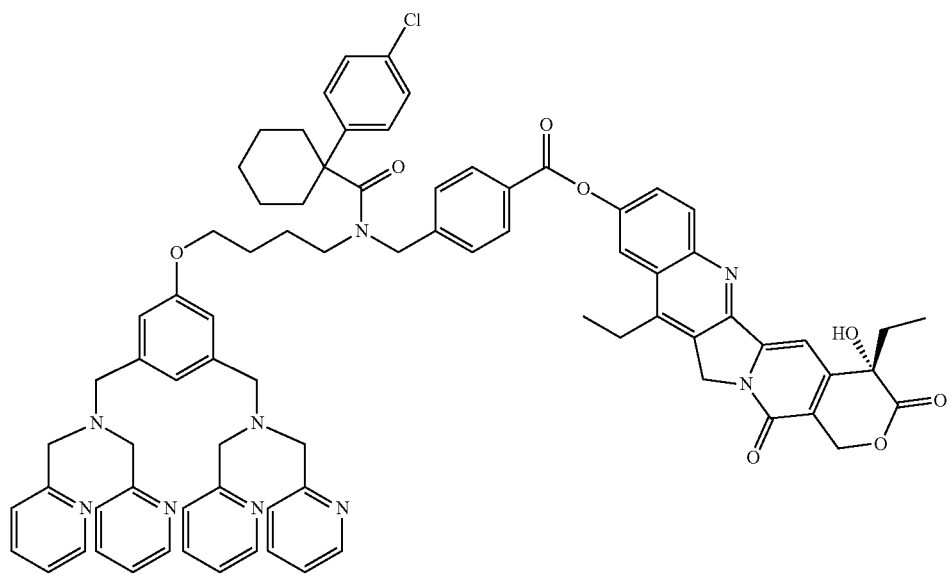
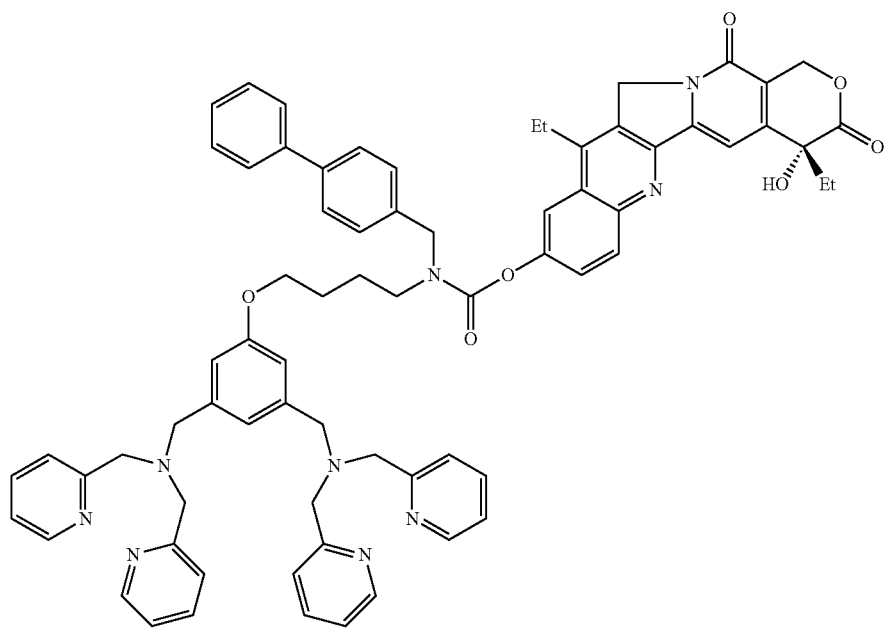

-continued

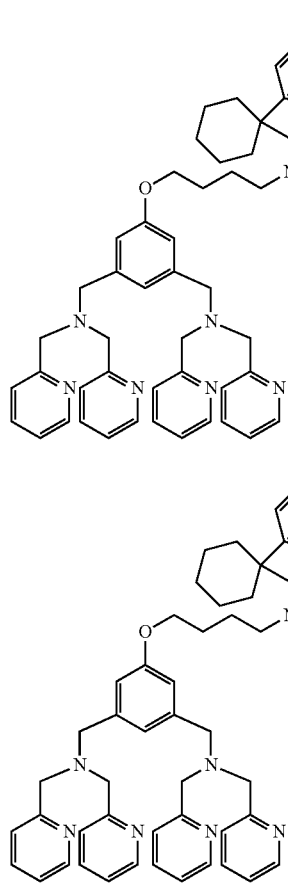
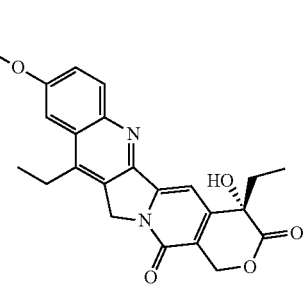
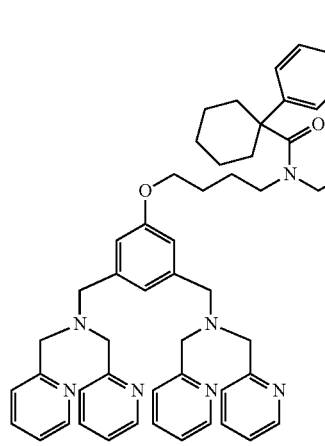

18. A pharmaceutical composition comprising a pharmaceutically acceptable carrier and a complex of a metal ion and a compound of claim 1, wherein the metal ion is a cation having two or more charges.

19. The pharmaceutical composition of claim 18, wherein the metal ion is $Zn^{2+}$, $Cu^{2+}$, $Ca^{2+}$, $Mg^{2+}$, $Mn^{2+}$, $Ni^{2+}$, $Co^{2+}$, $Fe^{2+}$, $Cd^{2+}$, or a combination thereof.

20. A method of treating a condition associated with cells containing inside-out phosphatidylserine, the method comprising administering to a subject in need thereof an effective amount of a compound of claim 1, wherein the condition is cancer.

21. The method of claim 20, wherein the compound is a metal complex formed of a compound of formula (I) and a metal ion.

22. The method of claim 21, wherein the metal ion is $Zn^{2+}$, $Cu^{2+}$, $Ca^{2+}$, $Mg^{2+}$, $Mn^{2+}$, $Ni^{2+}$, $Co^{2+}$, $Fe^{2+}$, $Cd^{2+}$, or a combination thereof.

23. The compound of claim 16, wherein the compound is:

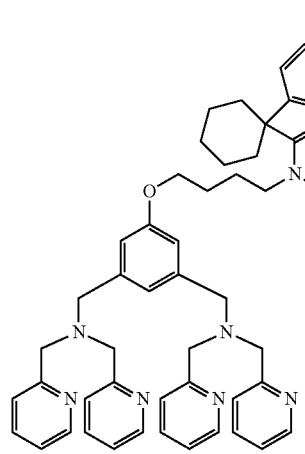
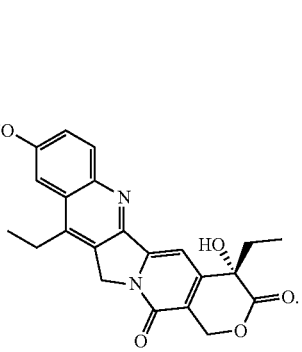

* * * * *